United States Patent
Kato et al.

(10) Patent No.: US 9,564,595 B2
(45) Date of Patent: Feb. 7, 2017

(54) BIS-CARBAZOLE DERIVATIVE AND ORGANIC ELECTROLUMINESCENT ELEMENT USING SAME

(75) Inventors: Tomoki Kato, Chiba (JP); Nobuhiro Yabunouchi, Chiba (JP); Takahiro Fujiyama, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 643 days.

(21) Appl. No.: 14/006,514

(22) PCT Filed: Mar. 21, 2012

(86) PCT No.: PCT/JP2012/057236
§ 371 (c)(1),
(2), (4) Date: Sep. 20, 2013

(87) PCT Pub. No.: WO2012/128298
PCT Pub. Date: Sep. 27, 2012

(65) Prior Publication Data
US 2014/0008633 A1  Jan. 9, 2014

(30) Foreign Application Priority Data

Mar. 24, 2011 (JP) .................... 2011-066821

(51) Int. Cl.
| | | |
|---|---|---|
| H01L 51/54 | (2006.01) |
| C09K 11/06 | (2006.01) |
| H01L 51/00 | (2006.01) |
| C07D 209/86 | (2006.01) |
| C07D 209/88 | (2006.01) |
| H01L 51/50 | (2006.01) |

(52) U.S. Cl.
CPC ......... H01L 51/0052 (2013.01); C07D 209/86 (2013.01); C07D 209/88 (2013.01); H01L 51/0072 (2013.01); H01L 51/0085 (2013.01); H01L 51/0086 (2013.01); H01L 51/0087 (2013.01); H01L 51/0088 (2013.01); H01L 51/5016 (2013.01)

(58) Field of Classification Search
CPC ... C07D 209/82; C07D 209/86; C07D 209/88; C09K 11/06; C09K 2211/00; C09K 2211/1018; C09K 2211/1022; C09K 2211/1025; C09K 2211/1029; H01L 51/0032; H01L 51/005; H01L 51/0051; H01L 51/0052; H01L 51/0071; H01L 51/0072; H01L 51/0085; H01L 51/0086; H01L 51/0087; H01L 51/0088; H01L 51/50; H01L 51/5012; H01L 51/5016; H01L 51/5048; H01L 51/5052; H01L 51/5056; H01L 51/5064; H01L 51/5088
USPC ....... 428/690, 691, 917, 411.4, 336; 427/58, 427/66; 313/500–512; 257/40, 88–104, 257/E51.001–E51.052; 252/301.16–301.35; 548/440

See application file for complete search history.

(56) References Cited

U.S. PATENT DOCUMENTS

| | | | |
|---|---|---|---|
| 2004/0113547 A1* | 6/2004 | Son ........................ | C09K 11/06 313/504 |
| 2008/0284322 A1* | 11/2008 | Hosokawa ........... | C07D 215/24 313/504 |
| 2009/0167165 A1 | 7/2009 | Otsu et al. | |
| 2009/0179554 A1 | 7/2009 | Kuma et al. | |
| 2011/0031482 A1 | 2/2011 | Furukawa et al. | |
| 2011/0278552 A1 | 11/2011 | Numata et al. | |
| 2012/0175599 A1* | 7/2012 | Yokoyama ........... | C07D 417/14 257/40 |
| 2012/0205642 A1 | 8/2012 | Yokoyama et al. | |
| 2012/0273767 A1 | 11/2012 | Yokoyama et al. | |

(Continued)

FOREIGN PATENT DOCUMENTS

| | | |
|---|---|---|
| JP | 3139321 B2 | 2/2001 |
| JP | 2001-220380 A | 8/2001 |

(Continued)

OTHER PUBLICATIONS

Extended European Search Report issued Jul. 10, 2014 in Patent Application No. 12759920.7.

(Continued)

*Primary Examiner* — Andrew K Bohaty
(74) *Attorney, Agent, or Firm* — Oblon, McClelland, Maier & Neustadt, L.L.P.

(57) ABSTRACT

A biscarbazole derivative represented by formula (1):

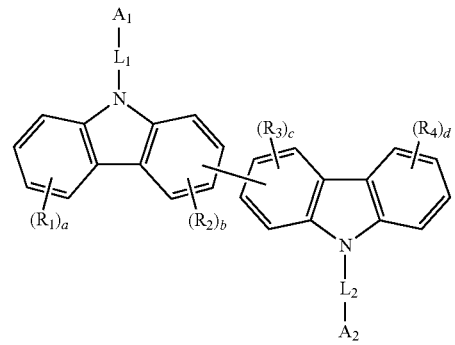

wherein $A_1$, $A_2$, $L_1$, $L_2$, $R_1$ to $R_4$, and a to d are as defined in the specification, is useful as a material for forming organic EL devices and the organic EL devices including the derivative is capable of driving at a low voltage and has a long lifetime.

18 Claims, 1 Drawing Sheet

(56) References Cited

U.S. PATENT DOCUMENTS

| | | | |
|---|---|---|---|
| 2012/0305900 A1* | 12/2012 | Kim | C09K 11/06 257/40 |
| 2013/0264558 A1 | 10/2013 | Matsuki et al. | |
| 2013/0306963 A1 | 11/2013 | Yamamoto et al. | |
| 2013/0341613 A1 | 12/2013 | Nagao et al. | |

FOREIGN PATENT DOCUMENTS

| | | |
|---|---|---|
| JP | 2008-135498 A | 6/2008 |
| JP | 2009-114369 A | 5/2009 |
| JP | 2010-135467 A | 6/2010 |
| JP | 2011-54391 A | 3/2011 |
| JP | 2011-54931 A | 3/2011 |
| JP | 2012-175025 A | 9/2012 |
| JP | 2013-510141 A | 3/2013 |
| JP | 2013-533604 A | 8/2013 |
| JP | 2014-511564 A | 5/2014 |
| KR | 10-2011-0066766 | 6/2011 |
| WO | WO 2007/077810 A1 | 7/2007 |
| WO | WO 2007/119816 A1 | 10/2007 |
| WO | WO 2007/132678 A1 | 11/2007 |
| WO | WO 2007/132886 A1 | 11/2007 |
| WO | WO 2009/060757 A1 | 5/2009 |
| WO | WO 2009/104488 A1 | 8/2009 |
| WO | WO 2011/024451 A1 | 3/2011 |
| WO | WO 2011/048821 A1 | 4/2011 |
| WO | WO 2011/048822 A1 | 4/2011 |
| WO | WO 2011/055934 A2 | 5/2011 |
| WO | WO 2011/125680 A1 | 10/2011 |
| WO | WO 2011/132683 A1 | 10/2011 |
| WO | WO 2011/139055 A2 | 11/2011 |
| WO | WO 2011/16216 A1 | 12/2011 |
| WO | WO 2012/090806 A1 | 7/2012 |
| WO | WO 2012/124622 A1 | 9/2012 |

OTHER PUBLICATIONS

International Search Report issued May 29, 2012, in PCT/JP2012/057236.

Office Action issued Jan. 26, 2016 in Japanese Patent Application No. 2013-505994.

* cited by examiner

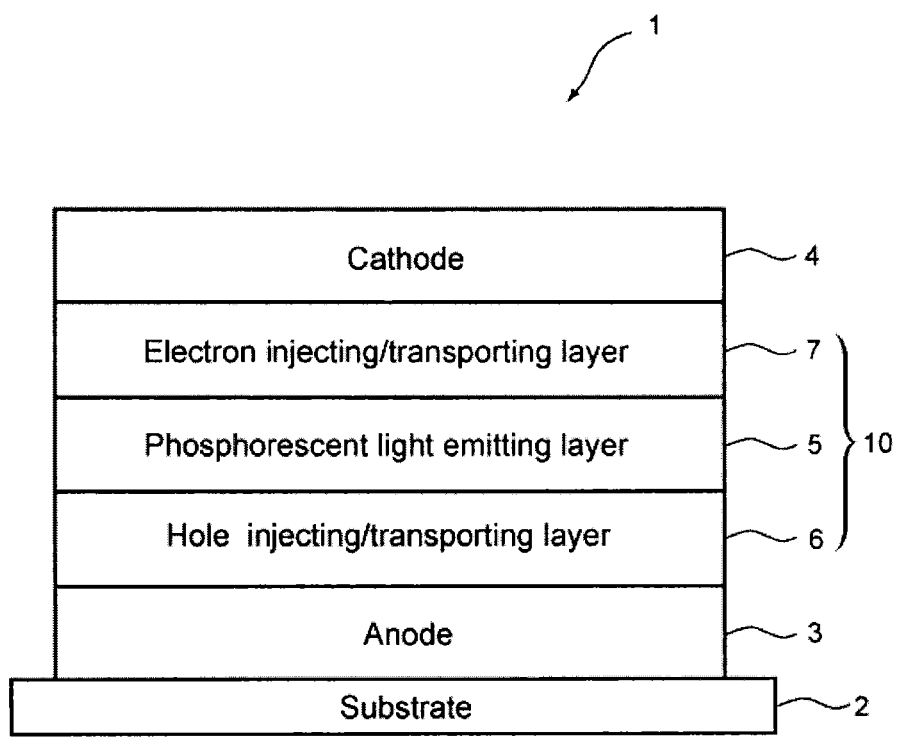

BIS-CARBAZOLE DERIVATIVE AND ORGANIC ELECTROLUMINESCENT ELEMENT USING SAME

CROSS REFERENCE TO RELATED APPLICATIONS

The present application is a 35 U.S.C. §371 national stage patent application of International patent application PCT/JP2012/057236, filed on Mar. 21, 2012, published as WO/2012/128298 on Sep. 27, 2012, the text of which is incorporated by reference, and claims the benefit of the filing date of Japanese application no. 2011-066821, filed on Mar. 24, 2011, the text of which is also incorporated by reference.

TECHNICAL FIELD

The present invention relates to biscarbazole derivatives and organic electroluminescence devices employing the biscarbazole derivative. Particularly, the present invention relates to biscarbazole derivatives having a biscarbazole skeleton wherein two carbazole structures are directly bonded to each other by a carbon-to-carbon bond and a C-carbazolyl group (1-, 2-, 3-, or 4-carbazolyl group), a N-carbazolyl group (9-carbazolyl group), or a N-carbazolylaryl group is directly bonded to the nitrogen atom of one of the carbazole structure and organic electroluminescence devices employing the biscarbazole derivative.

BACKGROUND ART

Organic electroluminescence (EL) devices utilizing organic substances are much expected to be useful as inexpensive, large-sized full color display devices of solid state emission type and many developments have been made thereon. An organic EL device is generally constructed from a light emitting layer and a pair of opposite electrodes sandwiching the light emitting layer. When an electric field is applied between the electrodes, electrons are injected from a cathode and holes are injected from an anode. The injected electrons recombine with the injected holes in the light emitting layer to form excited states. When the excited states return to the ground state, the energy is released as light.

A phosphorescent organic EL device wherein a phosphorescent organic material is used in the light emitting layer has been proposed. Utilizing the singlet excited state and the triplet excited state of the phosphorescent organic material, a high emission efficiency can be obtained by the phosphorescent organic EL device. When electrons and holes are recombined in an organic EL device, singlet excitons and triplet excitons may generate in a ratio of 1:3 in accordance with their difference in the spin multiplicity. Therefore, an organic EL device employing the phosphorescent emitting material would achieve an emission efficiency three to four times higher than that of an organic EL device employing only the fluorescent emitting material.

The early organic EL device requires a high driving voltage and is insufficient in the emission efficiency and durability. To eliminate these problems, various technical improvements have been made.

The improved emission efficiency and the prolonged lifetime are very important for reducing the power consumption of displays and improving the durability. Therefore, further improvements have been still required. In addition, many studies have been made in order to improve the emission efficiency and the device lifetime of organic EL devices employing a phosphorescent emitting material.

To solve the above problems, Patent Document 1 discloses a derivative having a 3,3'-biscarbazole skeleton as the phosphorescent host material. Patent Document 2 discloses a derivative having a 6,6'-bis(9-carbazolyl)-N,N'-disubstituted-3,3'-biscarbazole skeleton as the hole transporting material. Patent Document 3 discloses a compound having a carbazole, dibenzofuran, or dibenzothiophene skeleton as the phosphorescent host material, for example, 6,6'-bis(9-carbazolyl)-N,N'-diphenyl-3,3'-biscarbazole (Compound 32).

Patent Document 1 describes the use of the 3,3'-biscarbazole derivative in the phosphorescent light emitting layer, but describes nothing about the use in the hole transporting layer.

Patent Document 2 describes the use of the derivative having a 6,6'-bis(9-carbazolyl)-N,N'-disubstituted-3,3'-biscarbazole skeleton as the hole transporting material and a high heat stability of the derivative. However, since the derivative having such a skeleton has a large ionization potential, the driving voltage unfavorably increases if the derivative is used in the hole transporting layer adjacent to the light emitting layer.

Patent Document 3 merely describes the derivative having a carbazole, dibenzofuran, or dibenzothiophene skeleton as the phosphorescent host material, and suggests nothing about its function as the hole transporting material.

Patent Document 4 describes a compound having a biscarbazole skeleton wherein two carbazole structures are directly bonded to each other by a carbon-carbon bond (formulae (1a) and (1b)). A (hetero)arylamino group is bonded to the nitrogen atom of one carbazole skeleton through a 4,4'-biphenyldiyl group or a 9,9-dimethylfluorene-2,7-diyl group. Only in the compound 76, two aryl groups of the amino group are bonded to each other via a single bond.

Patent Document 5 describes a compound having a biscarbazole skeleton wherein two carbazole structures are directly bonded to each other by a carbon-to-carbon bond and a carbazolyl group is bonded to the nitrogen atom of the carbazole structure. The carbazolyl group bonded to the nitrogen atom must have a heterocyclic group selected from a dibenzofuranyl group, a dibenzothiophenyl group, and a carbazolyl group.

PRIOR ART DOCUMENTS

Patent Documents

Patent Document 1: JP 2008-135498A
Patent Document 2: JP 2001-220380A
Patent Document 3: WO2007/077810
Patent Document 4: WO2011/024451
Patent Document 5: WO2007/119816

DISCLOSURE OF INVENTION

An object of the present invention is to provide an organic EL device capable of driving at low voltage and having a long lifetime.

As a result of extensive research for achieving the above object, the inventors have found that a biscarbazole derivative having a specific group or linker has a small ionization potential and the biscarbazole derivative improves the hole injecting ability of an organic EL device thereby to reduce the driving voltage.

Namely, the present invention provides a biscarbazole derivative represented by formula (1):

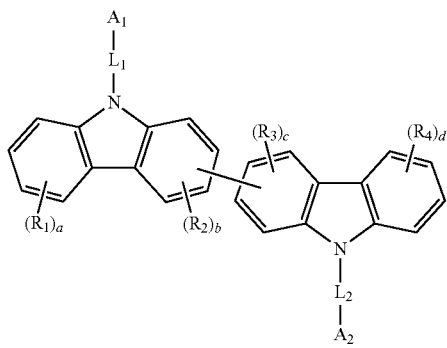
(1)

wherein:

$L_1$ and $L_2$ are the same or different and each independently represents a linker selected from a single bond and a substituted or unsubstituted arylene group having 6 to 30 ring carbon atoms;

$R_1$ to $R_4$ are the same or different and each independently represents a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted aryl group having 6 to 30 ring carbon atoms, a substituted or unsubstituted aryloxy group having 6 to 30 ring carbon atoms, a substituted or unsubstituted arylsilyl group having 6 to 30 carbon atoms, a substituted or unsubstituted aralkyl group having 7 to 30 carbon atoms, or a substituted or unsubstituted heteroaryl group having 5 to 30 ring atoms, wherein the heteroaryl group is selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolinyl group, a cinnolinyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group;

adjacent $R_1$ groups, adjacent $R_2$ groups, adjacent $R_3$ groups, and adjacent $R_4$ groups may be bonded to each other to form a saturated or unsaturated, substituted or unsubstituted divalent group which completes a ring structure;

each of a and d independently represents an integer of 0 to 4;

each of b and c independently represents an integer of 0 to 3;

$A_1$ represents a substituted or unsubstituted aryl group having 6 to 30 ring carbon atoms or a substituted or unsubstituted heteroaryl group having 5 to 30 ring atoms, wherein the heteroaryl group is selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolinyl group, a cinnolinyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group;

$A_2$ represent a group represented by formula (2-1) or (2-2):

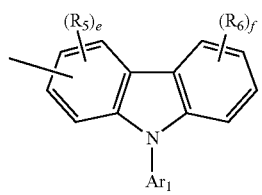
(2-1)

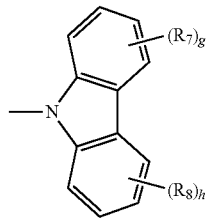
(2-2)

wherein:

$Ar_1$ represents a substituted or unsubstituted aryl group having 6 to 30 ring carbon atoms or a substituted or unsubstituted heteroaryl group having 5 to 30 ring atoms;

$R_5$ to $R_8$ are the same or different and each independently represents a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted aryl group having 6 to 30 ring carbon atoms, a substituted or unsubstituted aryloxy group having 6 to 30 ring carbon atoms, a substituted or unsubstituted arylsilyl group having 6 to 30 carbon atoms, or a substituted or unsubstituted aralkyl group having 7 to 30 carbon atoms;

adjacent $R_5$ groups and adjacent $R_6$ groups may be bonded to each other to form a saturated or unsaturated, substituted or unsubstituted divalent group which completes a ring structure;

each of f, g, and h independently represents an integer of 0 to 4;

e represents an integer of 0 to 3; and provided that $L_2$ represent a single bond when $A_2$ is a group represented by formula (2-1), and $L_2$ represents a single bond or a substituted or unsubstituted arylene group having 6 to 30 ring carbon atoms when $A_2$ is a group represented by formula (2-2).

The present invention further provides an organic electroluminescence device which comprises an anode, a cathode and one or more organic thin layers disposed between the anode and the cathode, wherein at least one layer of the organic thin layers comprises at least one biscarbazole derivative represented by formula (1).

According to the present invention, an organic electroluminescence device capable of driving at a low voltage and having a long lifetime is provided.

BRIEF DESCRIPTION OF DRAWINGS

FIG. 1 is a schematic sectional view of an example of the organic EL device of the invention.

BEST MODE FOR CARRYING OUT THE INVENTION

The present invention will be described in detail.
Biscarbazole Derivative

The biscarbazole derivative of the invention is represented by formula (1):

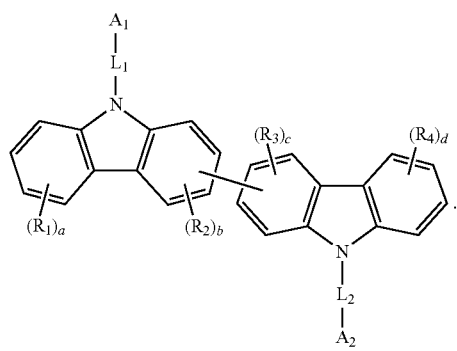

(1)

In formula (1), $L_1$ and $L_2$ are the same or different and each independently represents a linker selected from a single bond and a substituted or unsubstituted arylene group having 6 to 30, preferably 6 to 18 ring carbon atoms.

$R_1$ to $R_4$ are the same or different and each independently represents a fluorine atom; a cyano group; a substituted or unsubstituted alkyl group having 1 to 20, preferably 1 to 10 carbon atoms; a substituted or unsubstituted cycloalkyl group having 3 to 20, preferably 3 to 10 carbon atoms; a substituted or unsubstituted alkoxy group having 1 to 20, preferably 1 to 10 carbon atoms; a substituted or unsubstituted haloalkyl group having 1 to 20, preferably 1 to 10 carbon atoms; a substituted or unsubstituted haloalkoxy group having 1 to 20, preferably 1 to 10 carbon atoms; a substituted or unsubstituted alkylsilyl group having 1 to 10, preferably 1 to 6 carbon atoms; a substituted or unsubstituted aryl group having 6 to 30, preferably 6 to 18 ring carbon atoms; a substituted or unsubstituted aryloxy group having 6 to 30, preferably 6 to 18 ring carbon atoms; a substituted or unsubstituted arylsilyl group having 6 to 30, preferably 6 to 18 carbon atoms; a substituted or unsubstituted aralkyl group having 7 to 30, preferably 7 to 19 carbon atoms; or a substituted or unsubstituted heteroaryl group having 5 to 30, preferably 6 to 18 ring atoms. Adjacent $R_1$ groups, adjacent $R_2$ groups, adjacent $R_3$ groups, and adjacent $R_4$ groups may be bonded to each other to form a saturated or unsaturated, substituted or unsubstituted divalent group which completes a ring structure.

Each of a and d independently represents an integer of 0 to 4, and each of b and c independently represents an integer of 0 to 3.

$A_1$ represents a substituted or unsubstituted aryl group having 6 to 30, preferably 6 to 18 ring carbon atoms or a substituted or unsubstituted heteroaryl group having 5 to 30, preferably 6 to 18 ring atoms.

$A_2$ represents a group represented by formula (2-1) or (2-2):

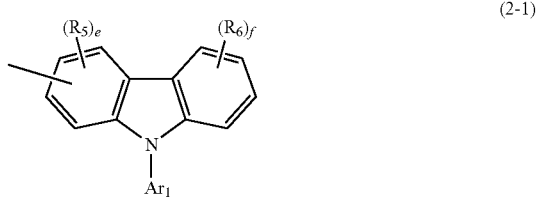

(2-1)

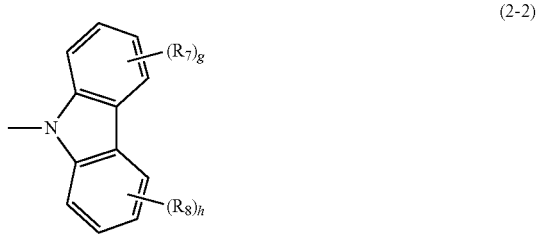

(2-2)

wherein:

$Ar_1$ represents a substituted or unsubstituted aryl group having 6 to 30, preferably 6 to 18 ring carbon atoms or a substituted or unsubstituted heteroaryl group having 5 to 30, preferably 6 to 18 ring atoms;

$R_5$ to $R_8$ are the same or different and each independently represents a fluorine atom; a cyano group; a substituted or unsubstituted alkyl group having 1 to 20, preferably 1 to 10 carbon atoms; a substituted or unsubstituted cycloalkyl group having 3 to 20, preferably 3 to 10 carbon atoms; a substituted or unsubstituted alkoxy group having 1 to 20, preferably 1 to 10 carbon atoms; a substituted or unsubstituted haloalkyl group having 1 to 20, preferably 1 to 10 carbon atoms; a substituted or unsubstituted haloalkoxy group having 1 to 20, preferably 1 to 10 carbon atoms; a substituted or unsubstituted alkylsilyl group having 1 to 10, preferably 1 to 6 carbon atoms; a substituted or unsubstituted aryl group having 6 to 30, preferably 6 to 18 ring carbon atoms; a substituted or unsubstituted aryloxy group having 6 to 30, preferably 6 to 18 ring carbon atoms; a substituted or unsubstituted arylsilyl group having 6 to 30, preferably 6 to 18 carbon atoms; or a substituted or unsubstituted aralkyl group having 7 to 30, preferably 7 to 19 carbon atoms. Adjacent $R_5$ groups and adjacent $R_6$ groups may be bonded to each other to form a saturated or unsaturated, substituted or unsubstituted divalent group which completes a ring structure;

each of f, g, and h independently represents an integer of 0 to 4; and e represents an integer of 0 to 3;

provided that $L_2$ represent a single bond when $A_2$ is a group represented by formula (2-1), and $L_2$ represents a single bond or a substituted or unsubstituted arylene group having 6 to 30 ring carbon atoms, preferably a substituted or unsubstituted arylene group having 6 to 30 ring carbon atoms when $A_2$ is a group represented by formula (2-2).

In formulae (1), (2-1), and (2-2), when any one of a to d and e to h is zero, each of $(R_1)_0$, $(R_2)_0$, $(R_3)_0$, $(R_4)_0$, $(R_5)_0$, $(R_6)_0$, $(R_7)_0$, and $(R_8)_0$ represents a hydrogen atom.

Examples of the arylene group for $L_1$ and $L_2$ include divalent residues of aromatic compounds selected from benzene, naphthalene, phenanthrene, biphenyl, terphenyl (inclusive of isomers), quaterphenyl (inclusive of isomers), fluoranthene, triphenylene, fluorene, 9,9-dimethylfluorene, benzo[c]phenanthrene, benzo[a]triphenylene, naphtho[1,2-c]phenanthrene, naphtho[1,2-a]triphenylene, dibenzo[a,c]triphenylene, and benzo[b]fluoranthene, with a 1,4-phenylene group, a 1,3-phenylene group, a naphthalene-2,6-diyl group, a naphthalene-2,7-diyl group, and a 9,9-dimethylfluorene-2,7-diyl group being preferred.

Examples of the alkyl group for $R_1$ to $R_4$ and $R_5$ to $R_8$ include a methyl group, an ethyl group, a n-propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 2-methylpentyl group, a 1-pentyl hexyl group, a 1-butylpentyl group, a 1-pentyloctyl group, and a 3-methylpentyl group, with a methyl group, a t-butyl group, an ethyl group, a n-propyl group, and an isopropyl group being preferred.

Examples of the cycloalkyl group for $R_1$ to $R_4$ and $R_5$ to $R_8$ include a cyclopropyl group, a cyclobutyl group, a cyclopentyl group, a cyclohexyl group, and a cyclooctyl group, with a cyclopentyl group and a cyclohexyl group being preferred.

Examples of the alkoxy group for $R_1$ to $R_4$ and $R_5$ to $R_8$ include a group represented by —OY wherein Y represents the alkyl group mentioned above, with a methoxy group, an ethoxy group, and a propoxy group being preferred.

Examples of the haloalkyl group for $R_1$ to $R_4$ and $R_5$ to $R_8$ include a group obtained by replacing at least one hydrogen atom of the alkyl group mentioned above with a halogen atom selected from a fluorine atom, a chlorine atom, an iodine atom, and a bromine atom, with a trifluoromethyl group, a 2,2,2-trifluoroethyl group, a 1,1,2,2,2-pentafluoroethyl group, and a 1,1,1,3,3,3-hexafluoro-2-propyl group being preferred.

Examples of the haloalkoxy group for $R_1$ to $R_4$ and $R_5$ to $R_8$ include —OY' wherein Y' represents the haloalkyl group mentioned above, with a trifluoromethoxy group, a 2,2,2-trifluoroethoxy group, a 1,1,2,2,2-pentafluoroethoxy group, and a 1,1,1,3,3,3-hexafluoro-2-propoxy group being preferred.

Examples of the alkylsilyl group for $R_1$ to $R_4$ and $R_5$ to $R_8$ include —SiH$_2$R, —SiHR$_2$, and —SiR$_3$, wherein R represents the alkyl group mentioned above and two or three R groups may be the same or different, with a trimethylsilyl group, a triethylsilyl group, and a t-butyldimethylsilyl group being preferred.

Examples of the aryl group for $R_1$ to $R_4$, $A_1$, $Ar_1$, and $R_5$ to $R_8$ include a phenyl group, a naphthyl group, a phenanthryl group, a biphenyl group, a terphenyl group, a quaterphenyl group, a fluoranthenyl group, a triphenylenyl group, a 9,9-dimethylfluorenyl group, a benzo[c]phenanthrenyl group, a benzo[a]triphenylenyl group, a naphtho[1,2-c]phenanthrenyl group, a naphtho[1,2-a]triphenylenyl group, a dibenzo[a,c]triphenylenyl group, and a benzo[b]fluoranthenyl group, with a phenyl group, a 4-biphenyl group, a 3-biphenyl group, a 5'-m-terphenyl group, a 1-naphthyl group, a 9,9-dimethylfluorene-2-yl group, a 2-naphthyl group, and a 9-phenanthrenyl group being preferred.

Examples of the arylsilyl group for $R_1$ to $R_4$ and $R_5$ to $R_8$ include —SiH$_2$R', —SiHR'$_2$, and —SiR'$_3$, wherein R' represents the aryl group mentioned above and two or three R' groups may be the same or different, with a triphenylsilyl group being preferred.

Examples of the aralkyl group for $R_1$ to $R_4$ and $R_5$ to $R_8$ include a group having 7 to 30 carbon atoms which is obtained by replacing one hydrogen atom of the alkyl group mentioned above with the aryl group mentioned above, with a benzyl group and a naphthylmethyl group being preferred.

The heteroaryl group for $R_1$ to $R_4$ and $A_1$ is selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolinyl group, a cinnolinyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group, with a furyl group, a thienyl group, a benzofuranyl group, a benzothiophenyl group, a dibenzofuranyl group, and a dibenzothiophenyl group being preferred.

The heteroaryl group for $Ar_1$ is a heteroaryl group having 5 to 30 ring atoms including at least one hetero atom selected from the group consisting of a nitrogen atom, an oxygen atom, and a sulfur atom. Examples thereof include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolinyl group, a cinnolinyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a carbazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group, with a furyl group, a thienyl group, a benzofuranyl group, a benzothiophenyl group, a dibenzofuranyl group, and a dibenzothiophenyl group being preferred.

Examples of the divalent group which is formed by bonding adjacent $R_1$ groups, adjacent $R_2$ groups, adjacent $R_3$ groups, adjacent $R_4$ groups, adjacent $R_5$ groups, or adjacent $R_6$ groups to each other include a butane-1,4-diyl group and a 1,3-butadiene-1,4-diyl group.

The biscarbazole derivative represented by formula (1) is preferably a 2,2'-biscarbazole derivative, a 3,2'-biscarbazole derivative, a 2,3'-biscarbazole derivative, or a 3,3'-biscarbazole derivative each represented by formula (3-1), (3-2), (3-3) or (3-4), with a 3,3'-biscarbazole derivative being more preferred.

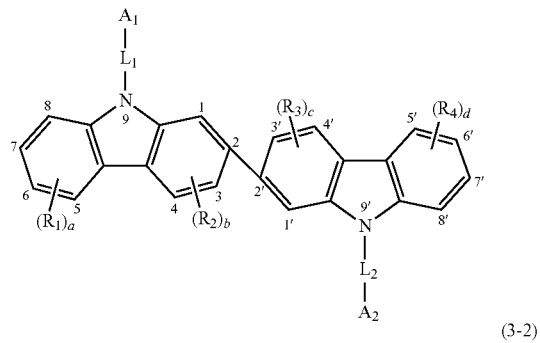

(3-1)

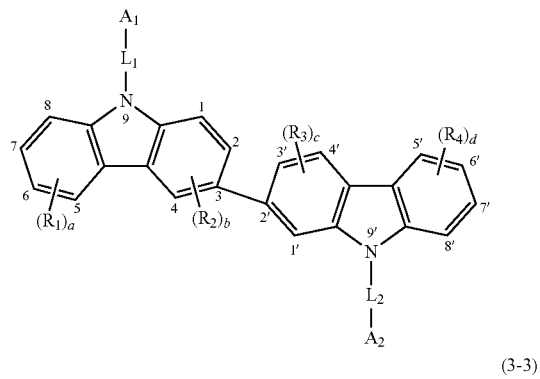

(3-2)

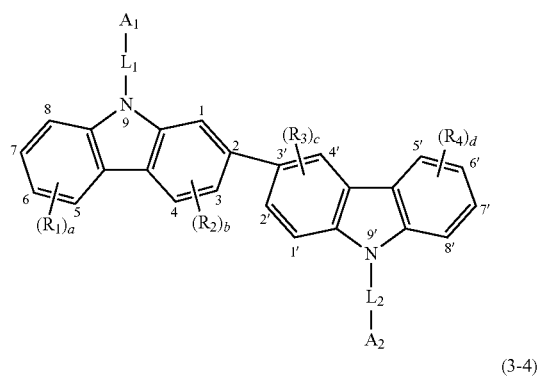

(3-3)

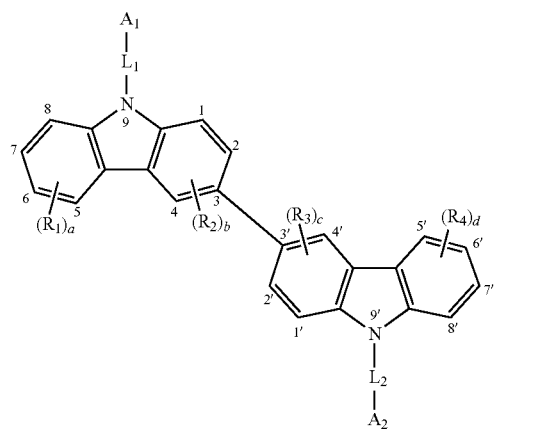

(3-4)

In formulae (3-1) to (3-4), $A_1$, $A_2$, $L_1$, $L_2$, $R_1$ to $R_4$, and a to d are as defined above.

The group represented by formula (2-1) is preferably represented by formula (2-3) or (2-4):

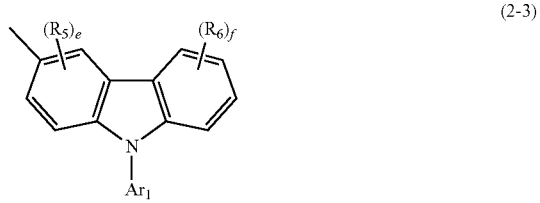

(2-3)

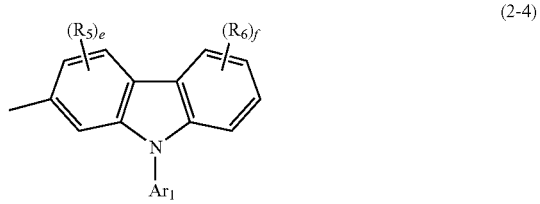

(2-4)

wherein $Ar_1$, $R_5$, $R_6$, e, and f are as defined above.

When $A_2$ is the group represented by formula (2-3), the ionization potential can be reduced sufficiently because of the electron-donating effect of $A_2$. The group represented by formula (2-4) is effective for reducing the driving voltage of organic EL device, because the hole mobility becomes large.

The optional substituent referred to by "substituted or unsubstituted" used above and below is selected from the group consisting of a fluorine atom, a cyano group, an alkyl group having 1 to 20 carbon atoms, a cycloalkyl group having 3 to 20 carbon atoms, an alkoxy group having 1 to 20 carbon atoms, a haloalkyl group having 1 to 20 carbon atoms, a haloalkoxy group having 1 to 20 carbon atoms, an alkylsilyl group having 1 to 10 carbon atoms, an aryl group having 6 to 30 ring carbon atoms, an aryloxy group having 6 to 30 ring carbon atoms, an arylsilyl group having 6 to 30 carbon atoms, an aralkyl group having 7 to 30 carbon atoms, and a heteroaryl group having 5 to 30 ring atoms. Examples of the substituent are the same as those mentioned above. When substituted with two or more substituents, the substituents may be the same or different.

The biscarbazole derivative represented by formula (1), for example, a 3,3'-biscarbazole derivative can be produced according to the following synthesis route:

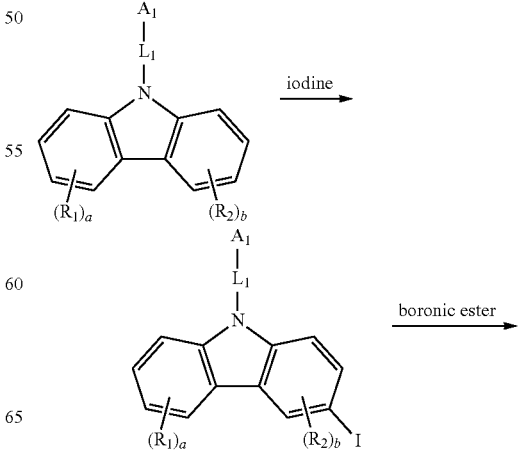

11

-continued

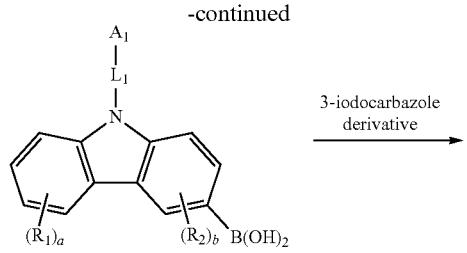

→ 3-iodocarbazole derivative →

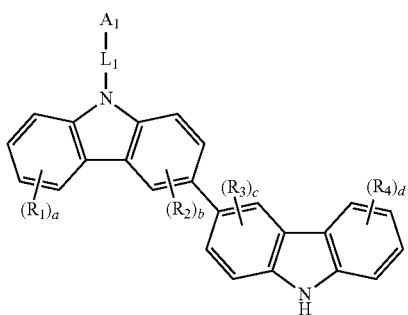

→ I—L₂—A₂
Br—L₂—A₂ →

12

-continued

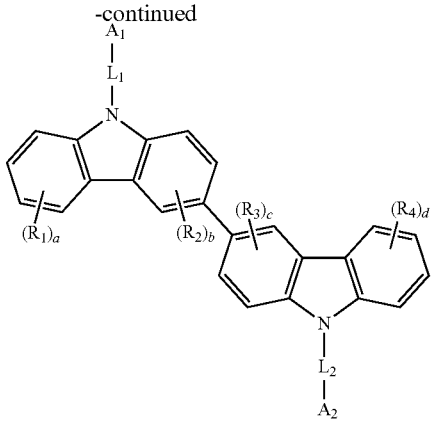

wherein $A_1$, $A_2$, $L_1$, $L_2$, $R_1$ to $R_4$, and a to d are as defined above.

Each elementary reaction is a known process. Therefore, one of ordinary skill in the art can easily select the conditions for each elementary reaction to easily synthesize other biscarbazole derivatives.

Examples of the biscarbazole derivative represented by formula (1) are shown below, although not limited to the following compounds.

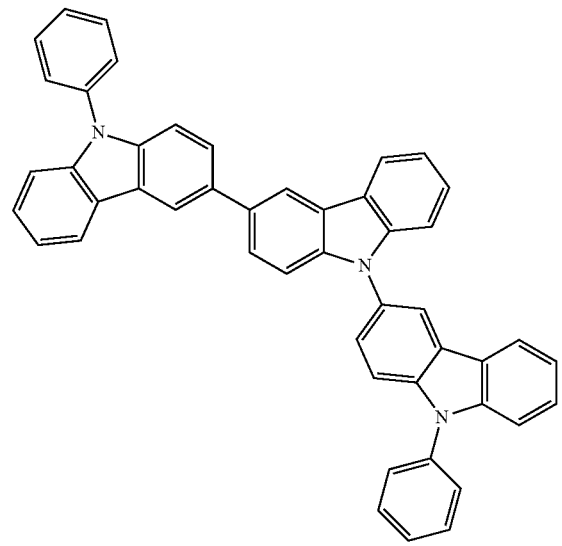

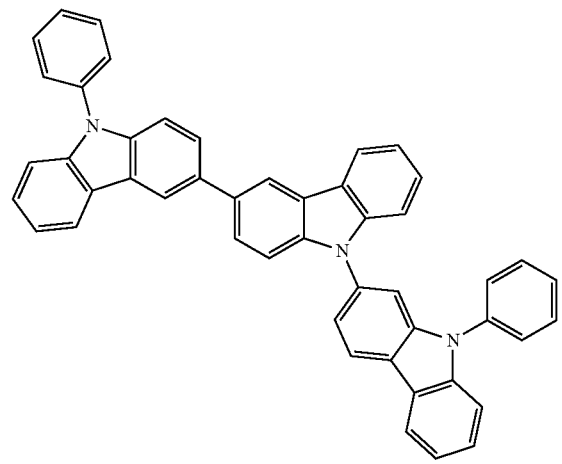

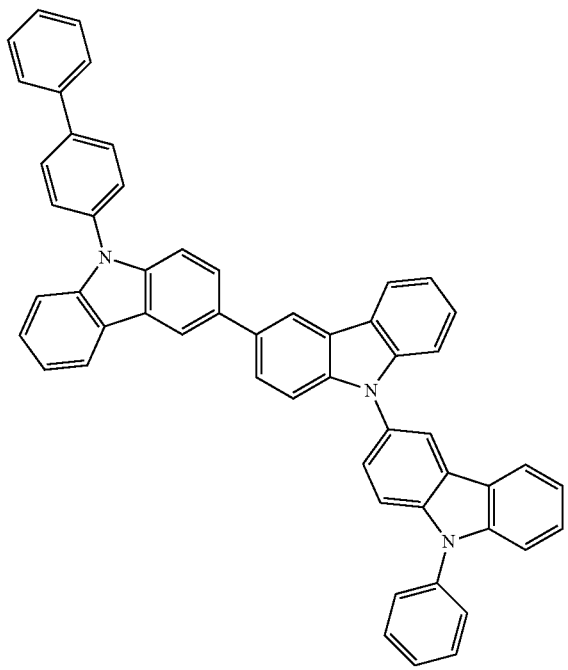
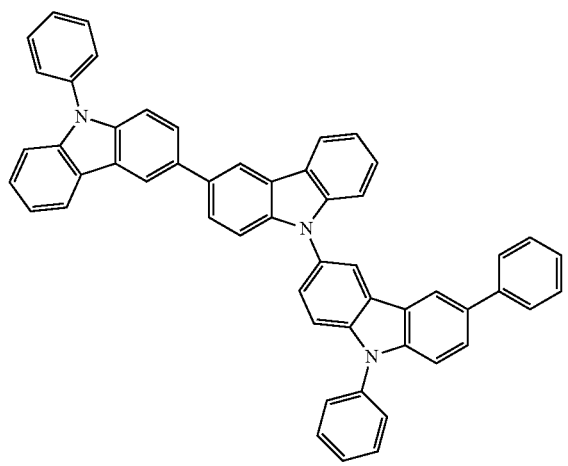
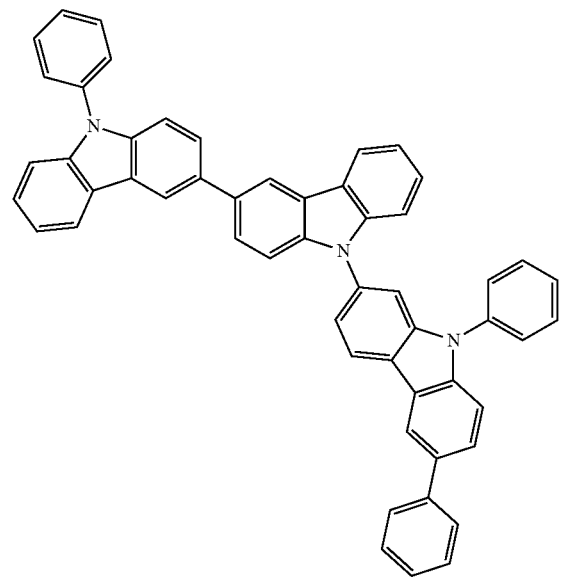

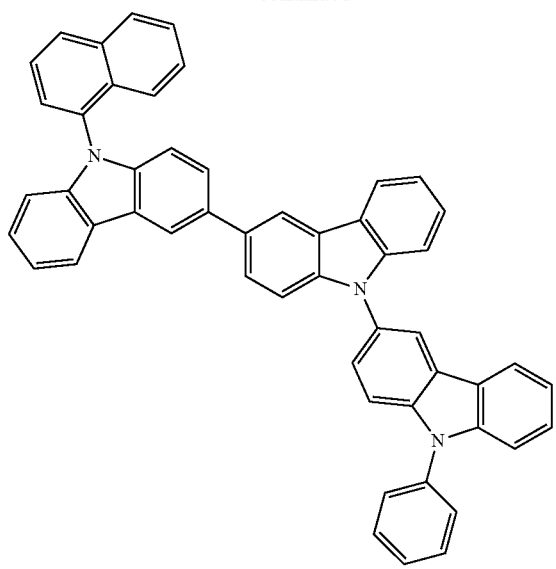
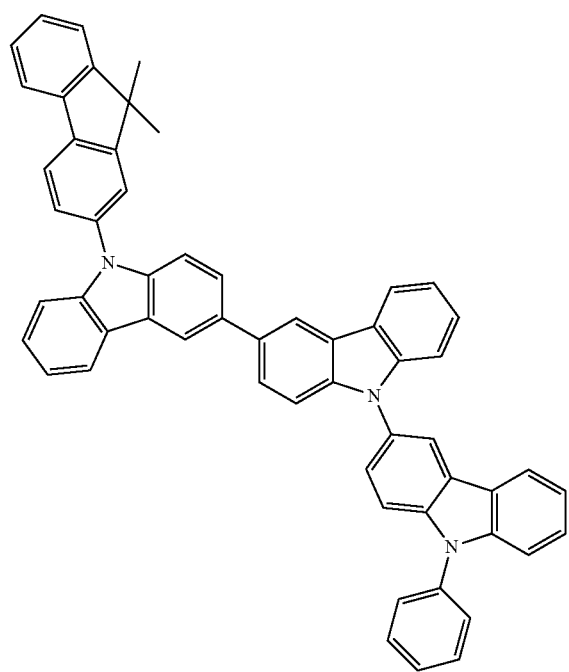

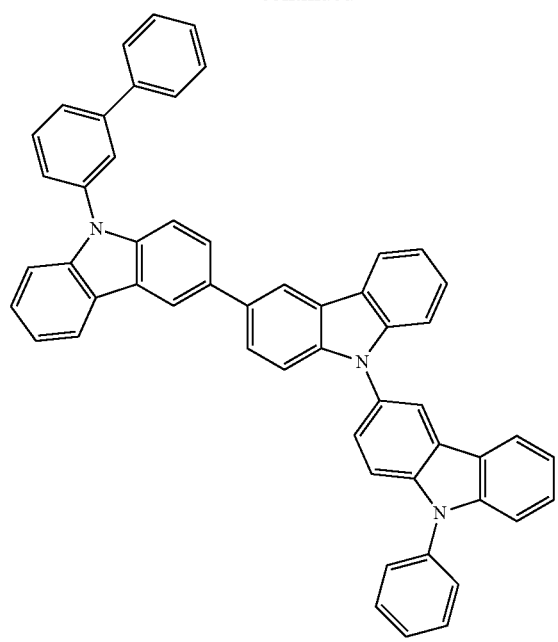
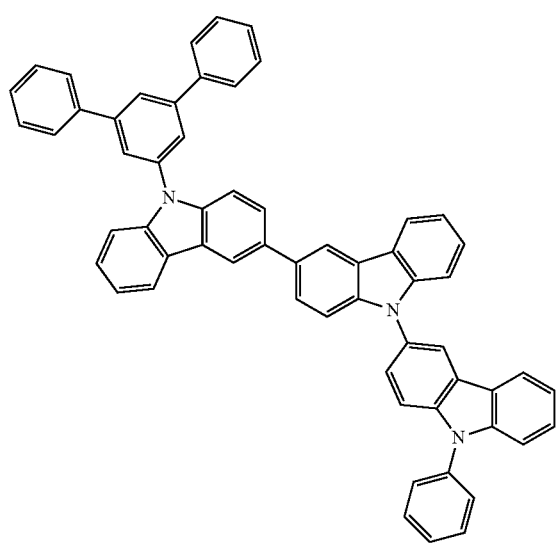
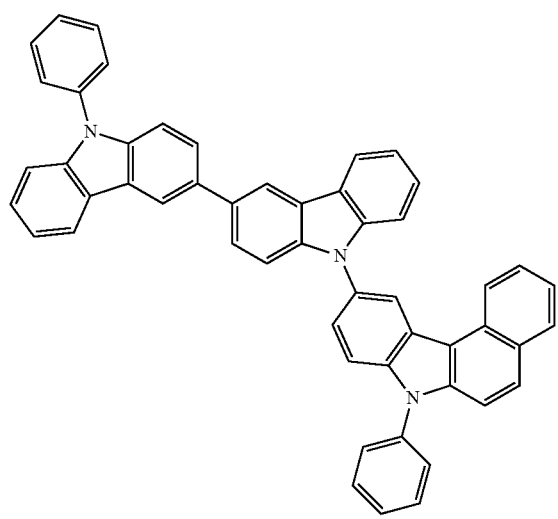

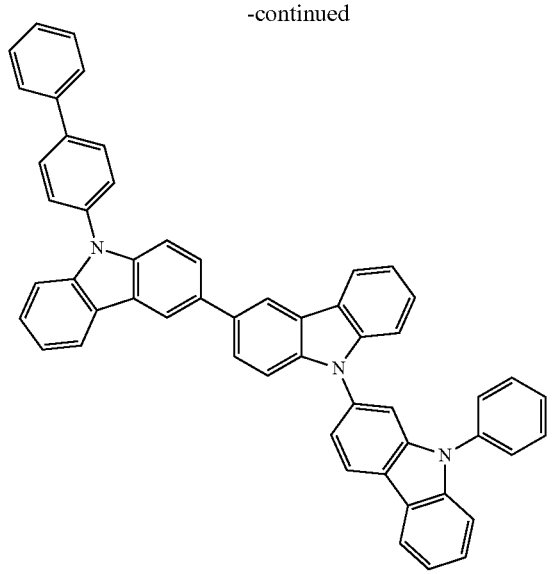
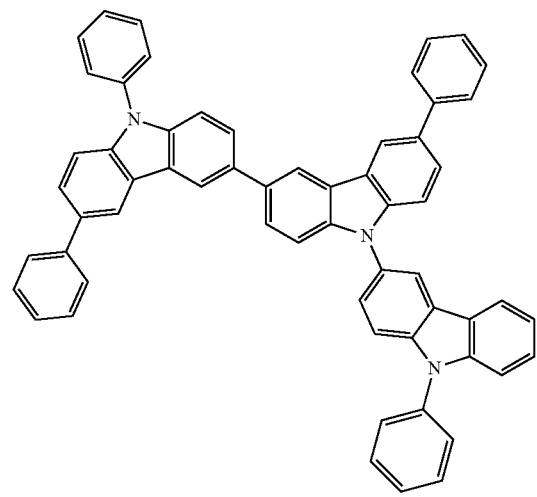
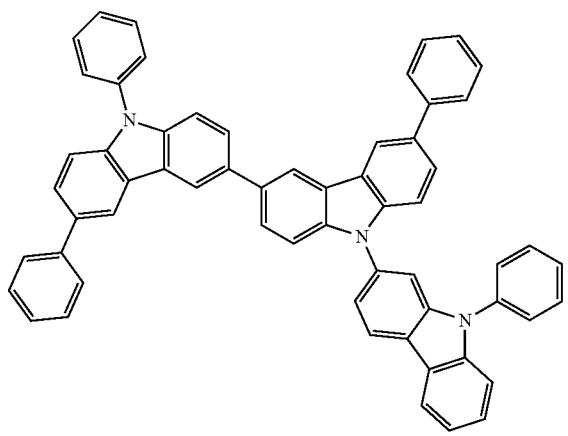

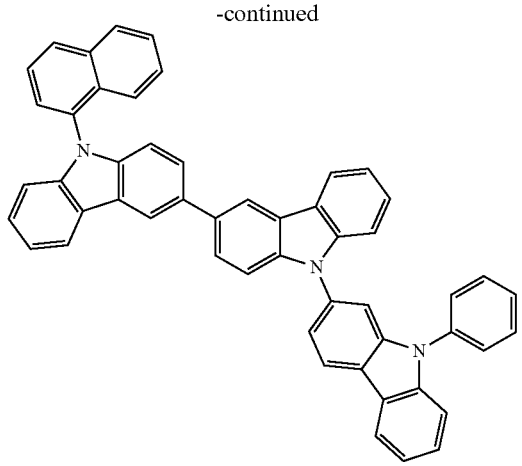
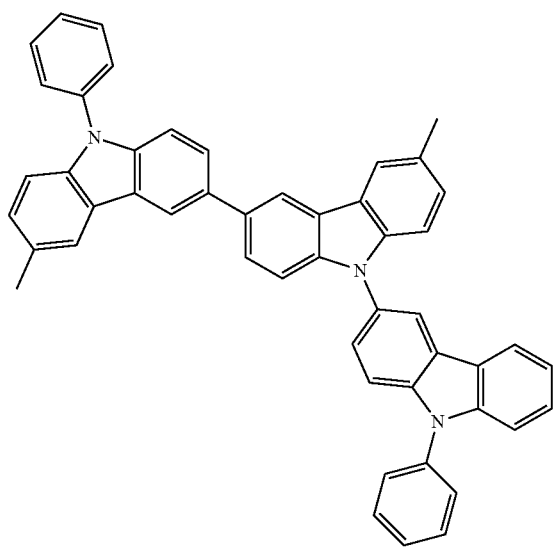
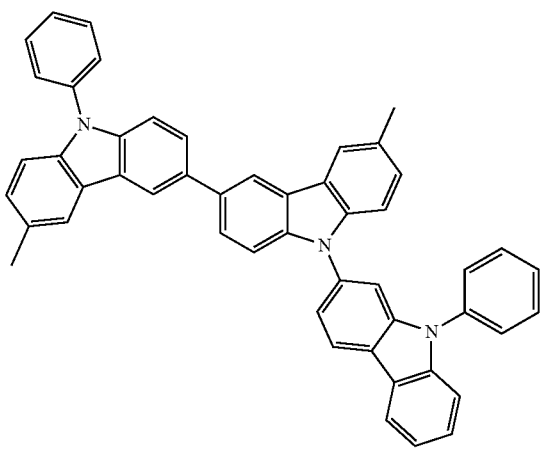

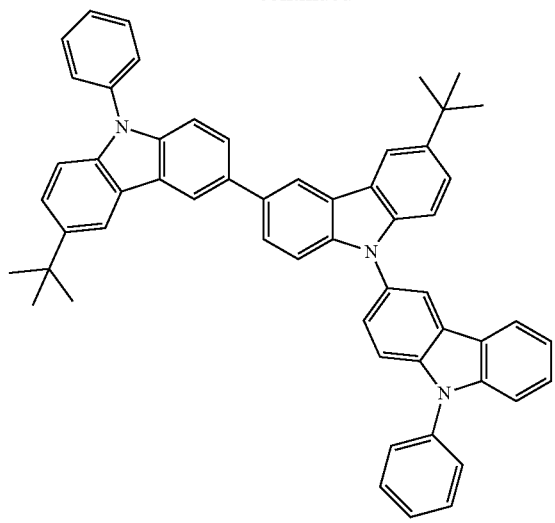
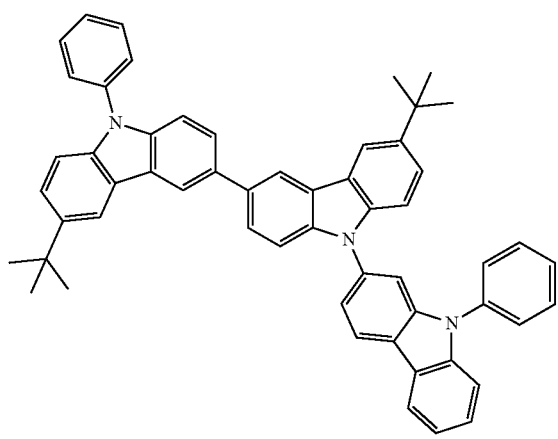
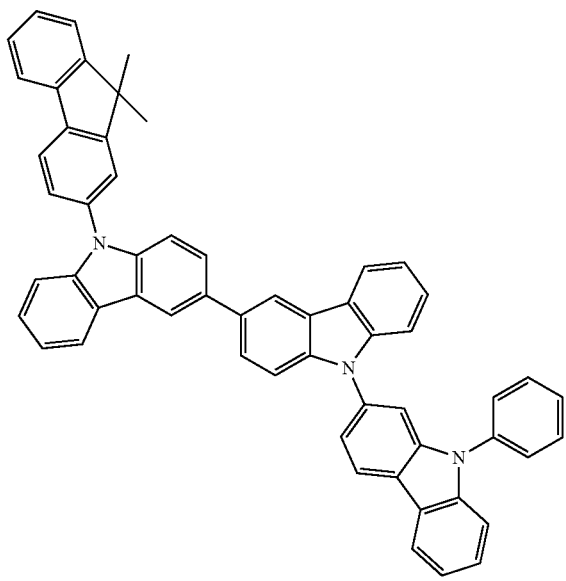

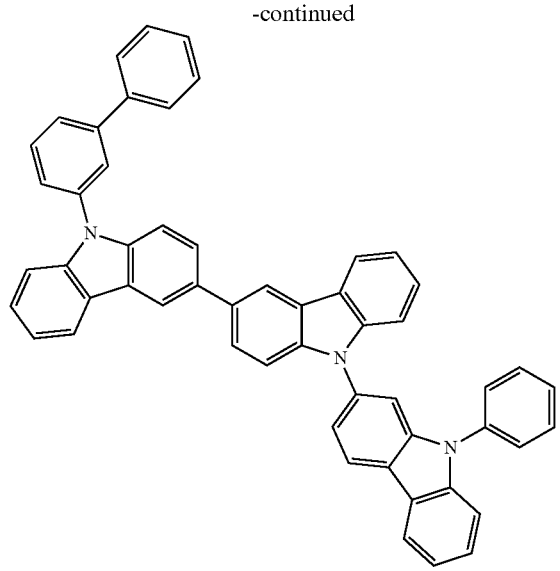
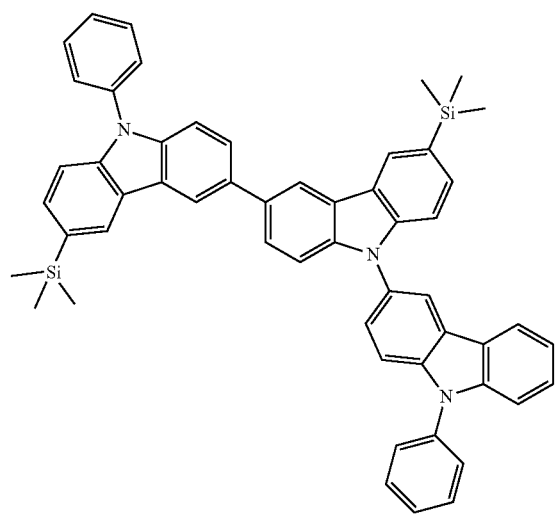
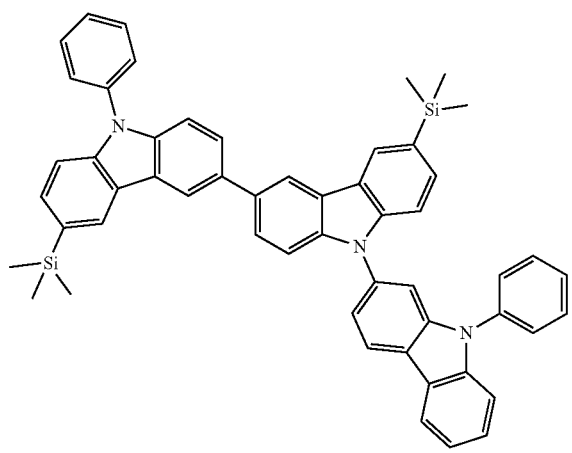

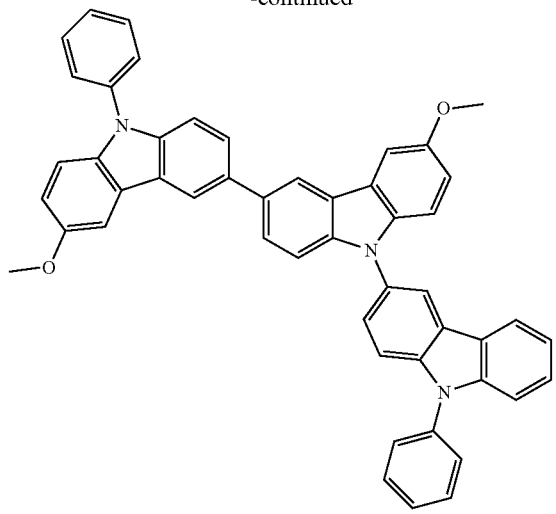
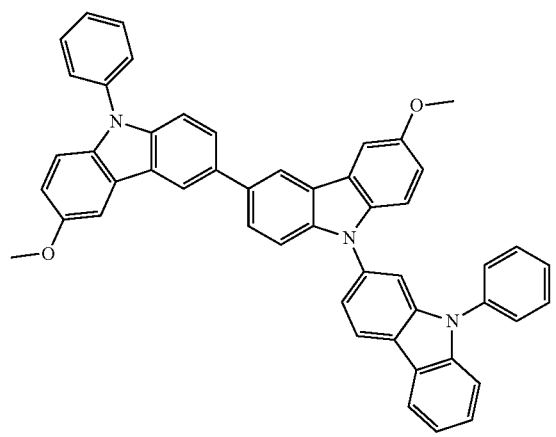
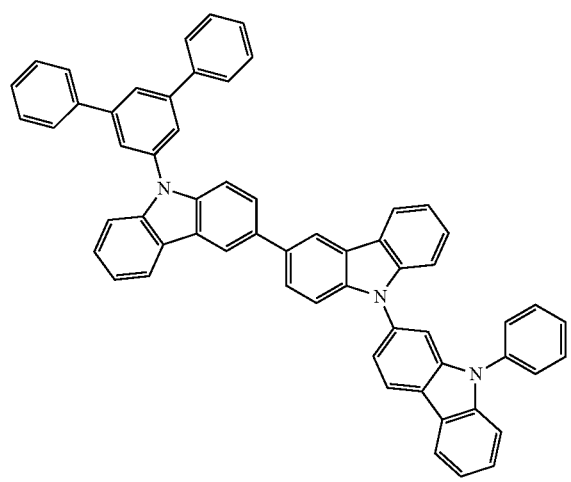

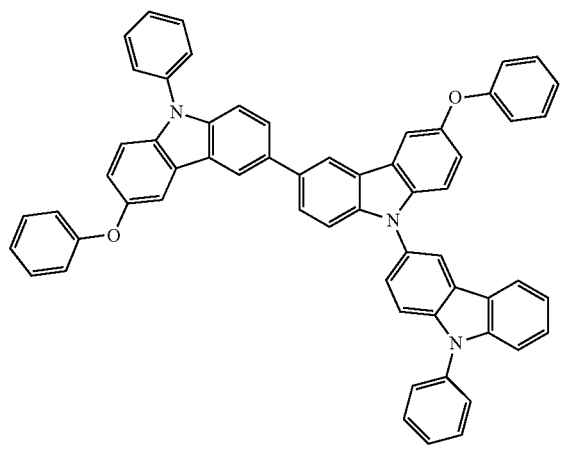
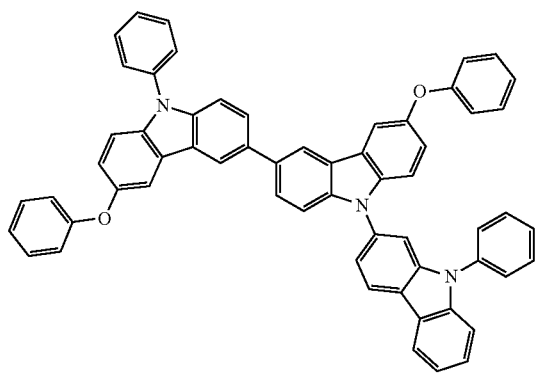
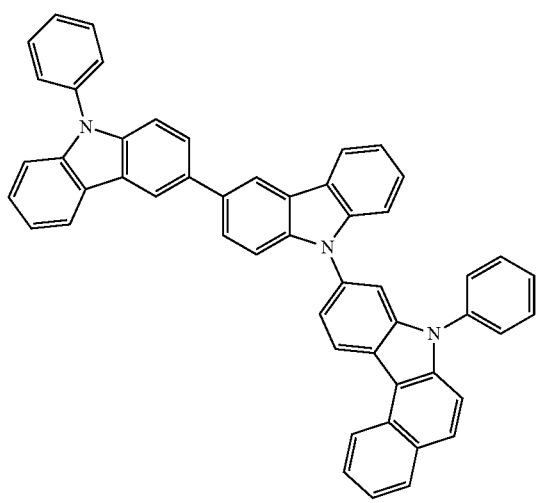

-continued
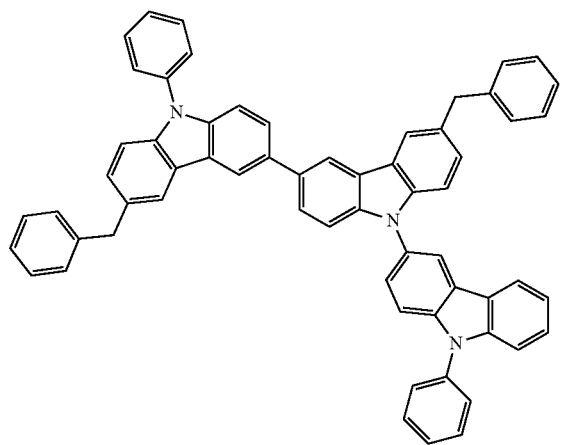
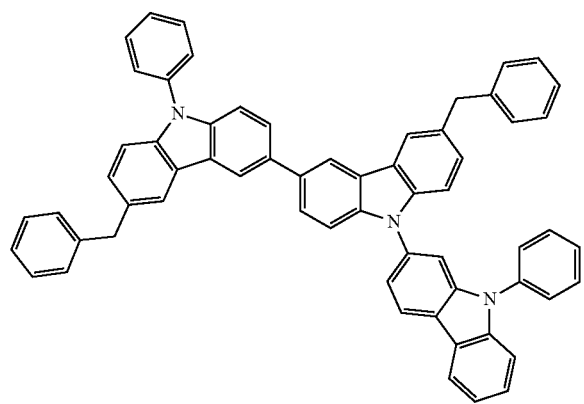
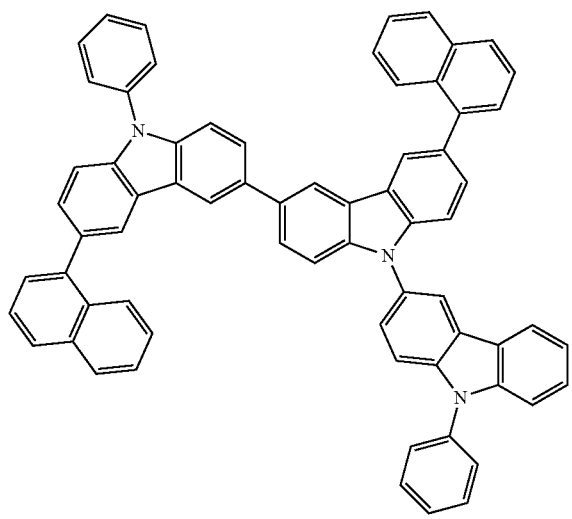

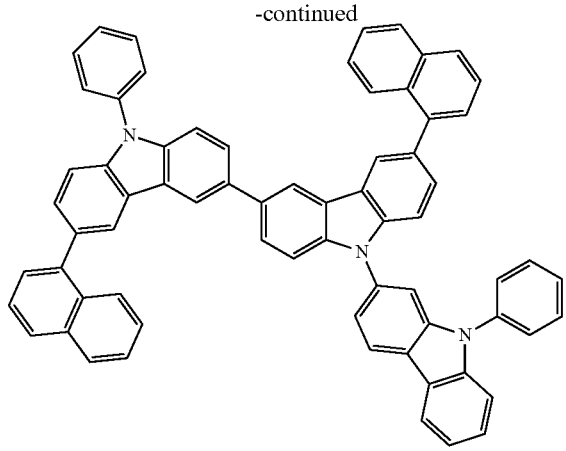
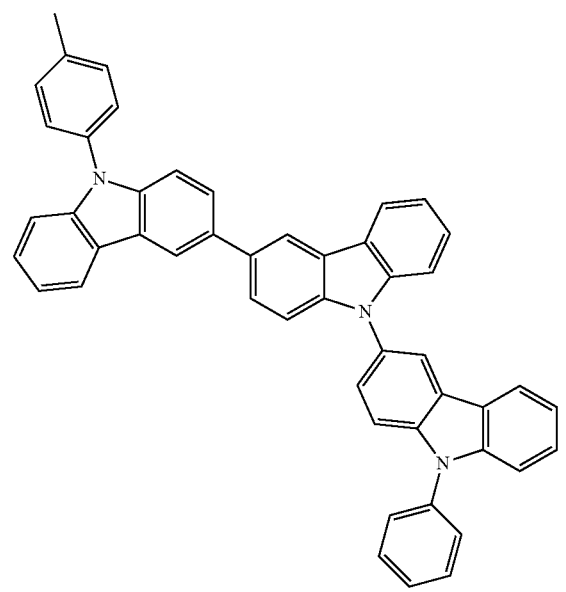
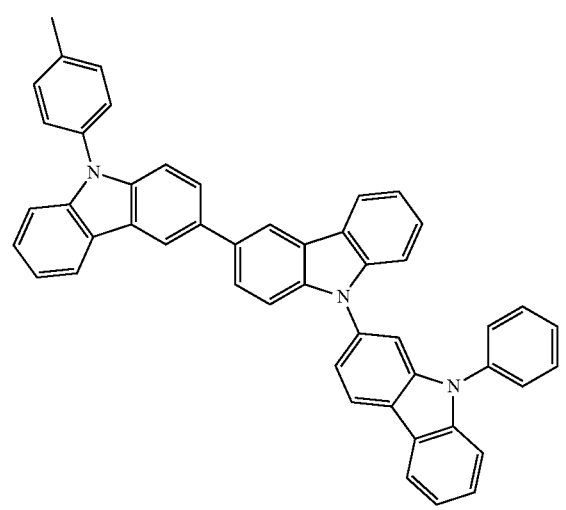

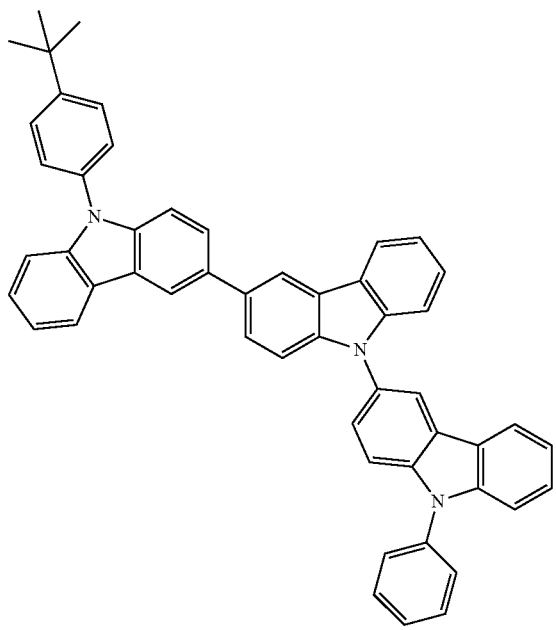
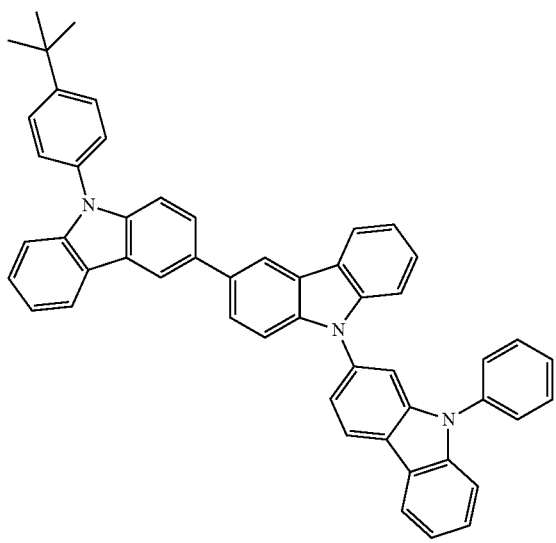

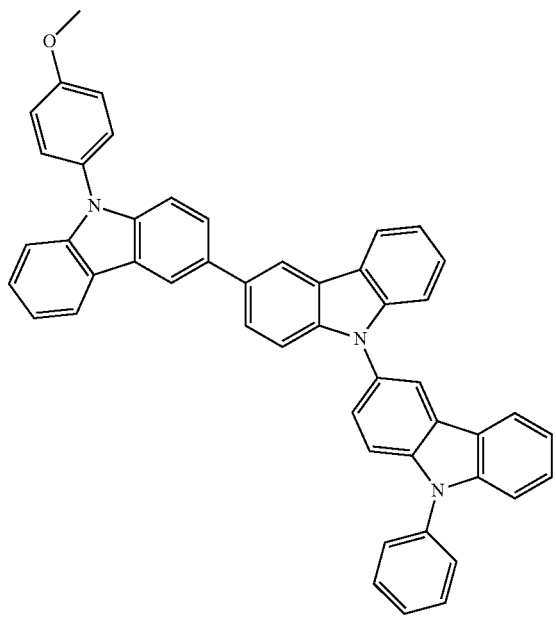
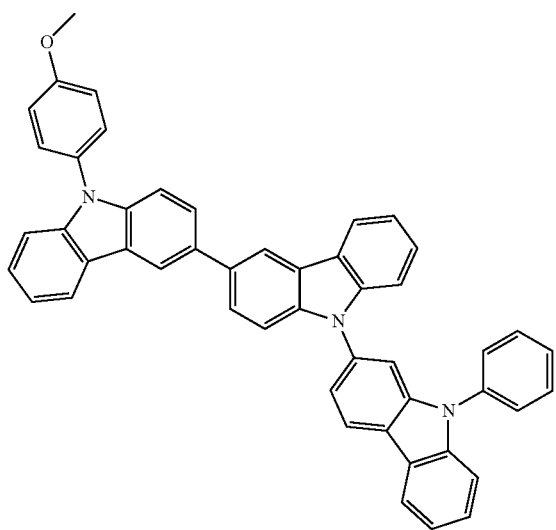

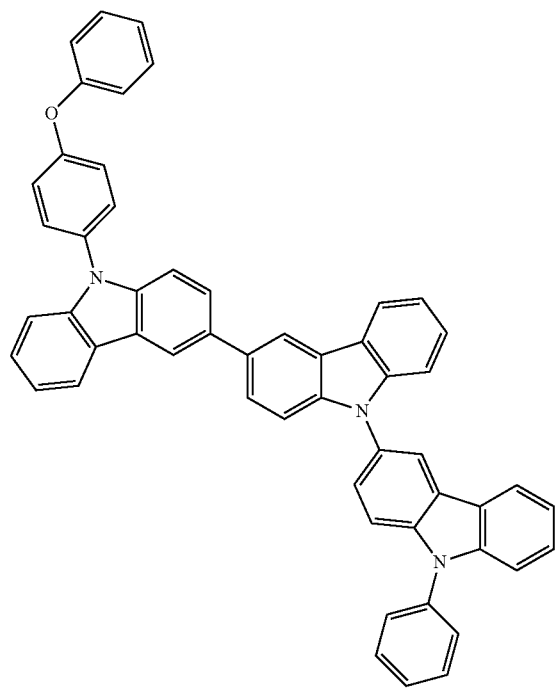
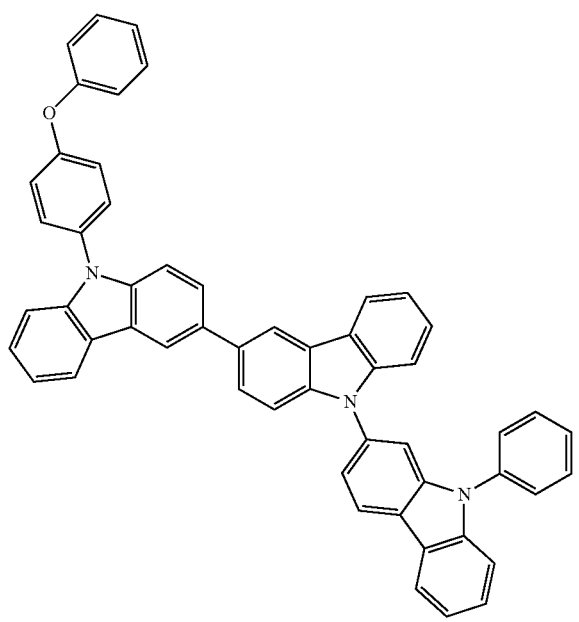

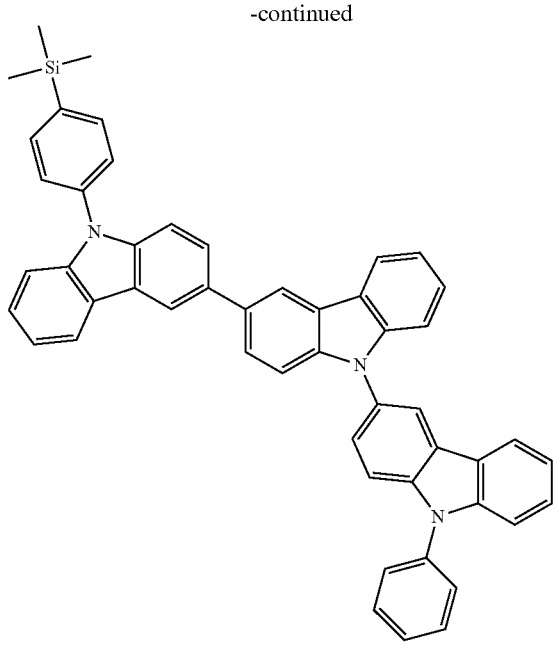
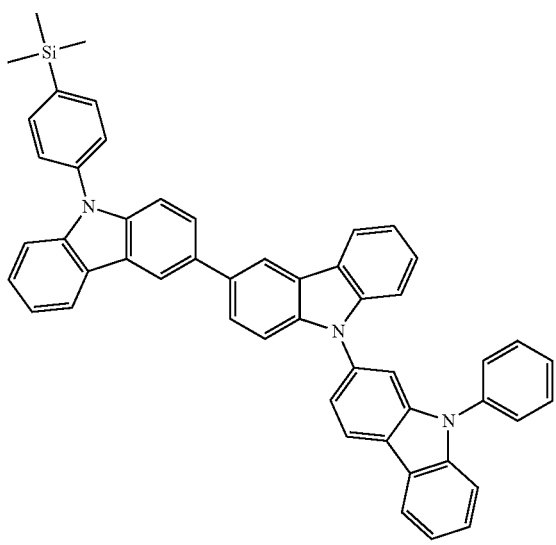
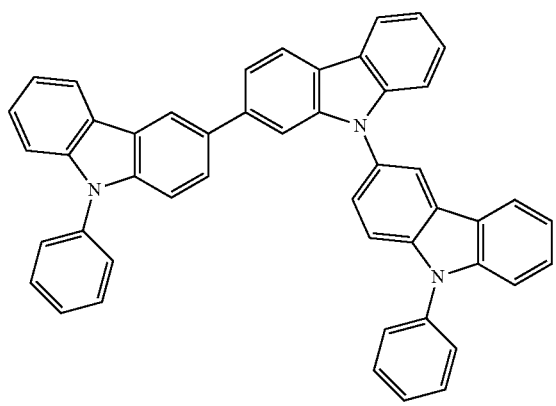

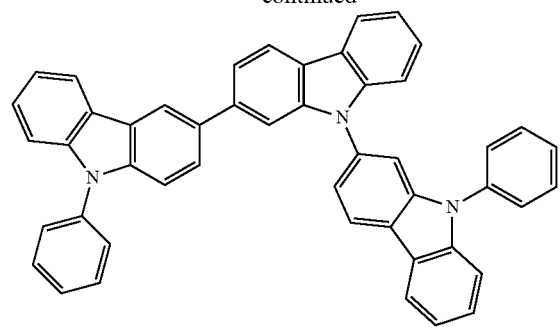
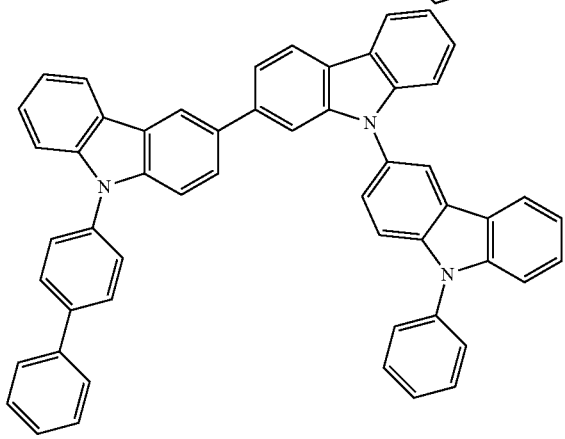
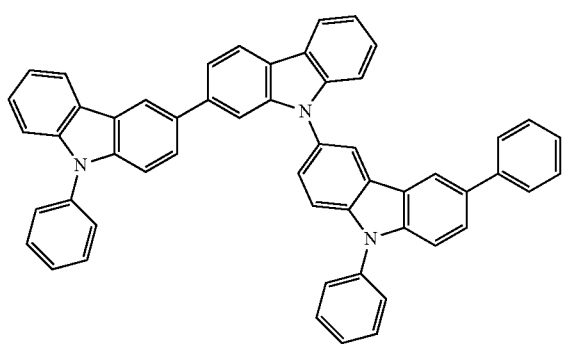
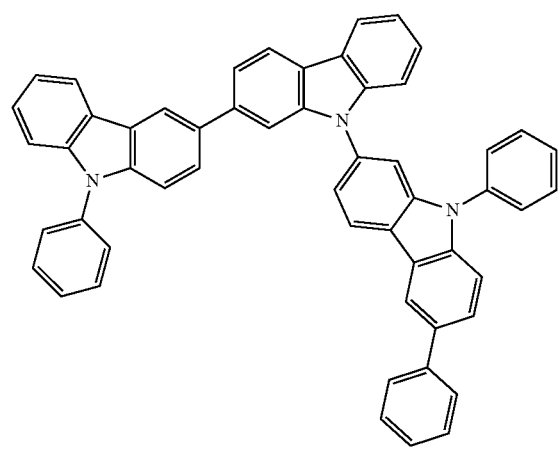

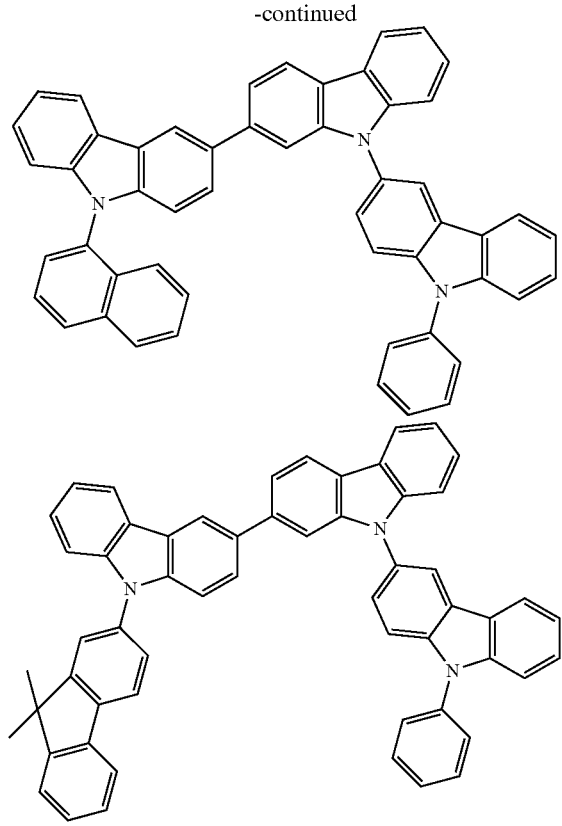
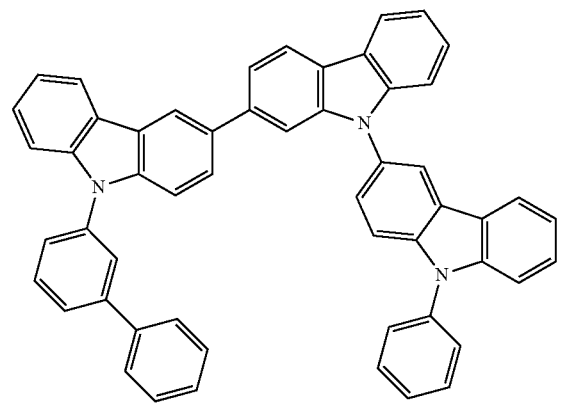
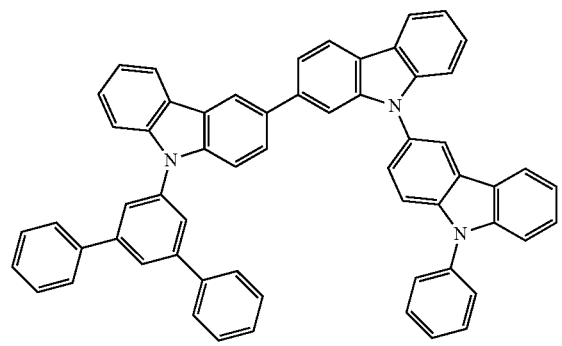

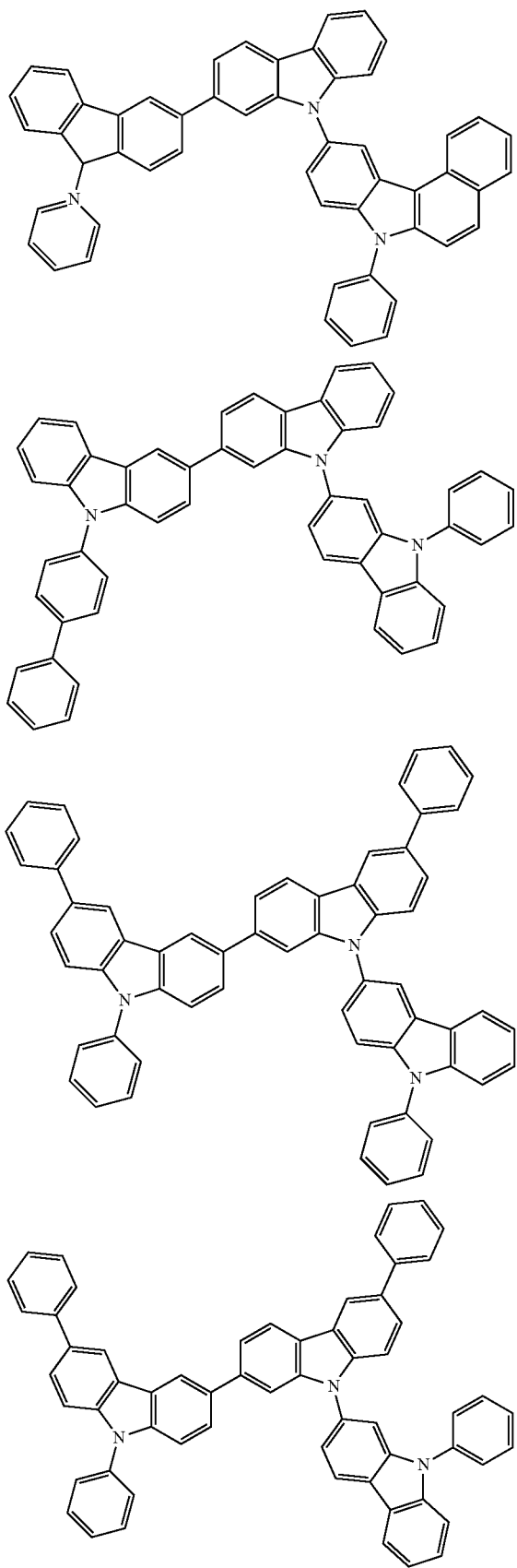

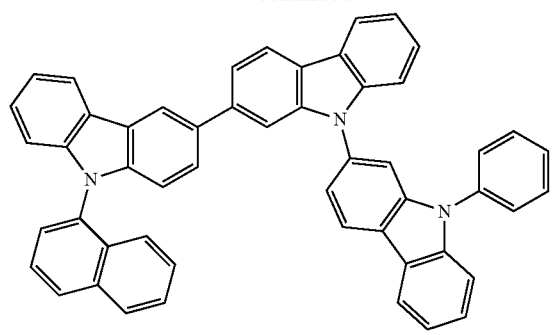
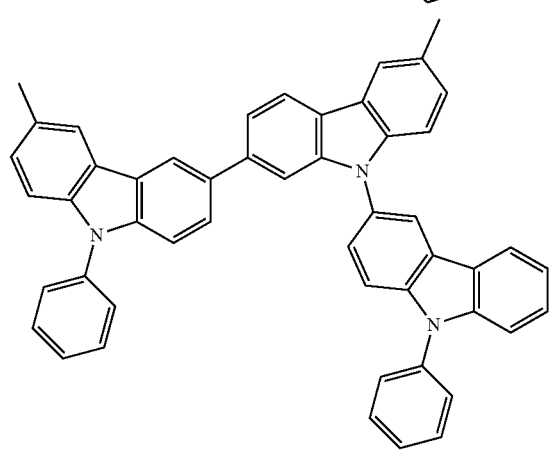
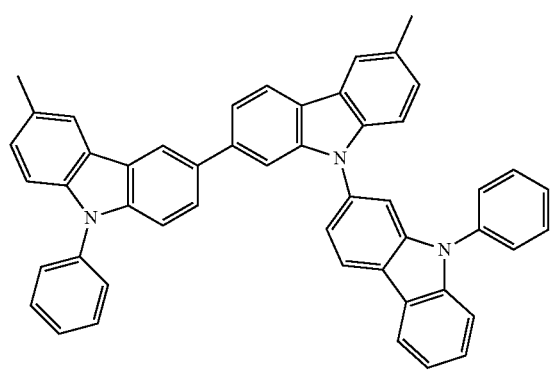
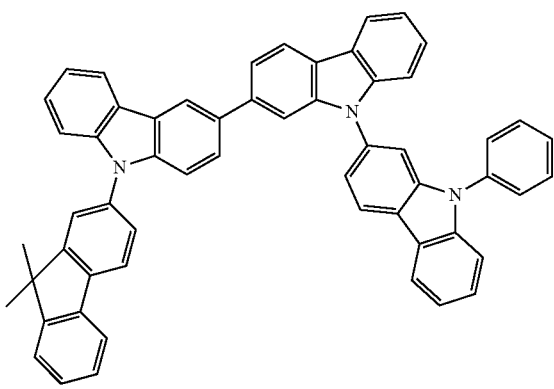

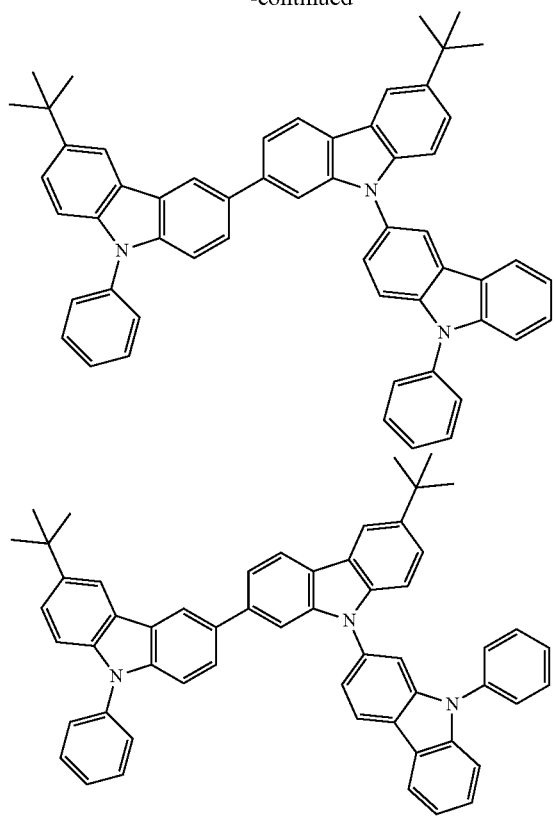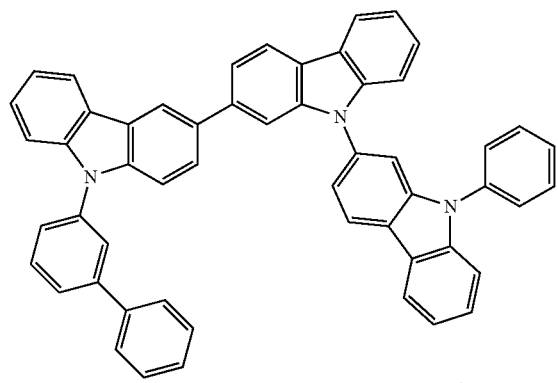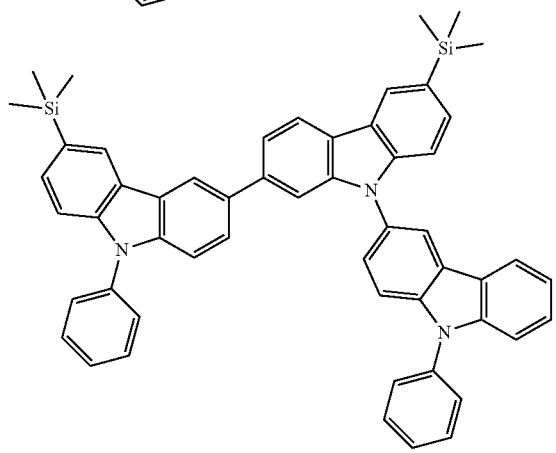

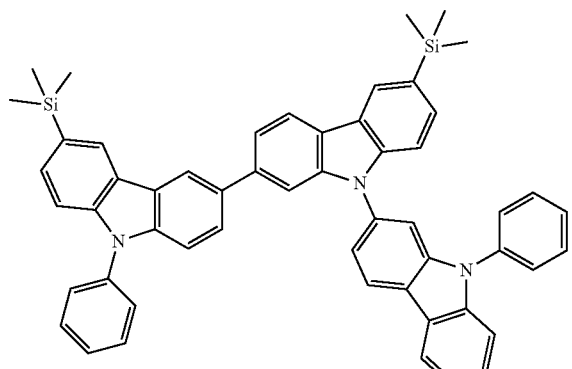
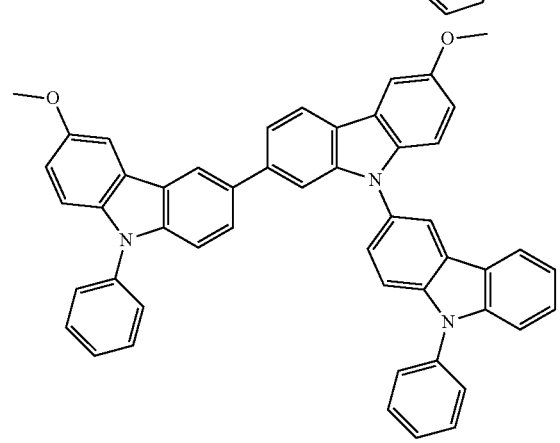
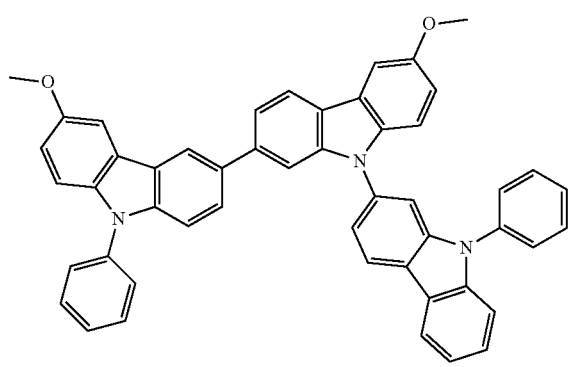
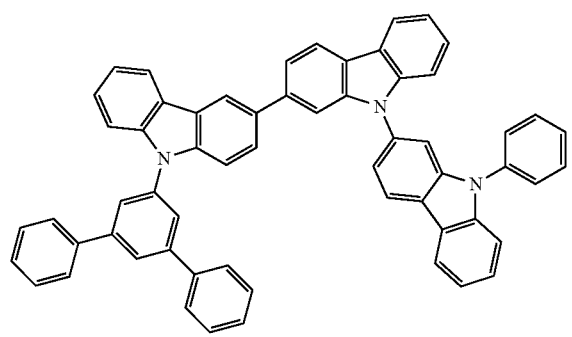

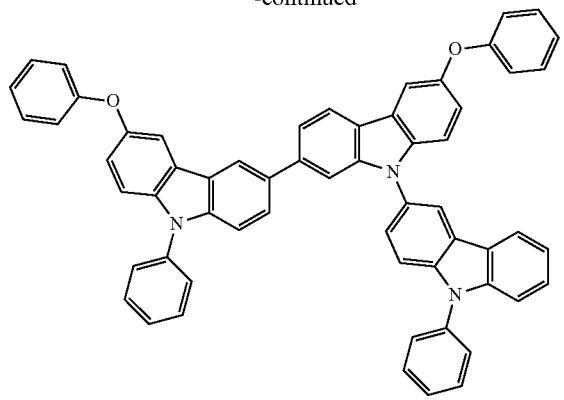
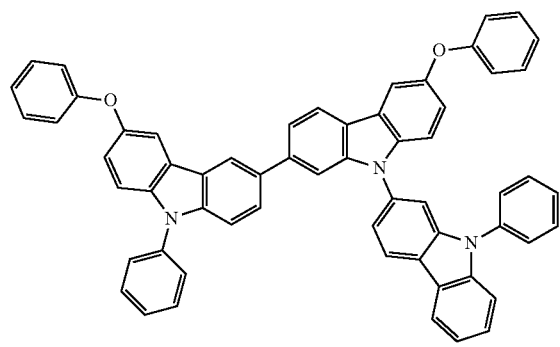
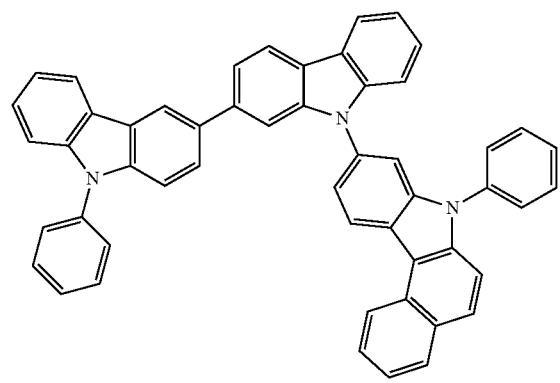
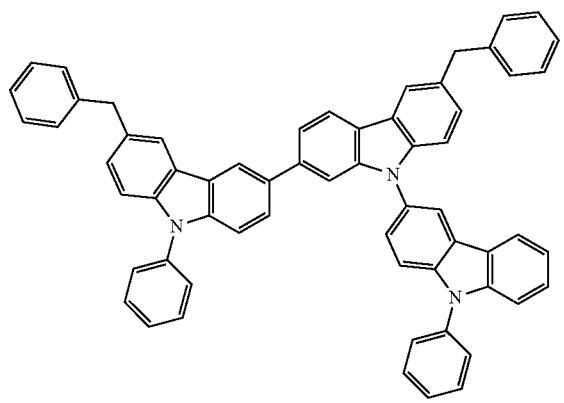

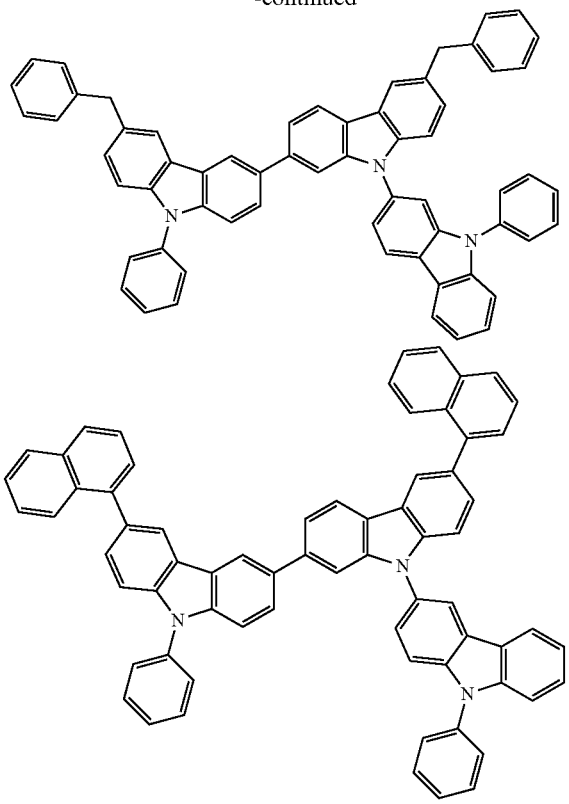
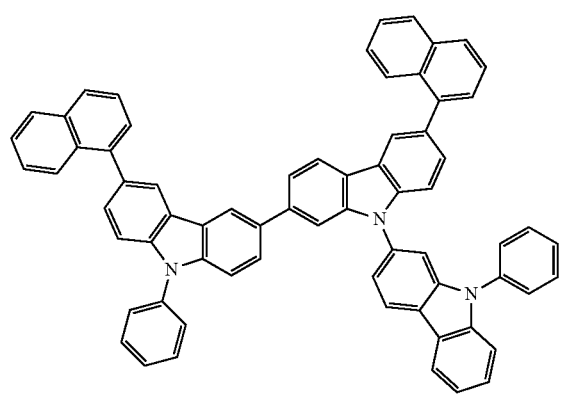
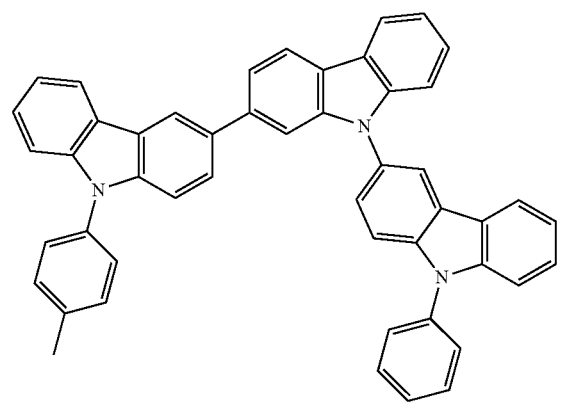

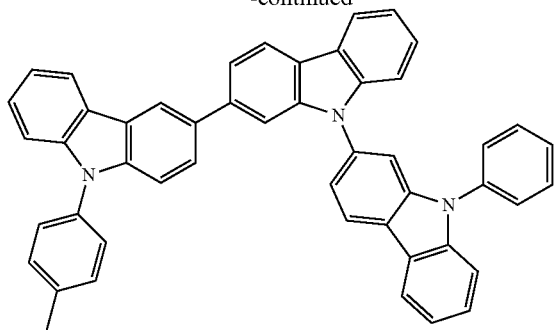
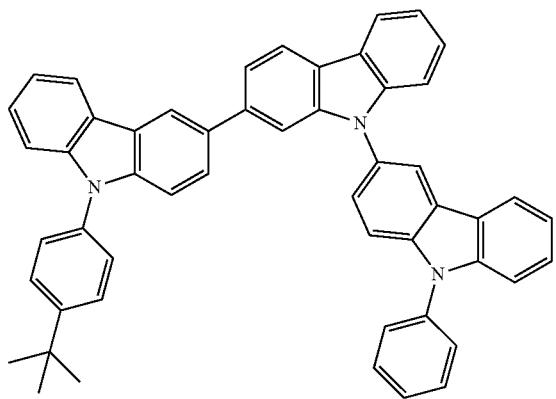
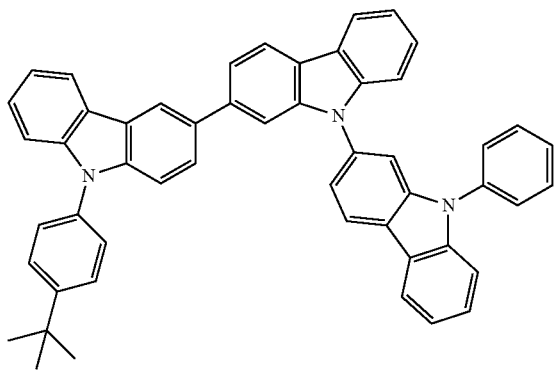
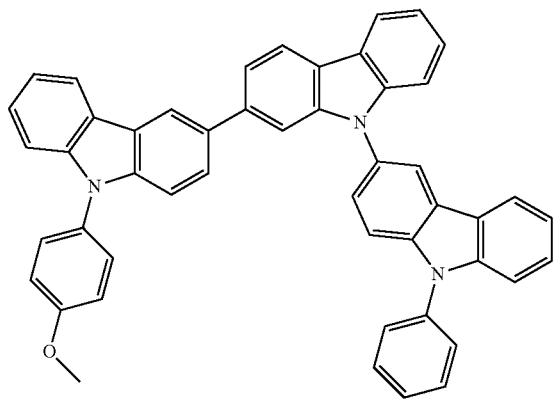

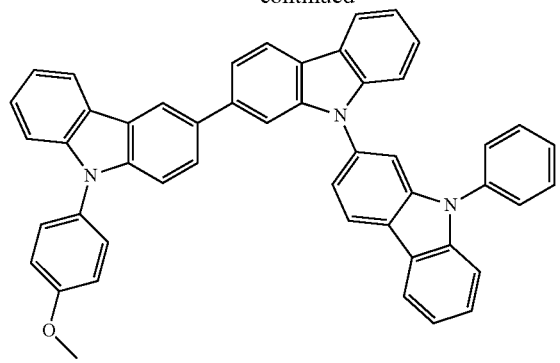
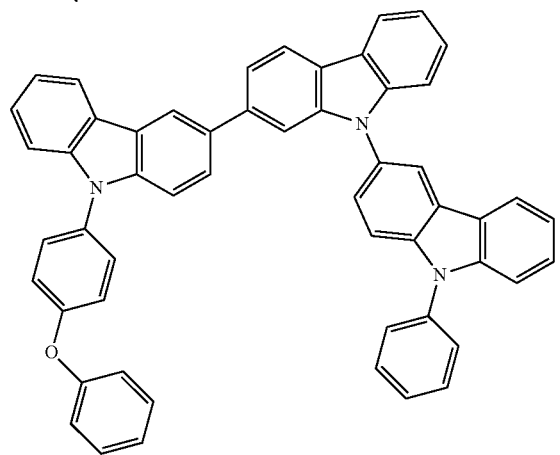
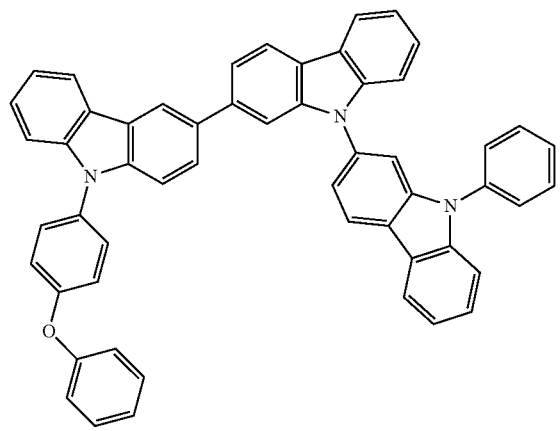
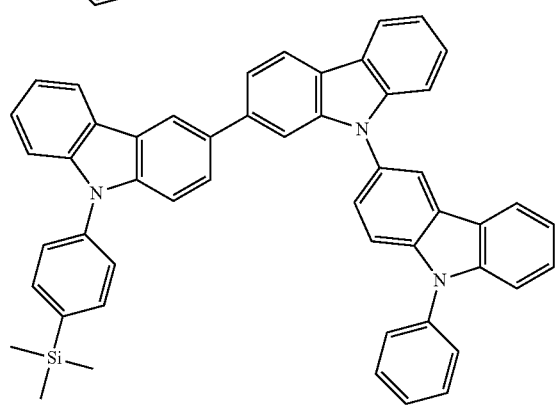

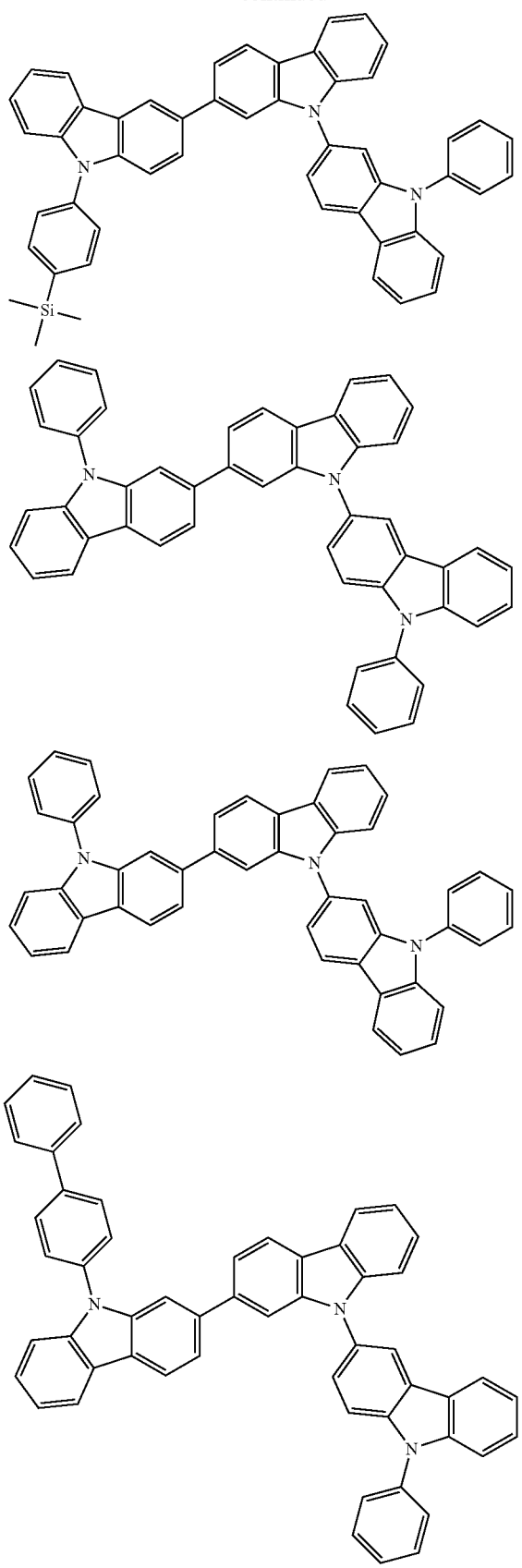

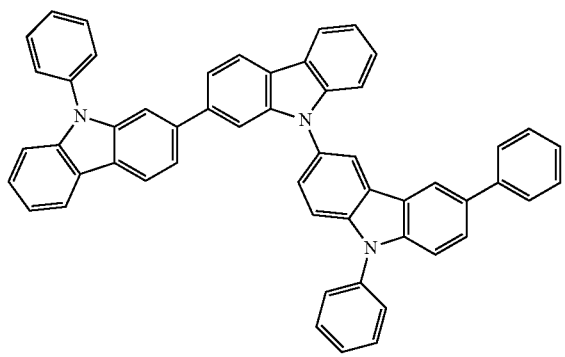
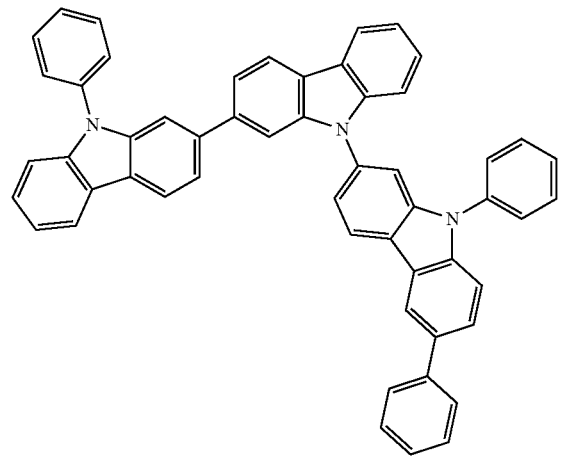
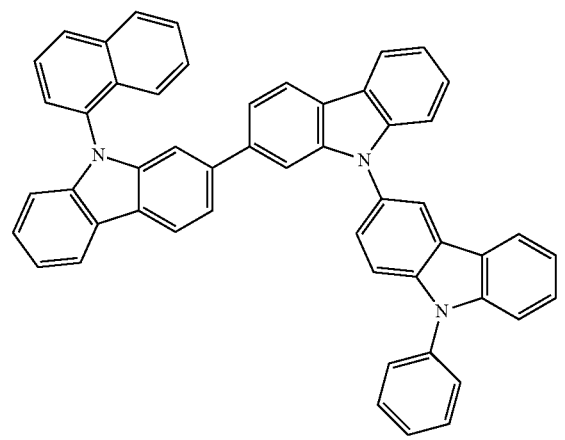

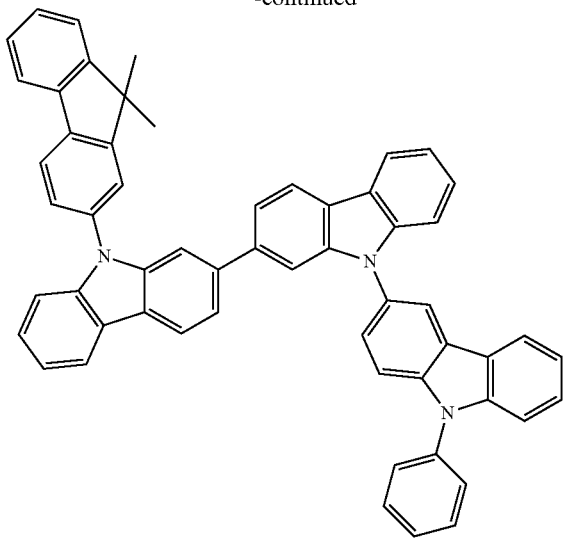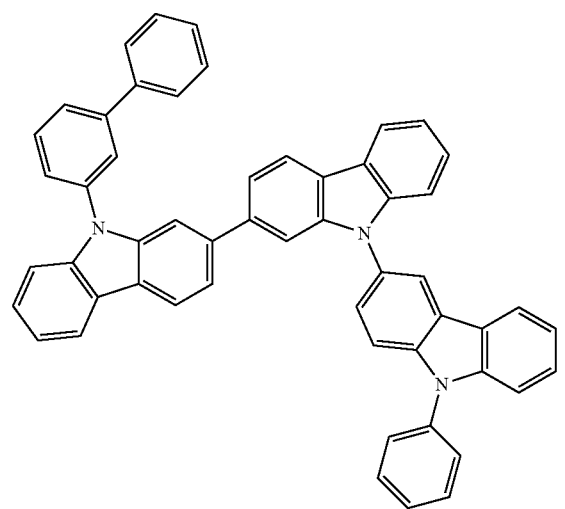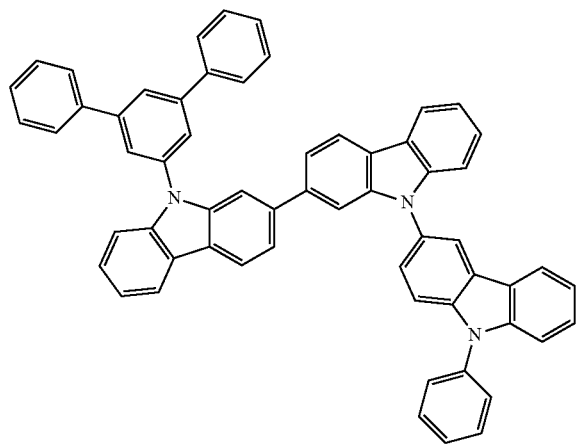

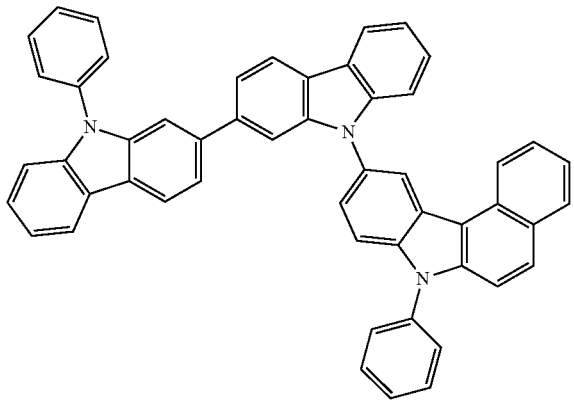
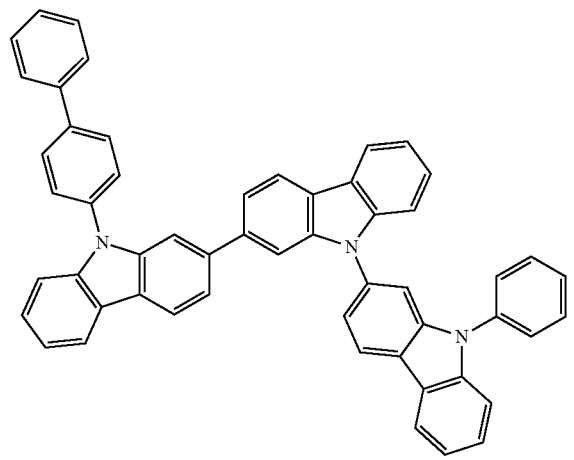
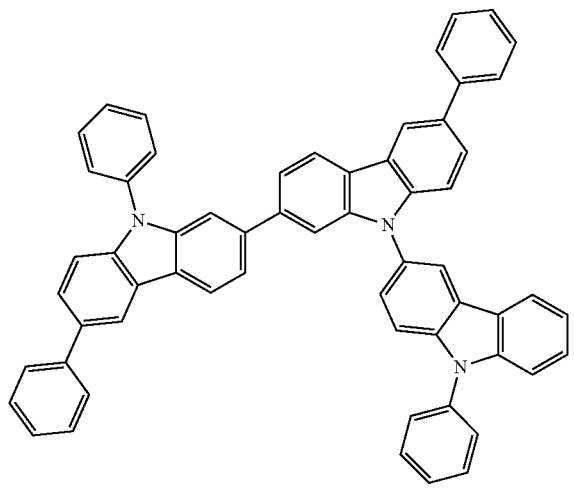

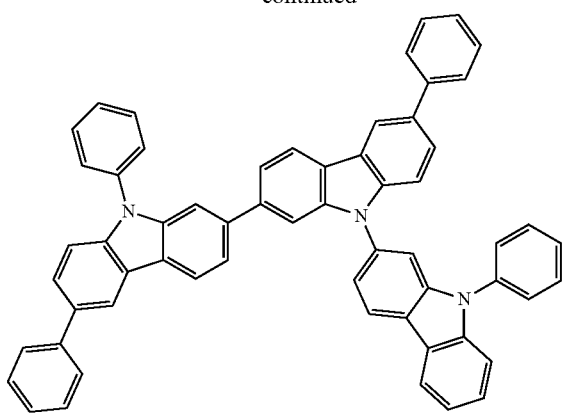
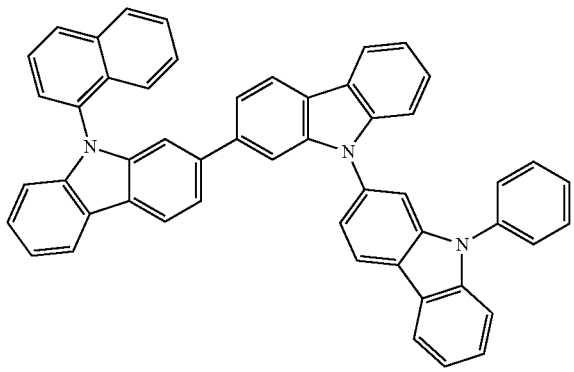
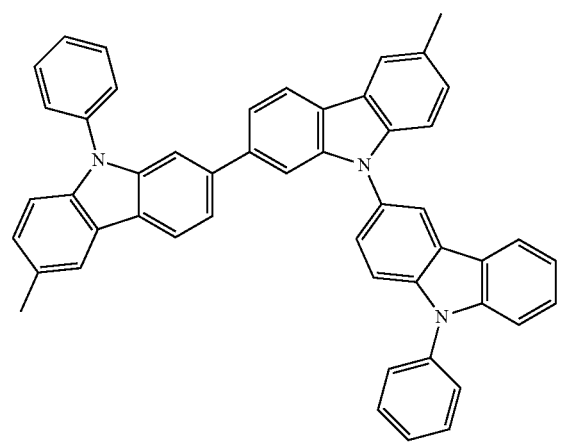
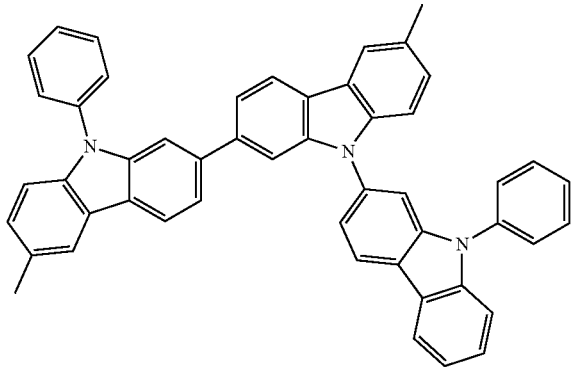

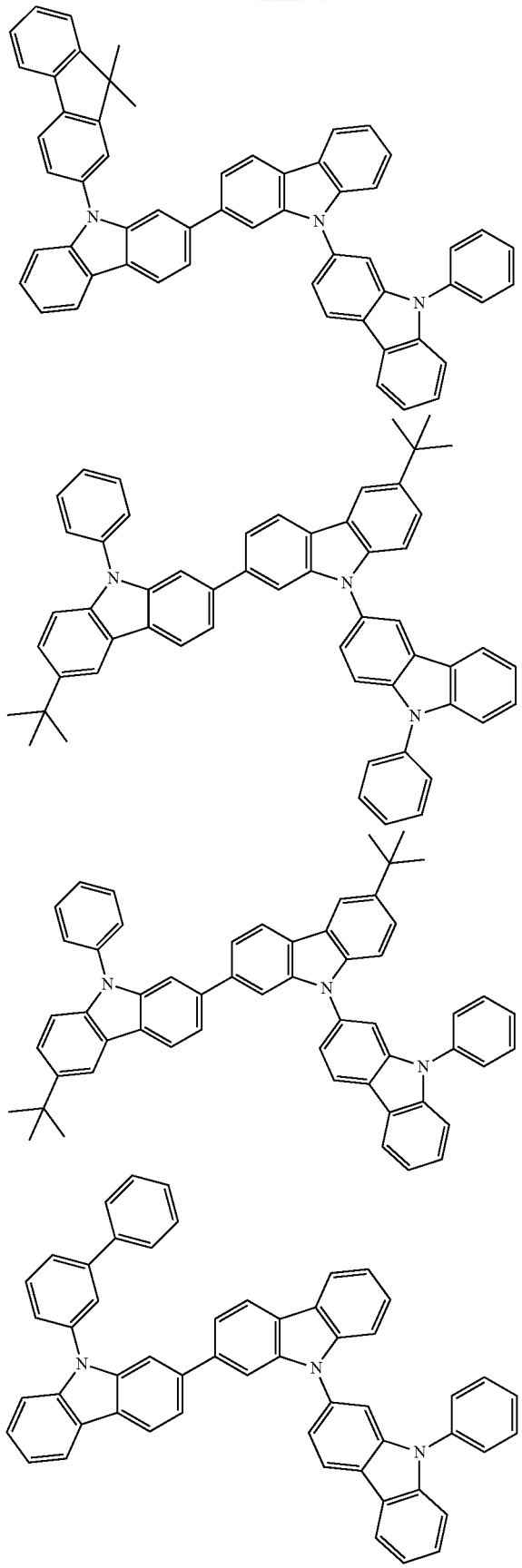

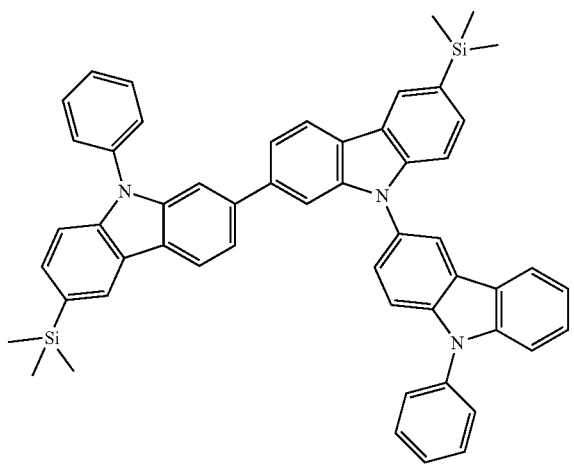
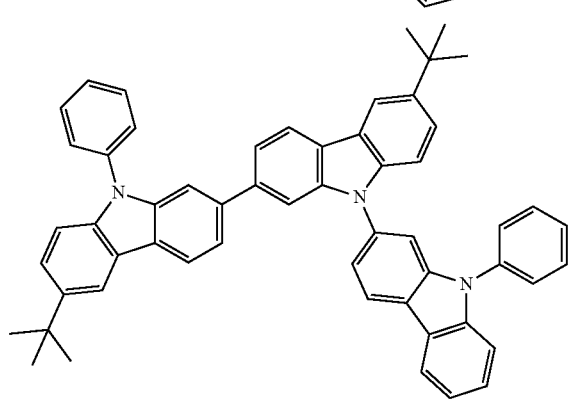
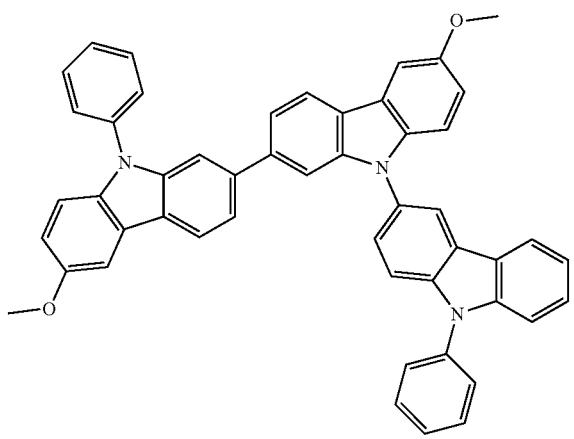
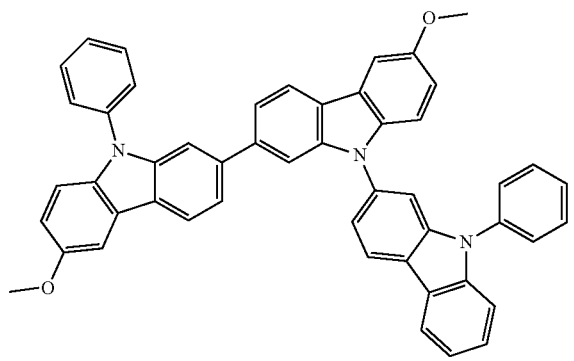

-continued
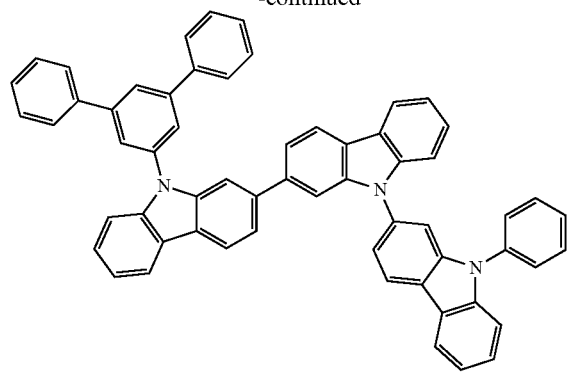
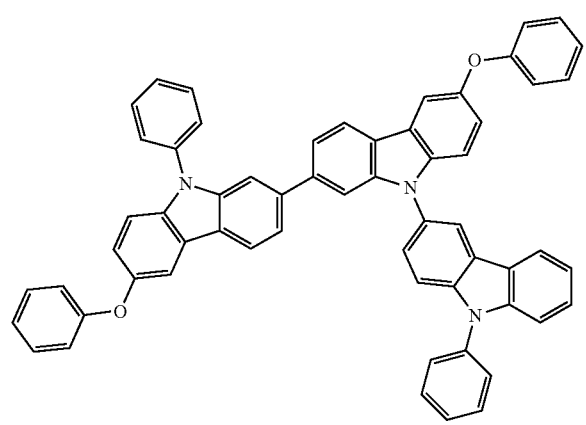
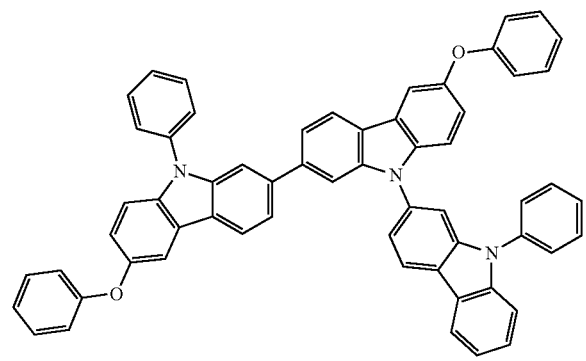
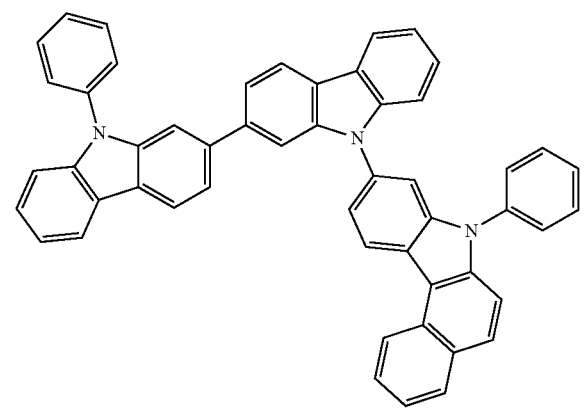

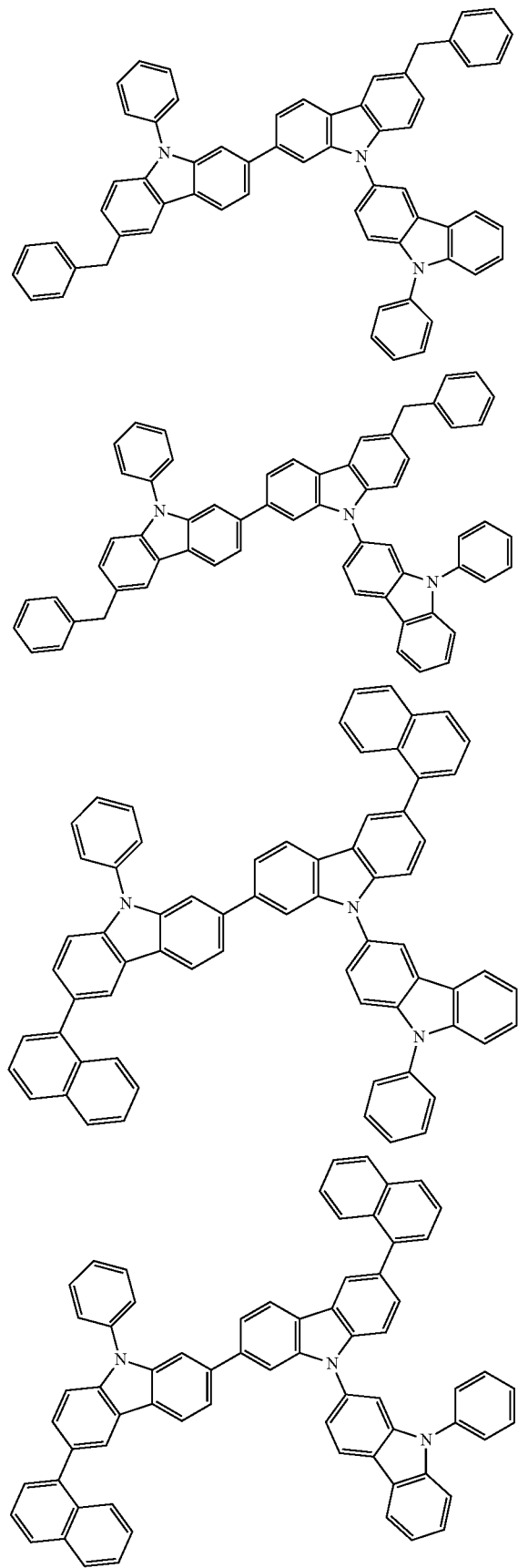

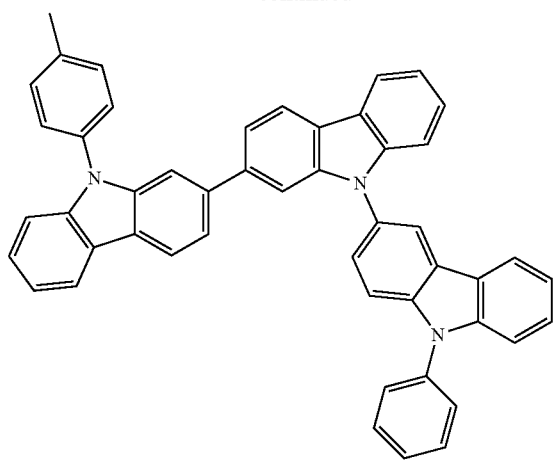
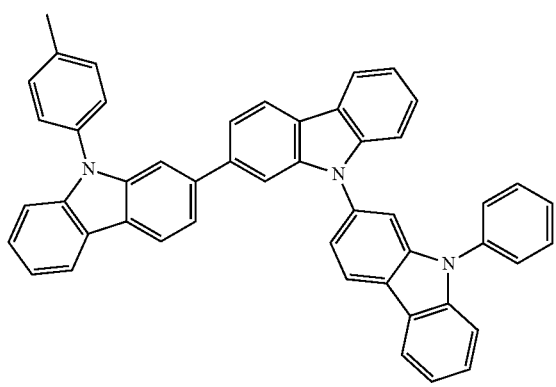
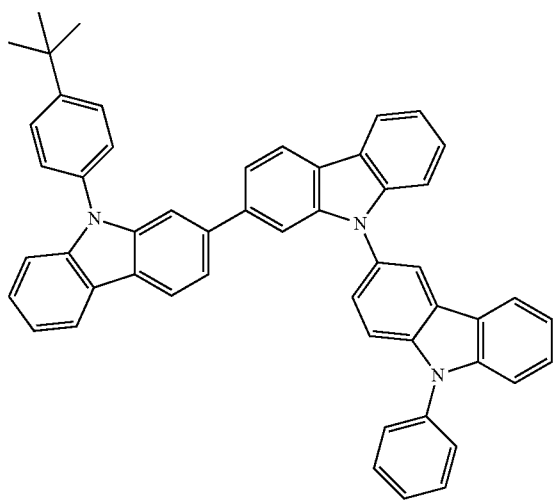

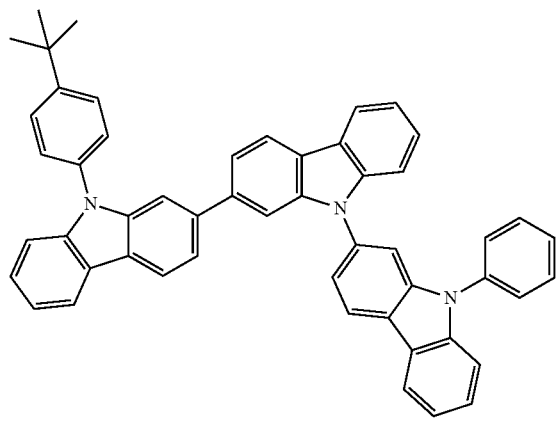
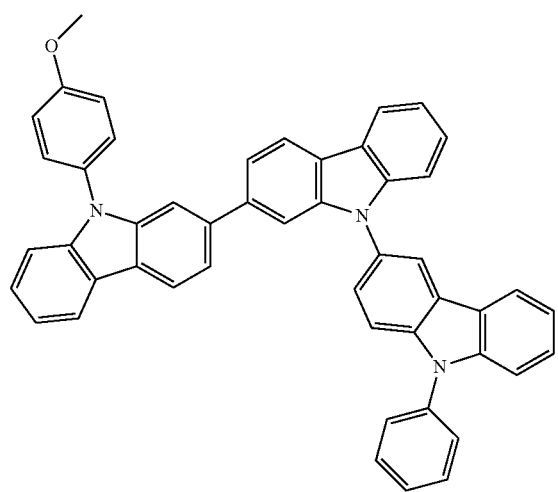
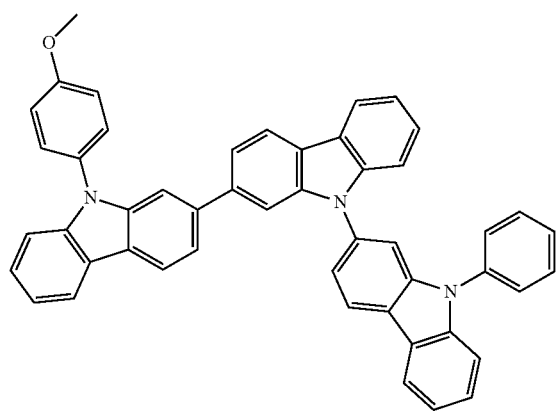

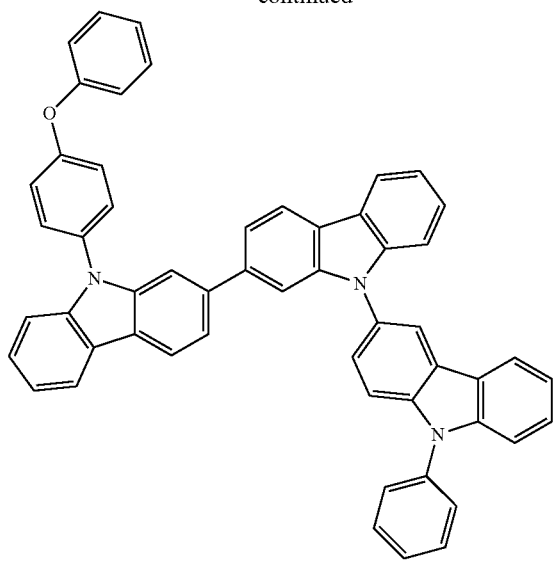
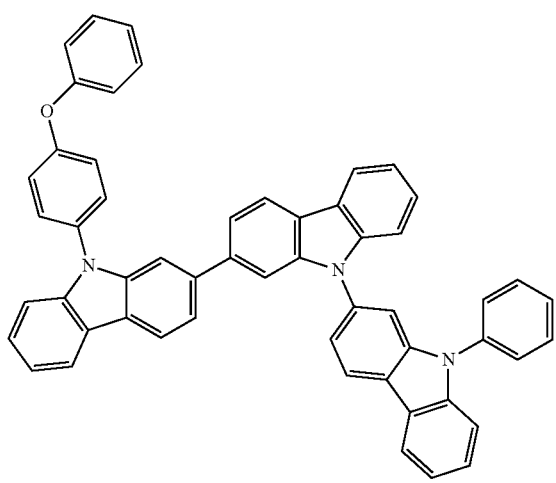
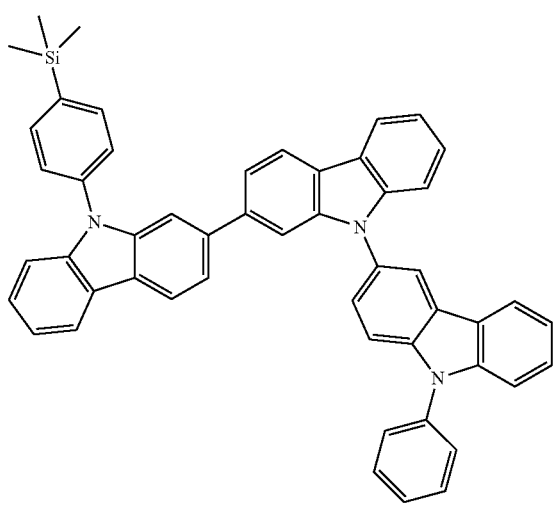

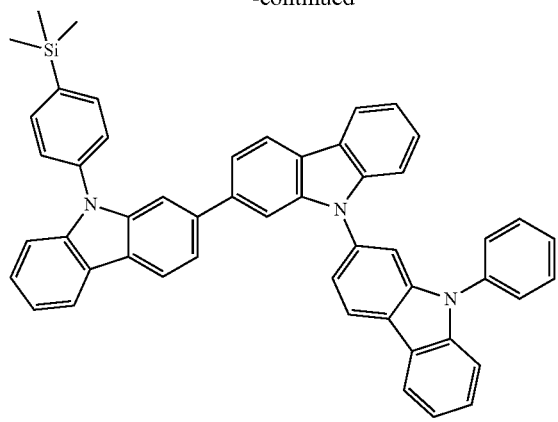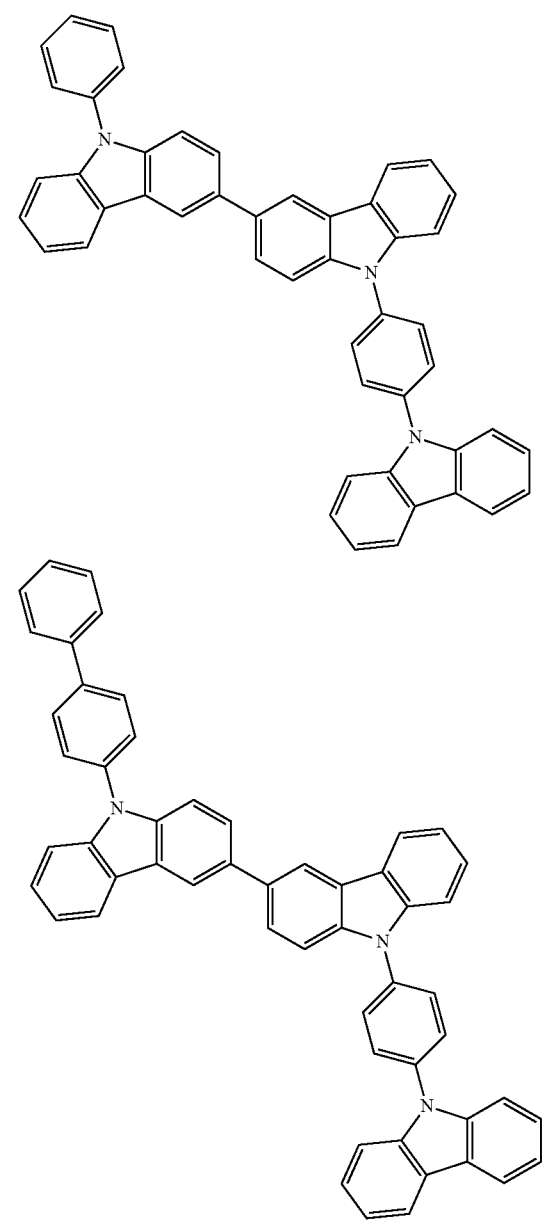

-continued
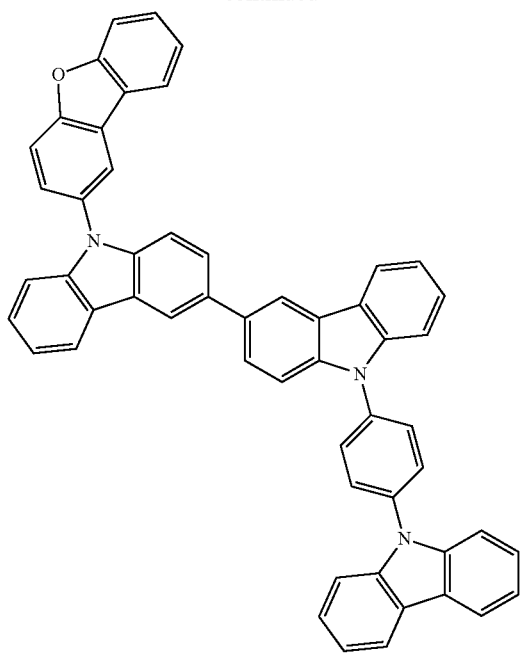
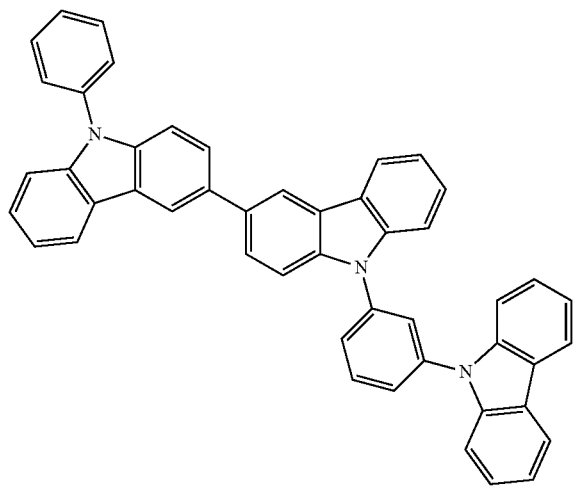
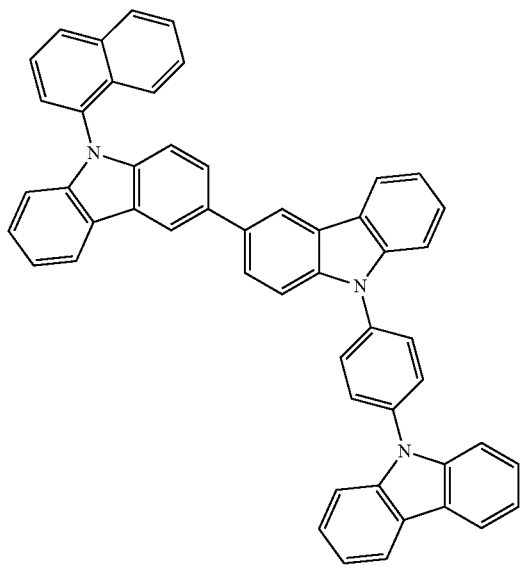

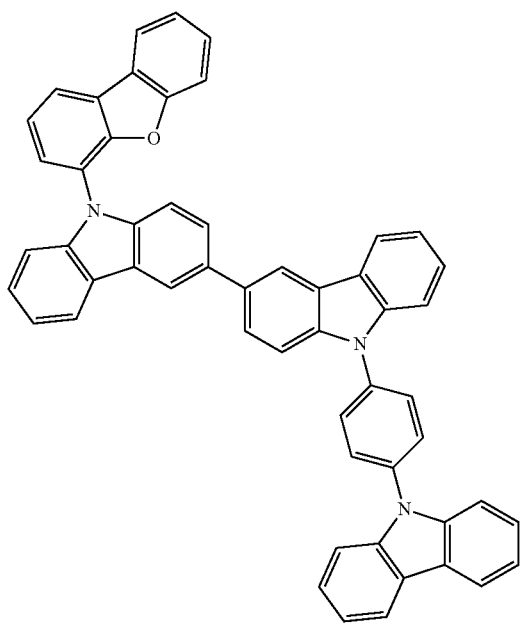
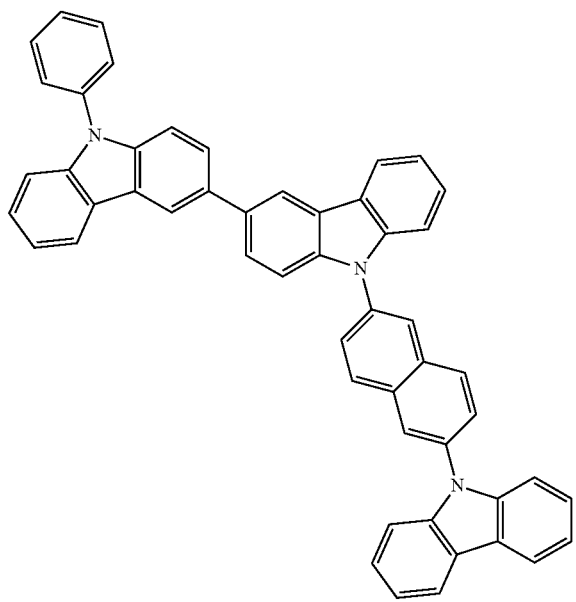

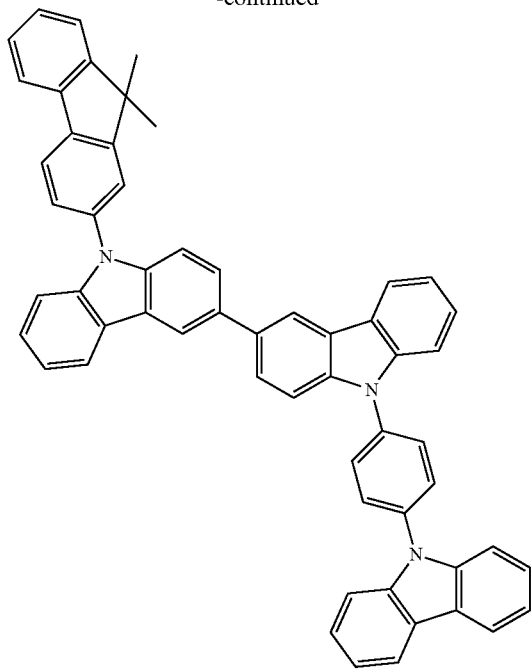
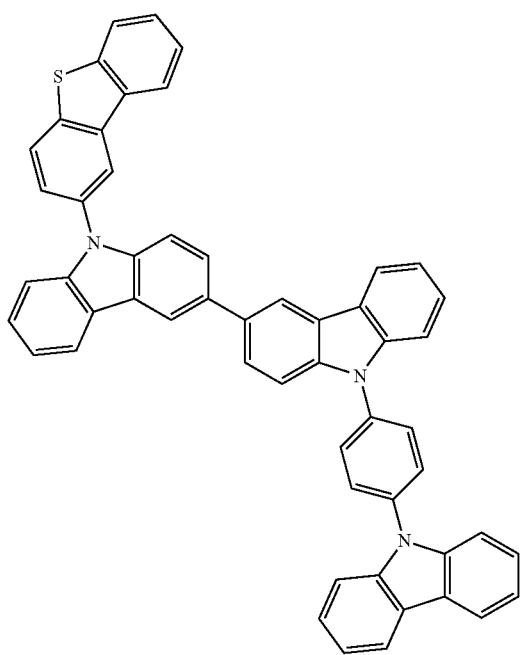

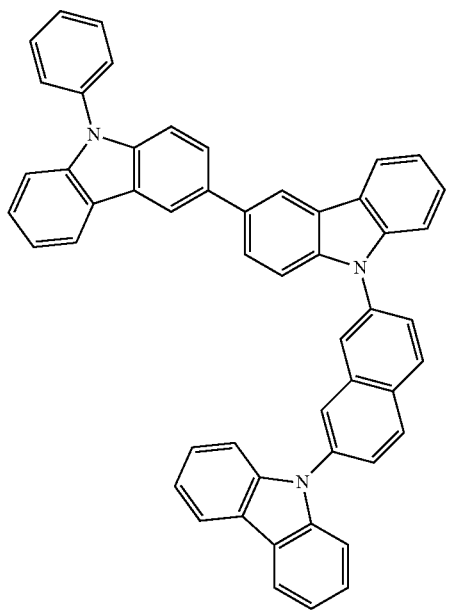
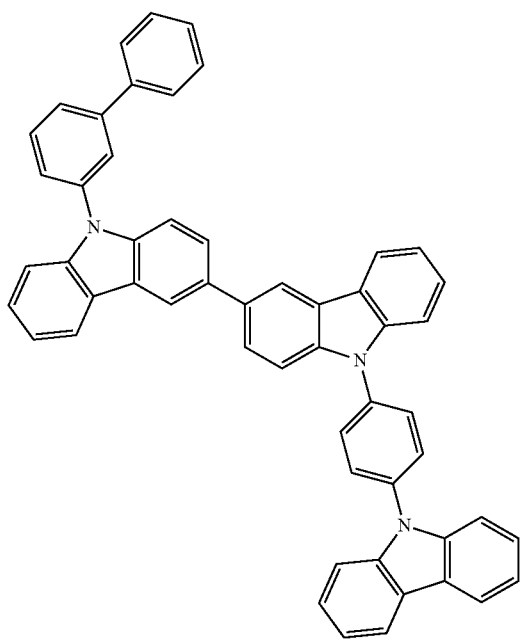

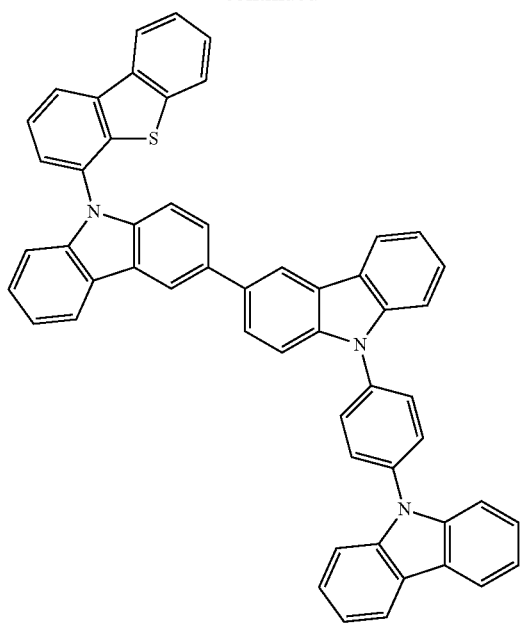
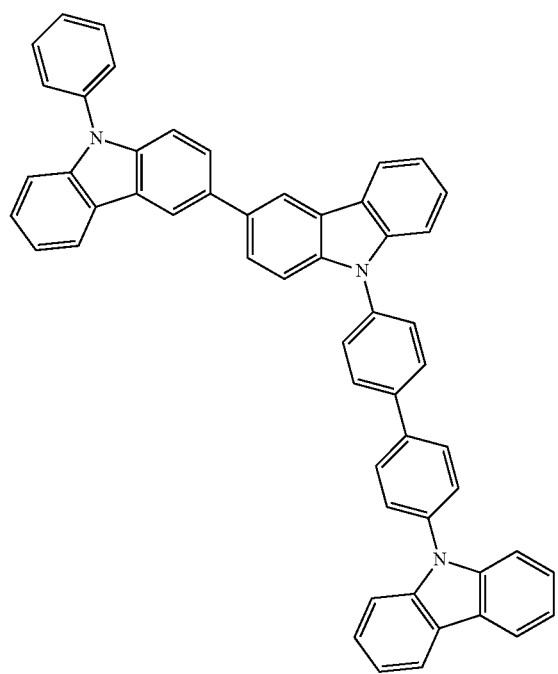

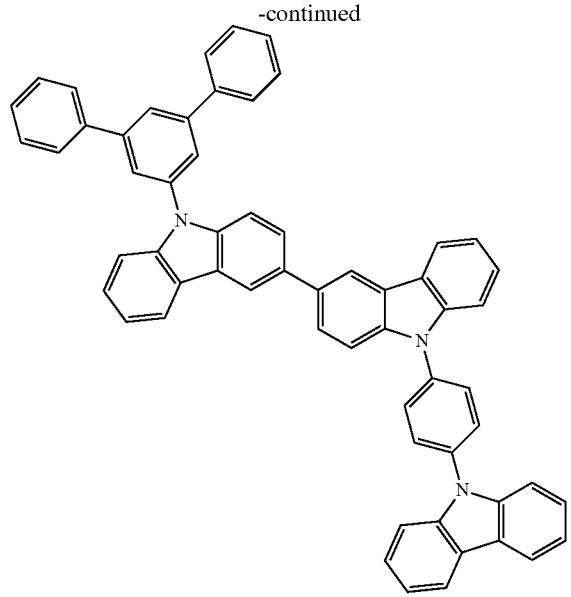
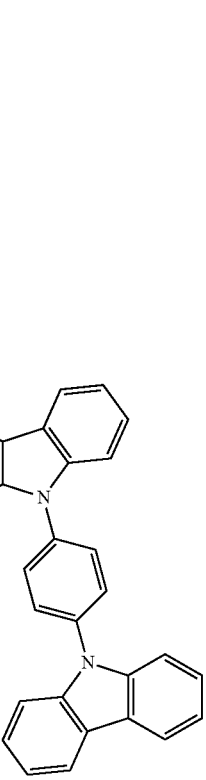

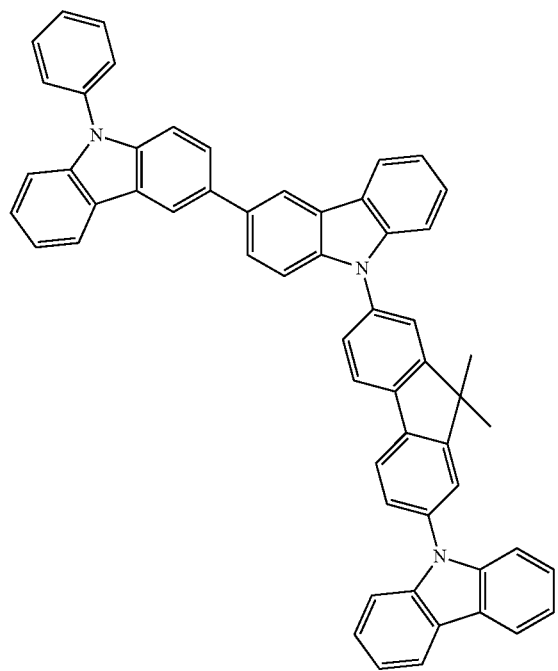
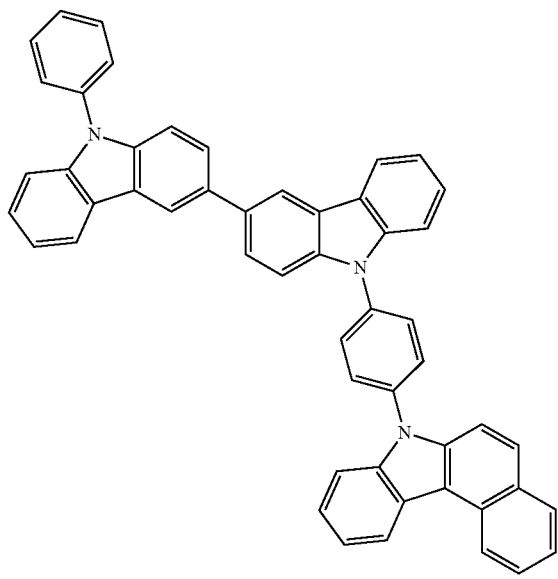

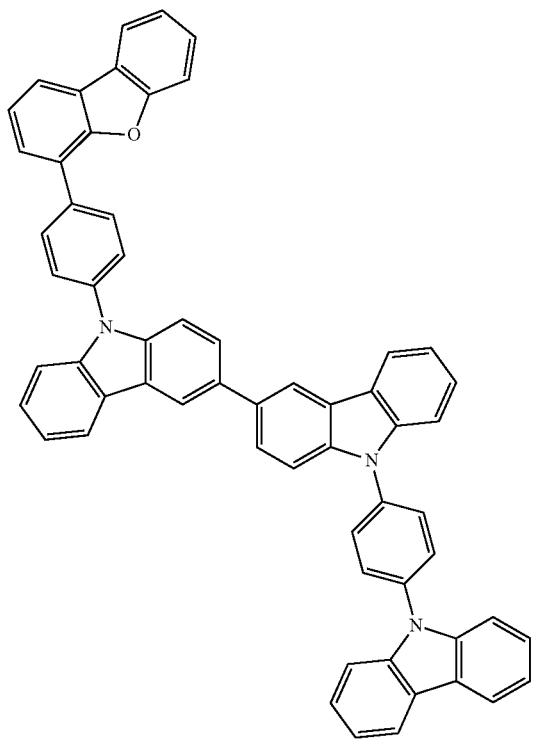
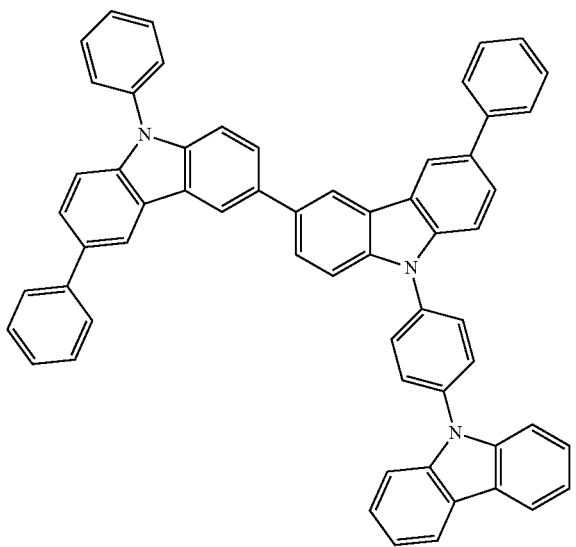

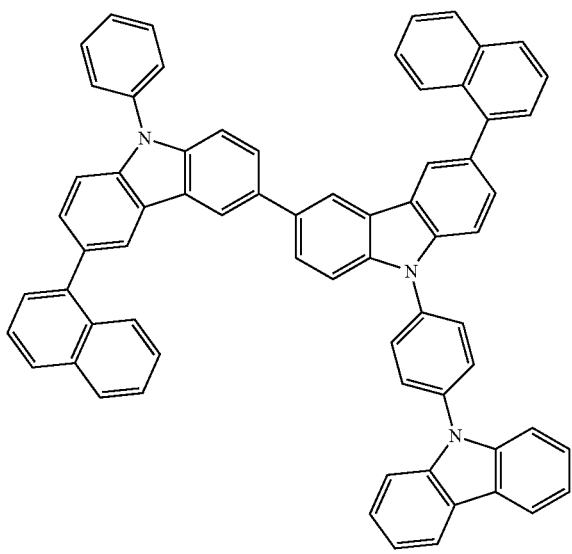
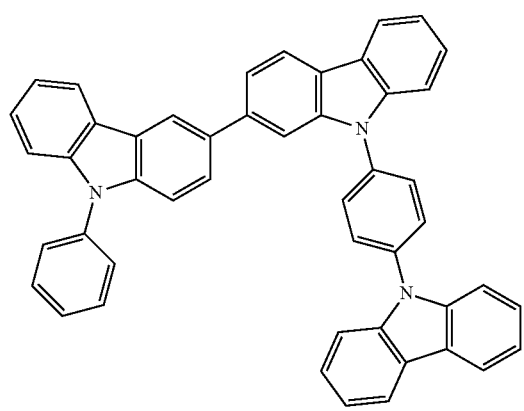
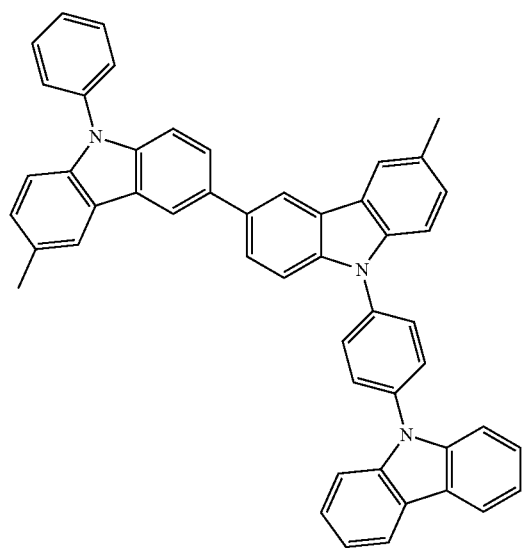

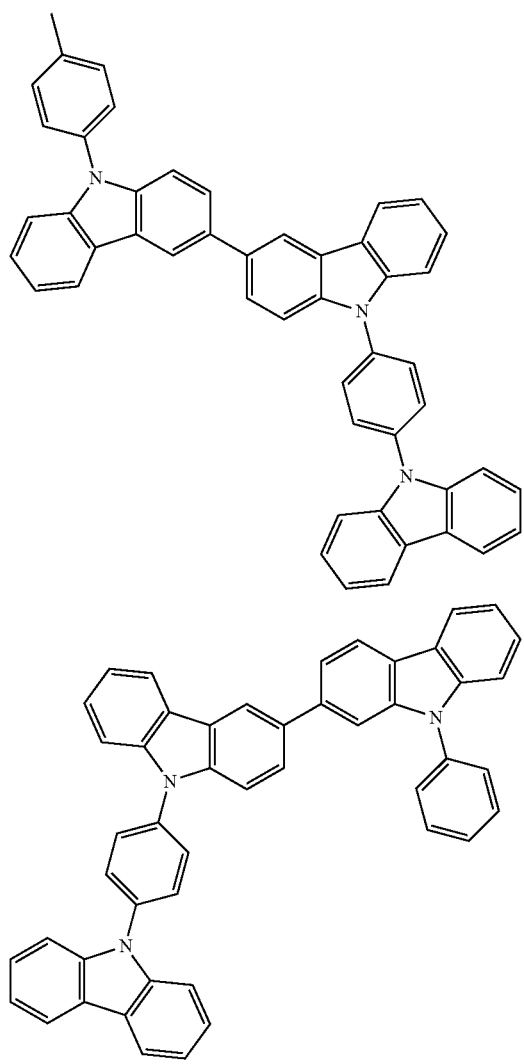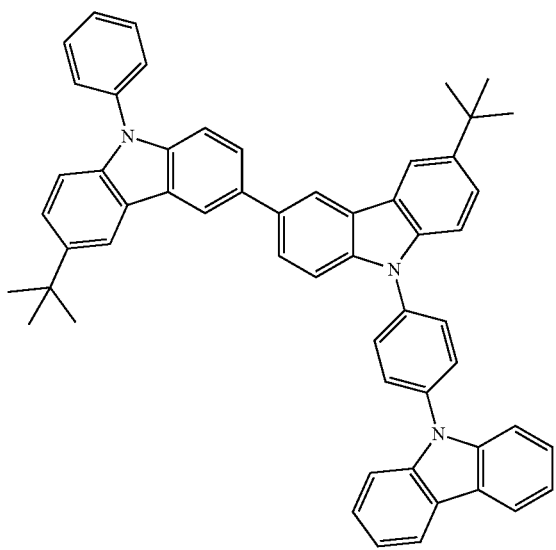

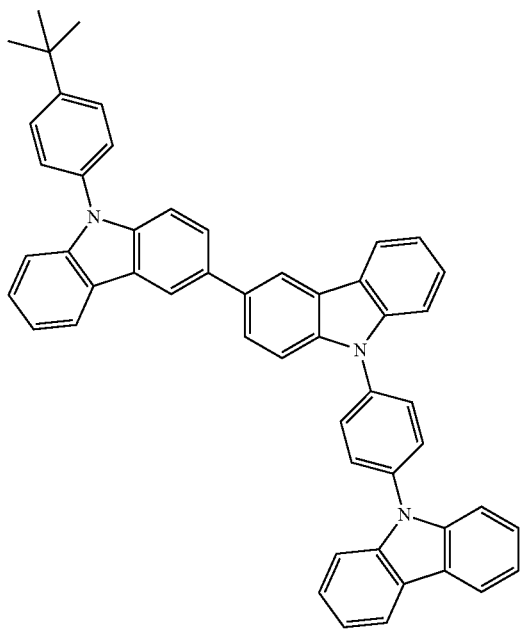
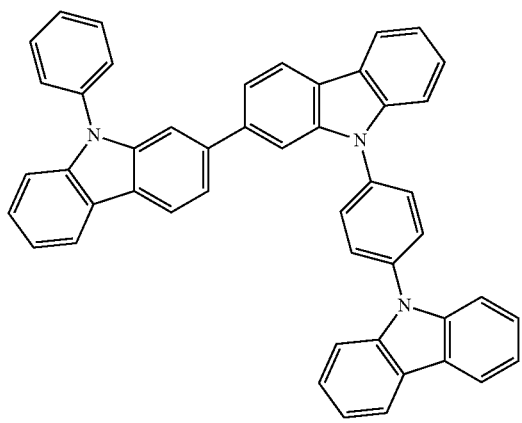
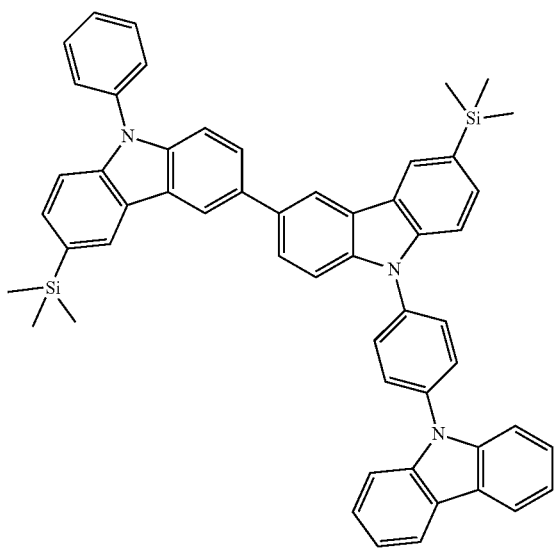

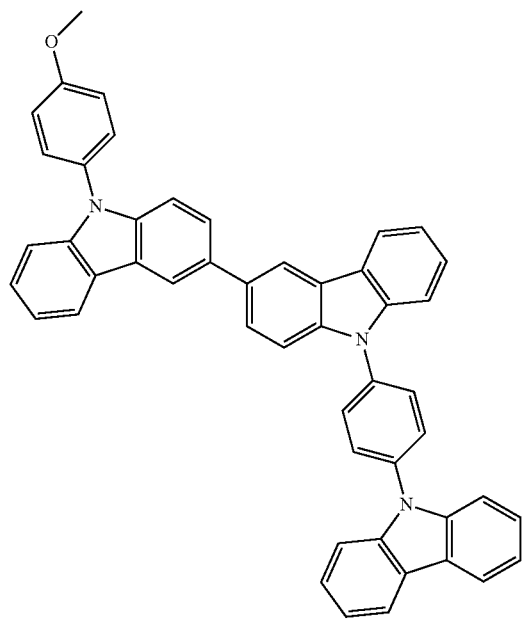
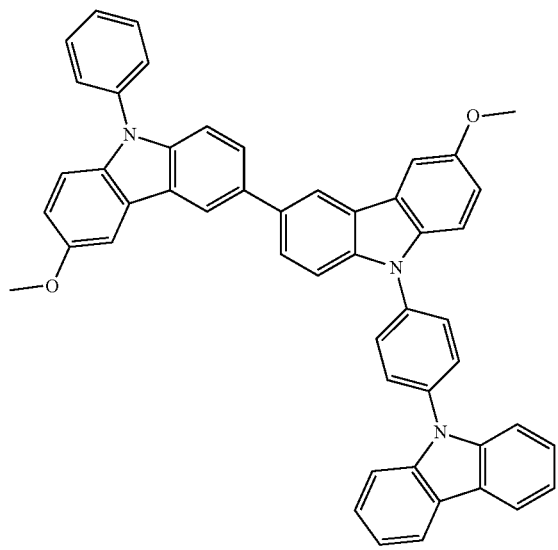

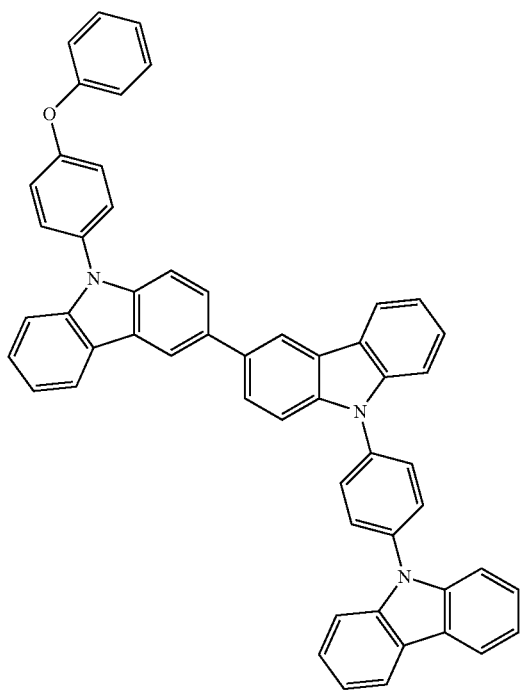
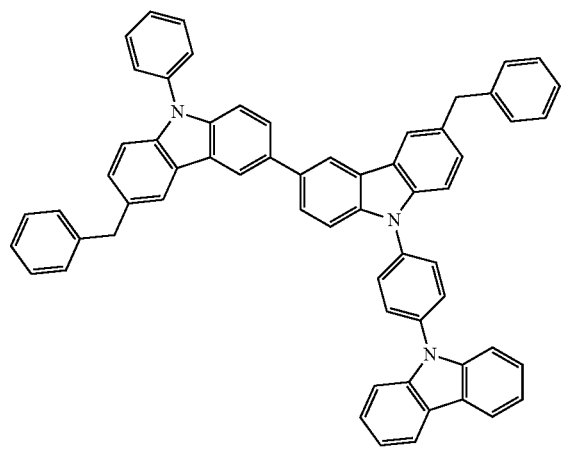
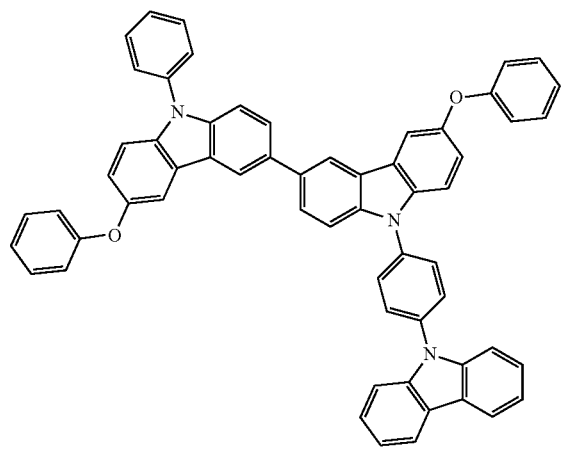

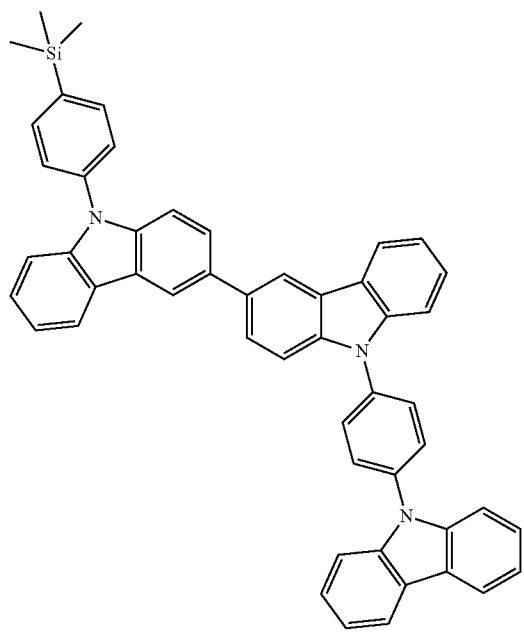
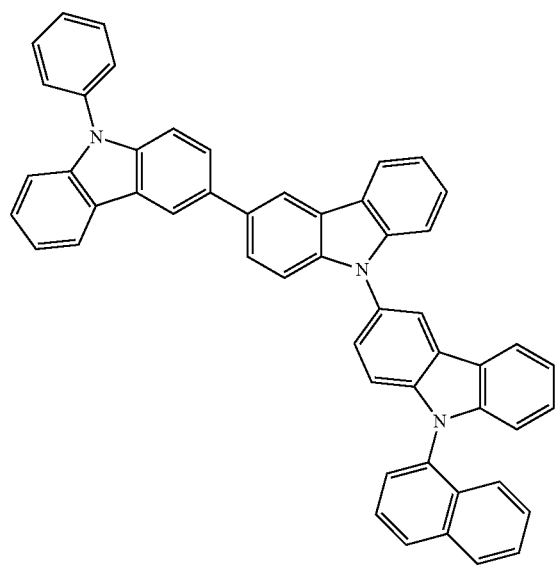

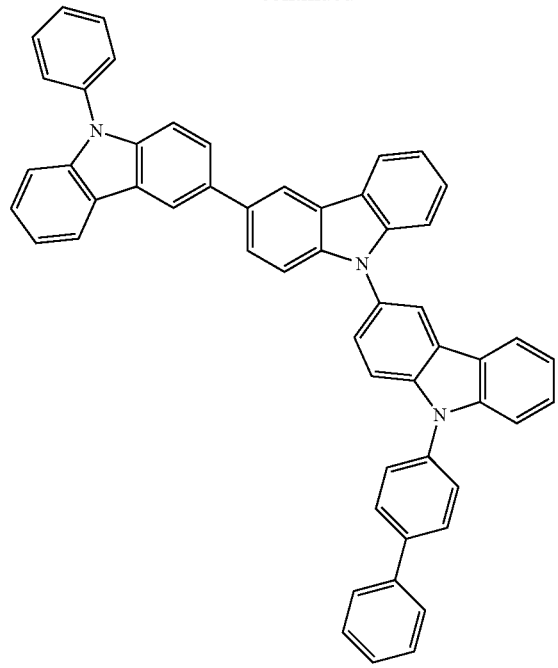
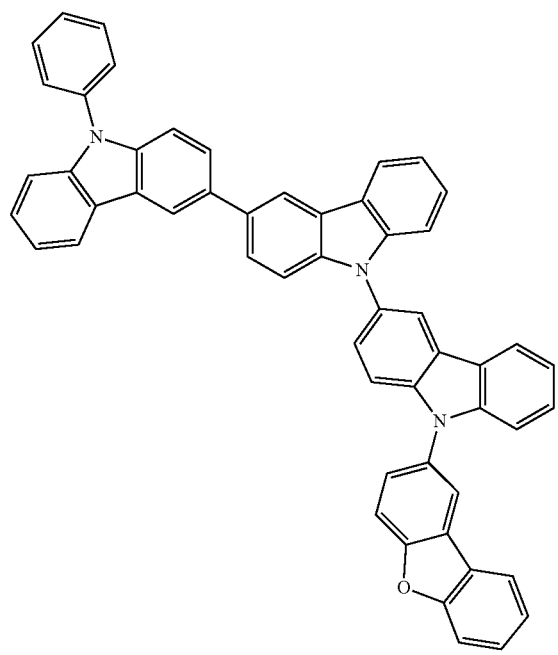

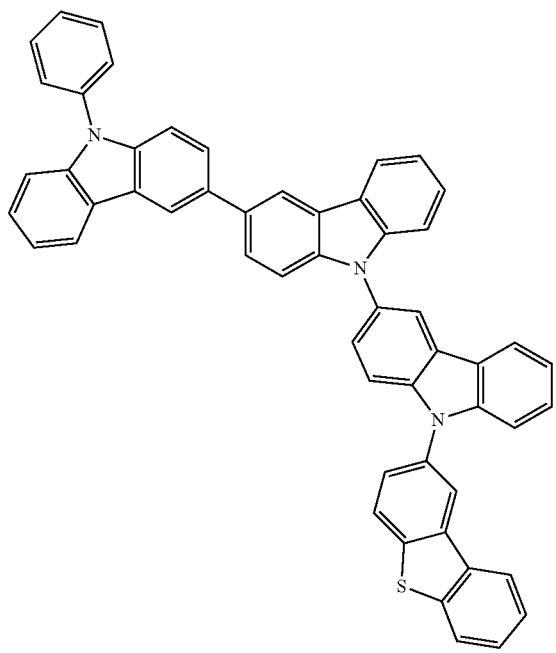
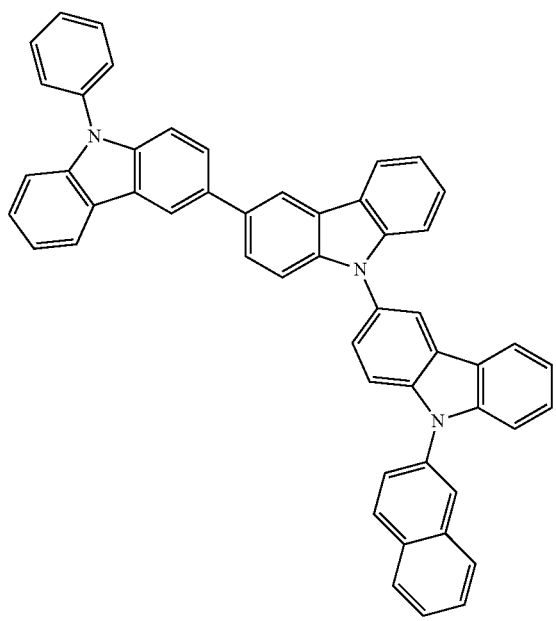

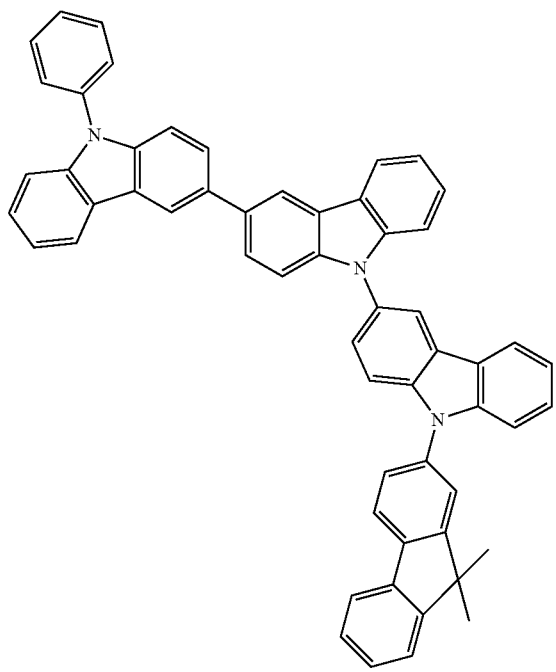
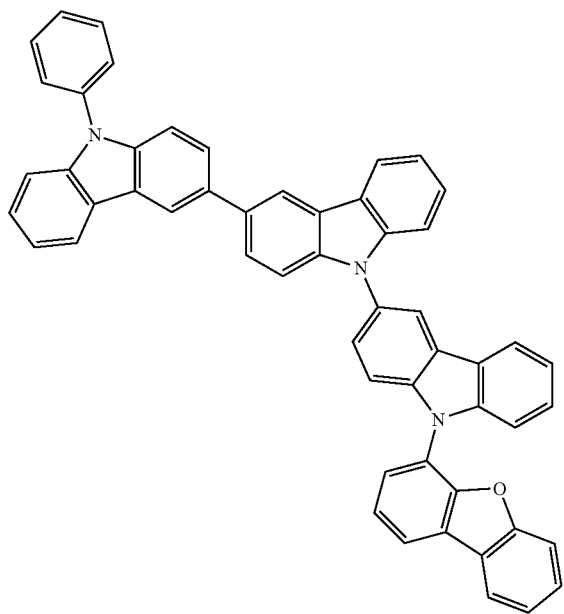

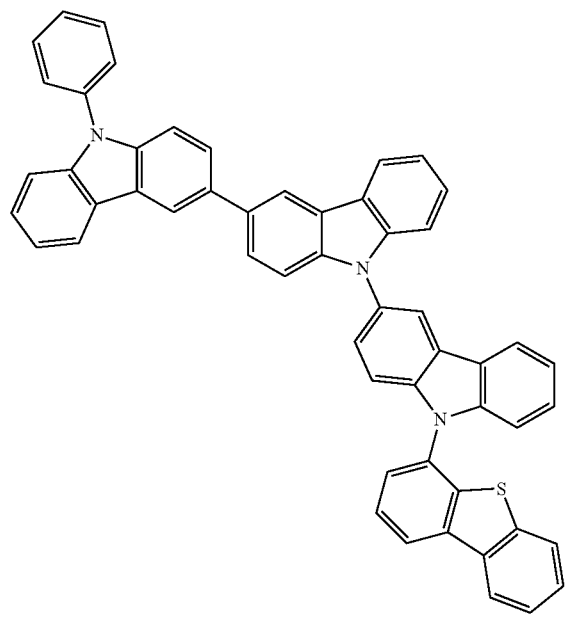
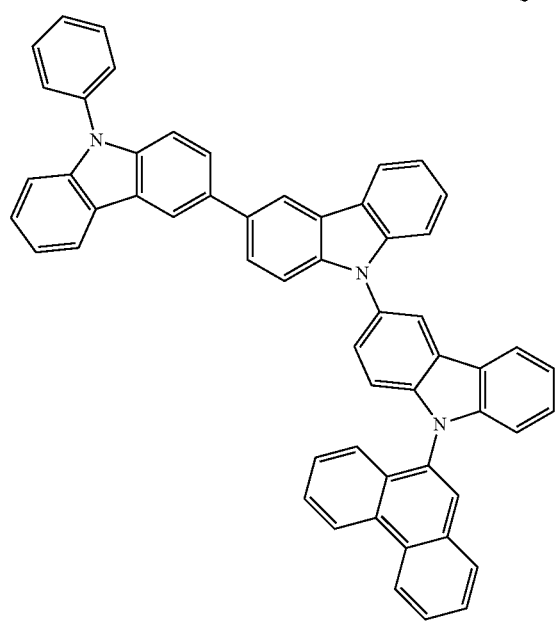
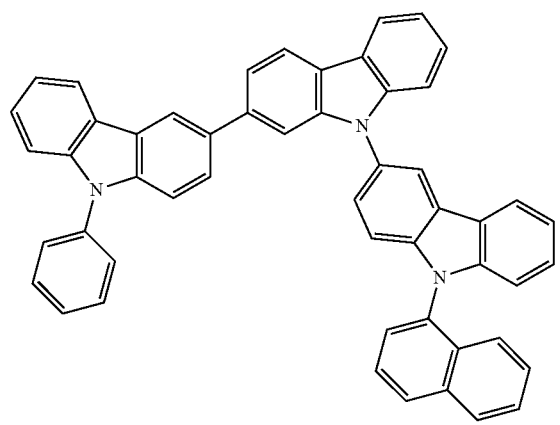

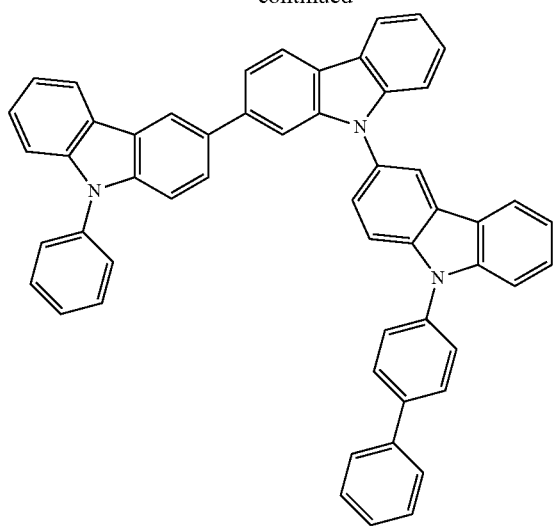
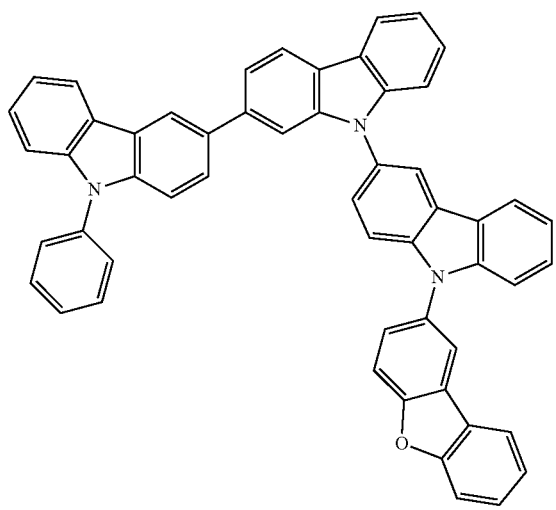
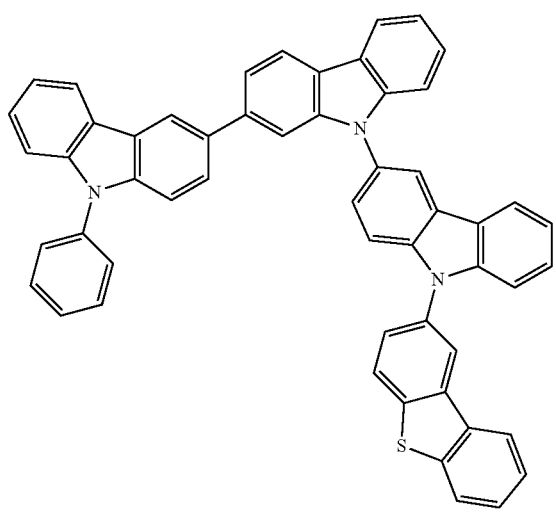

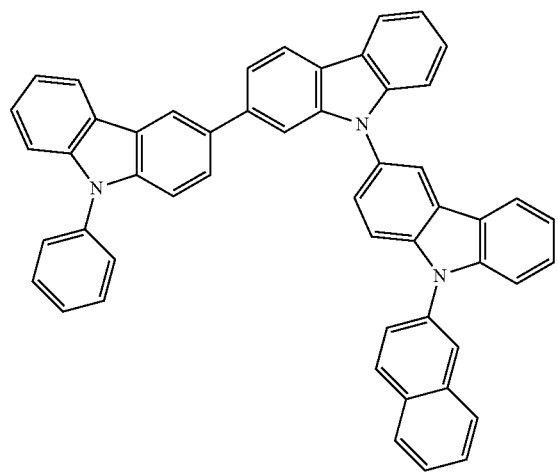
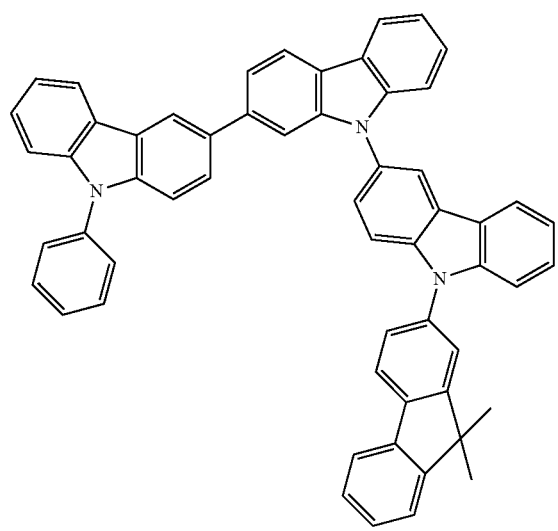
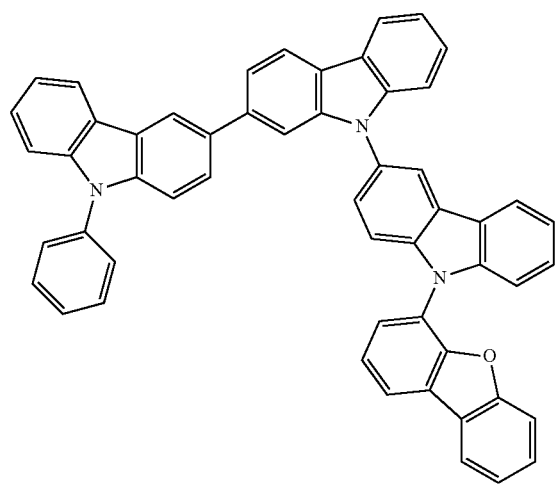

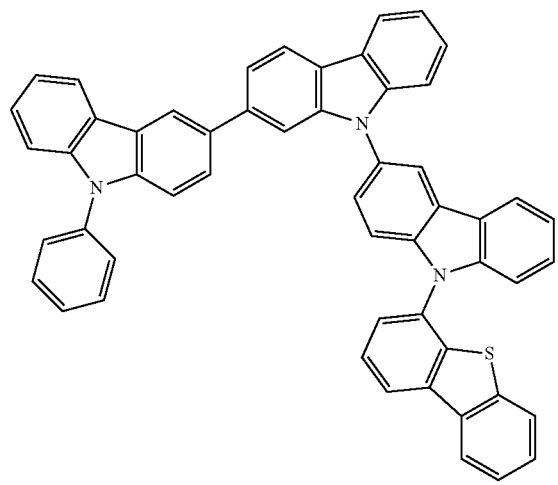
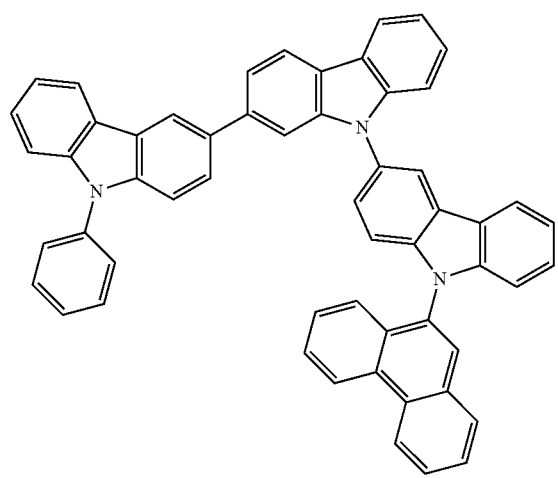
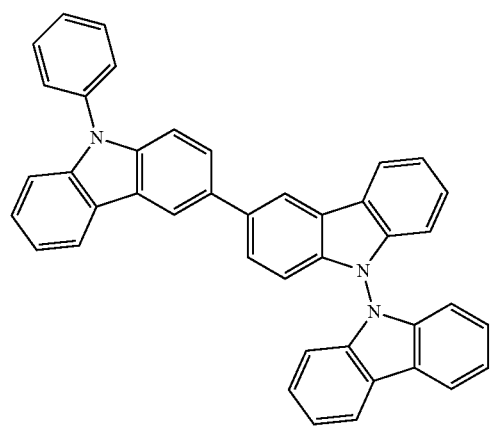

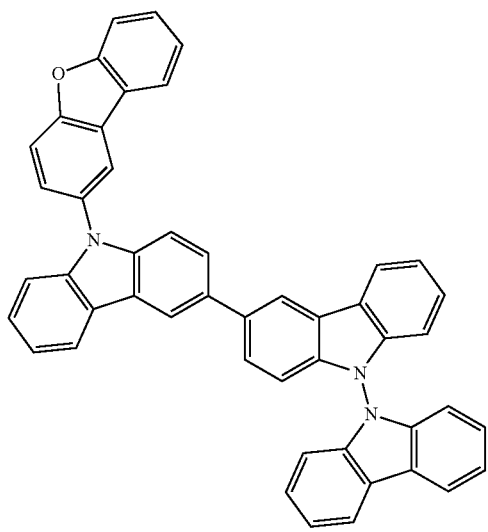
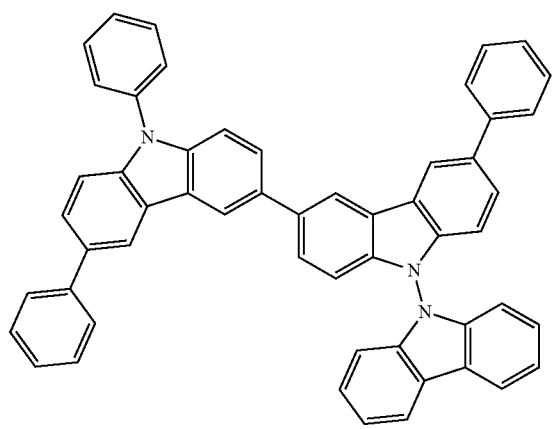
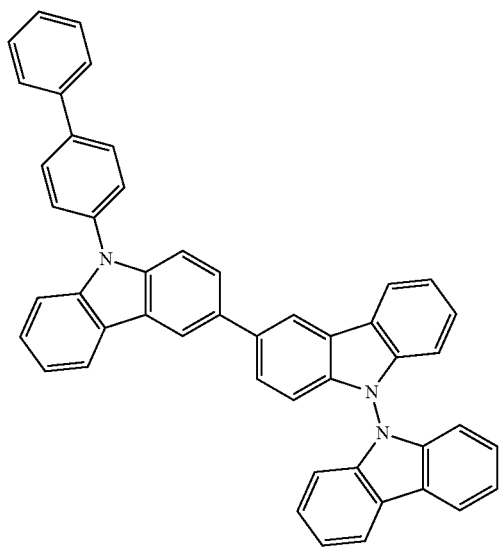

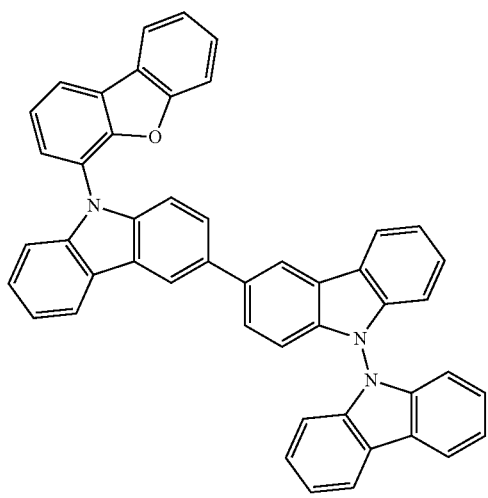
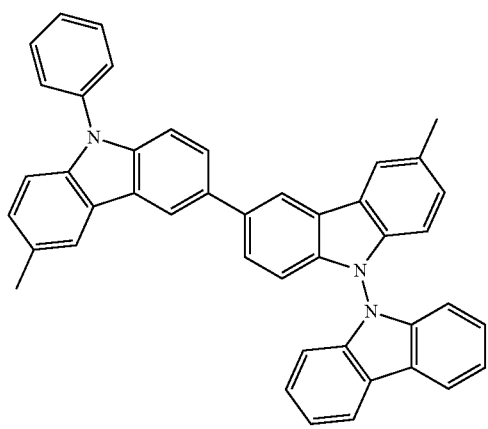
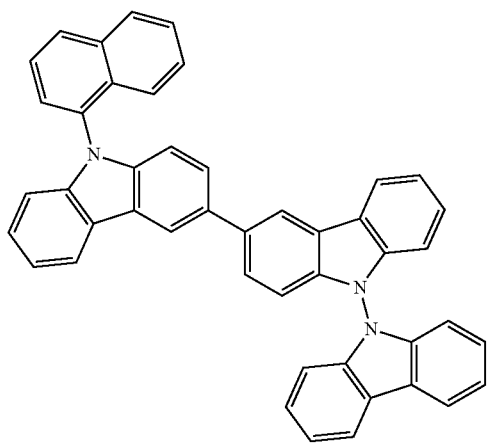

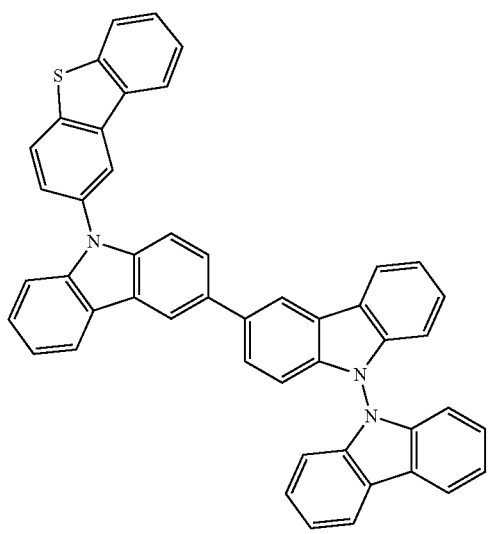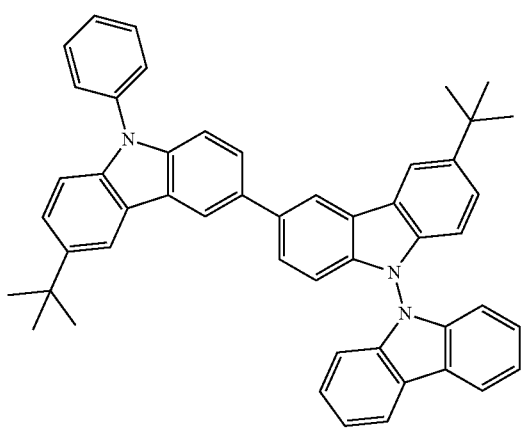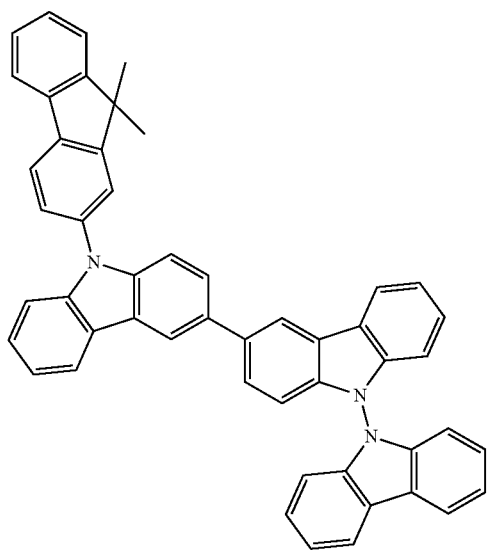

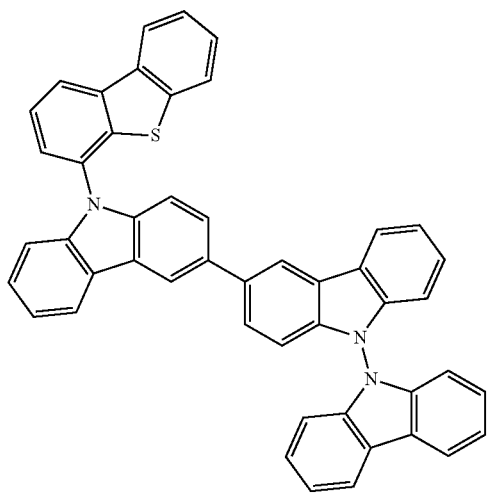
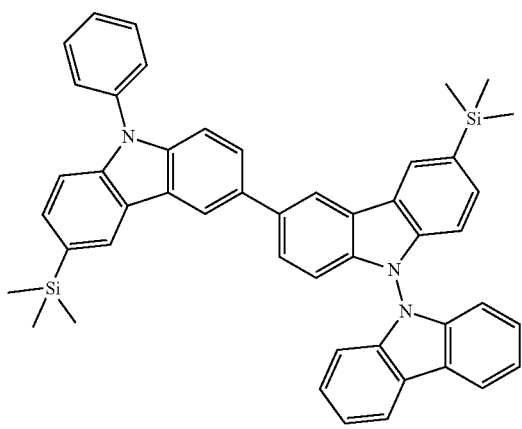
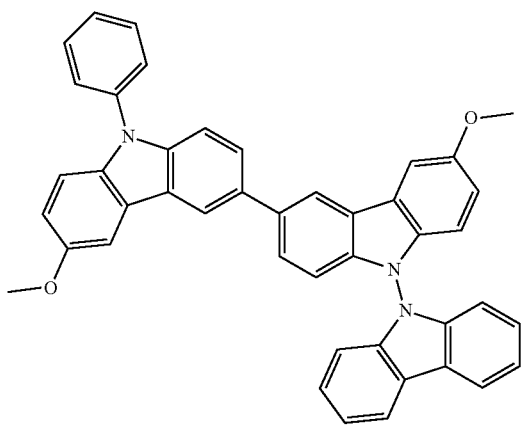

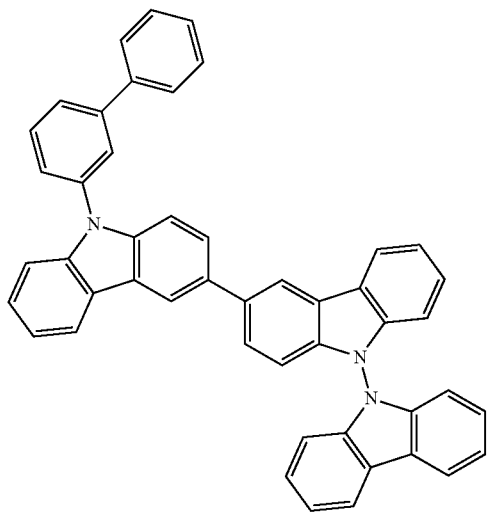
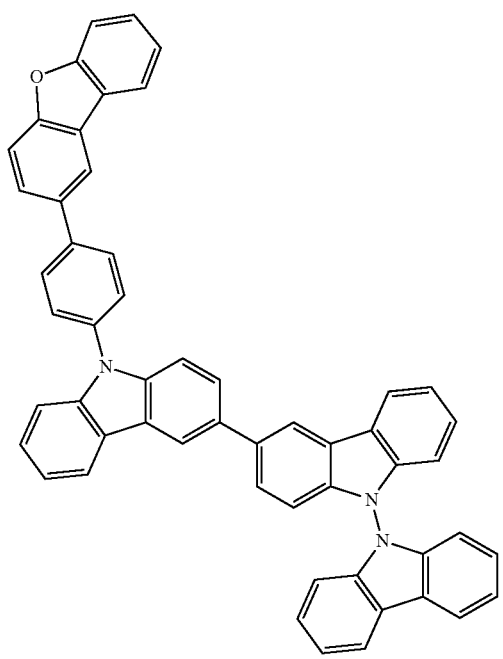
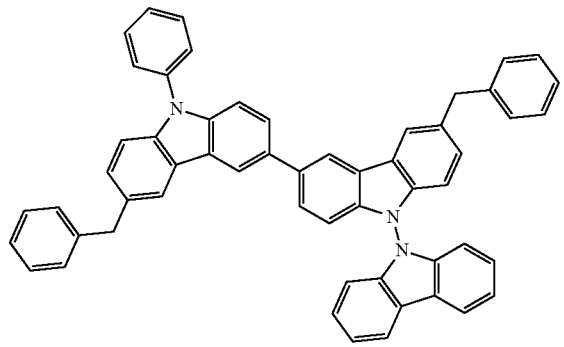

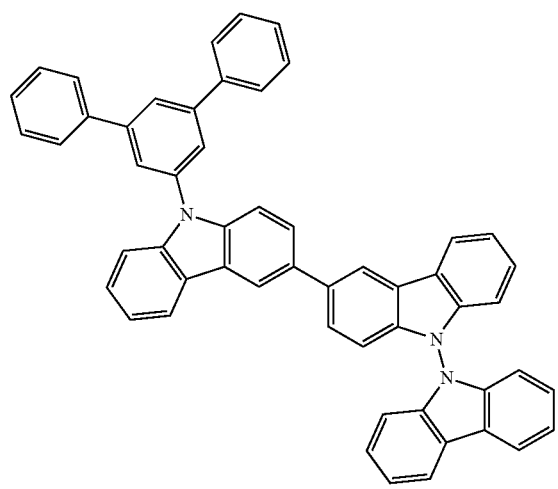
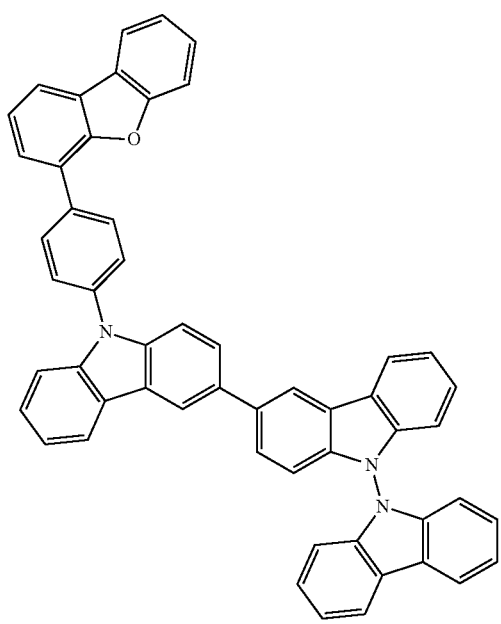
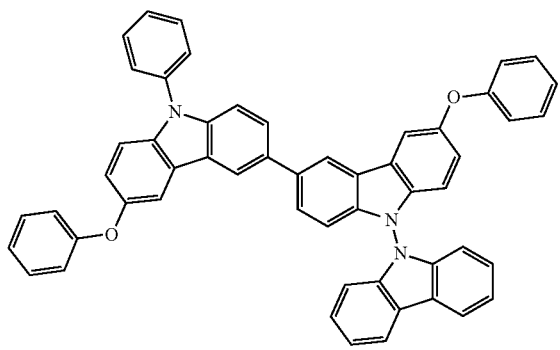

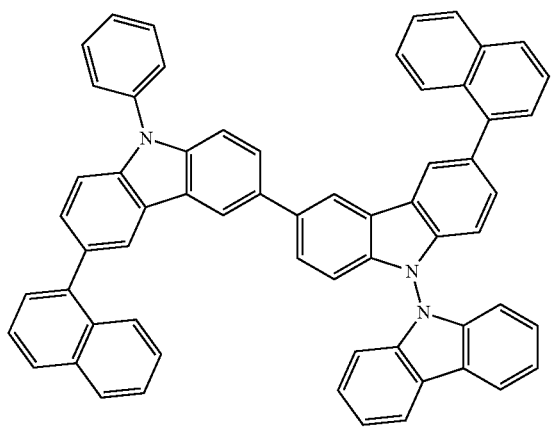
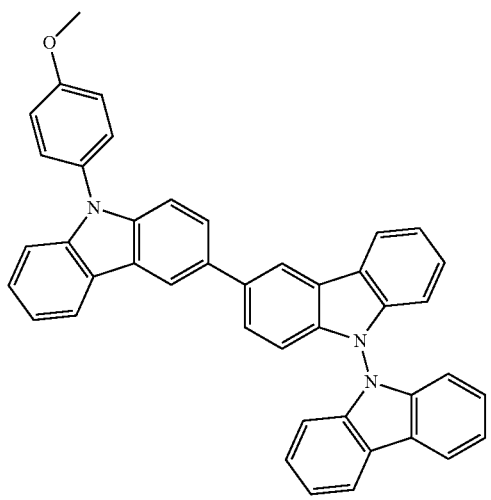
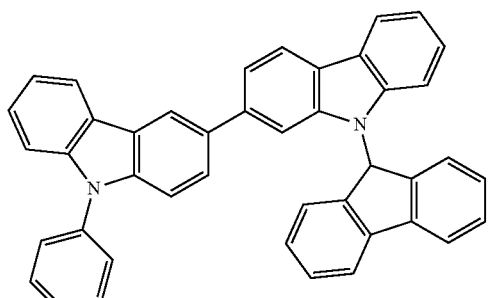
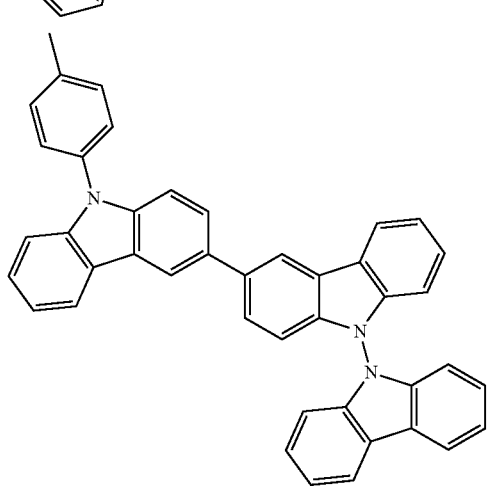

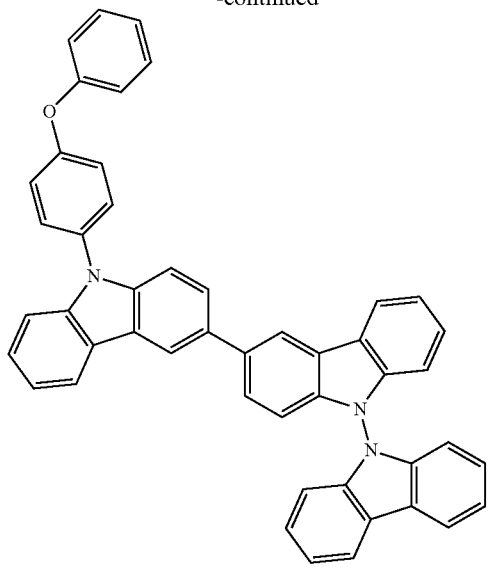
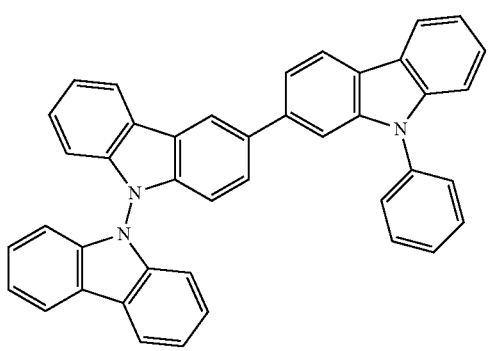
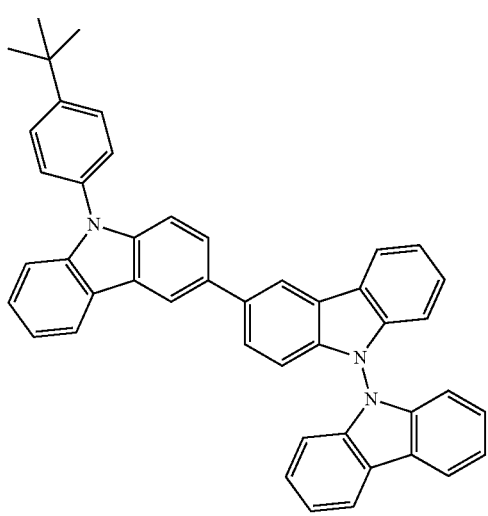

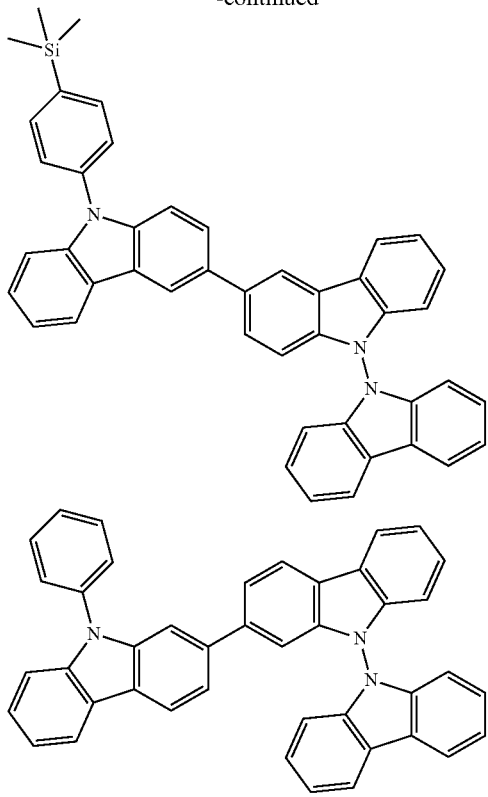

Organic EL Device

The organic EL device of the invention comprises one or more organic thin layers between the cathode and the anode, and at least one layer of the organic thin layers is a light emitting layer. At least one layer of the organic thin layers comprises at least one biscarbazole derivative of the invention. In a preferred embodiment, the organic EL device comprises a hole injecting layer and/or a hole transporting layer, and the hole injecting layer and/or the hole transporting layer comprises at least one biscarbazole derivative of the invention. The light emitting layer may comprises at least one biscarbazole derivative of the invention.

The structure of the organic EL device of the invention will be described below.

The representative device structures of the organic EL device of the invention are shown below, although not limited to the following structure:
(1) anode/hole transporting layer/light emitting layer/cathode;
(2) anode/hole injecting layer/hole transporting layer/light emitting layer/cathode;
(3) anode/hole injecting layer/hole transporting layer/light emitting layer/electron injecting layer/cathode; and
(4) anode/hole injecting layer/hole transporting layer/light emitting layer/electron transporting layer/electron injecting layer/cathode,
with the device structure (4) being preferably used.

An electron blocking layer may be disposed between the hole transporting layer and the light emitting layer, if necessary. In addition, a hole blocking layer may be disposed between the light emitting layer and the electron injecting layer or between the light emitting layer and the electron transporting layer, if necessary. By using the electron blocking layer or the hole blocking layer, electrons and holes are confined in the light emitting layer and the recombination of charges in the light emitting layer is enhanced, thereby improving the emission efficiency.

The biscarbazole derivative of the invention is used as the material for producing organic EL devices of a single emission unit type (simple type) and a laminated emission unit type (tandem type). For example, the biscarbazole derivative is usable as the material for forming a layer having a hole transporting function which is disposed between a light emitting layer and an anode of organic EL devices, and also as a phosphorescent emitting material for forming a light emitting layer because its triplet energy (first excited state) is large.

An example of the device structure of the organic EL device of the invention is schematically shown in FIG. 1. The organic EL device 1 includes a transparent substrate 2, an anode 3, a cathode 4, and organic thin-film layers 10 disposed between the anode 3 and the cathode 4. The organic thin-film layers 10 include a phosphorescent light emitting layer 5 including a phosphorescent host material and a phosphorescent dopant. A layer, such as a hole injecting/transporting layer 6, may be provided between the phosphorescent light emitting layer 5 and the anode 3 while a layer, such as an electron injecting/transporting layer 7, may be provided between the phosphorescent light emitting layer 5 and the cathode 4. An electron blocking layer may be provided on the anode 3 side of the phosphorescent light emitting layer 5 while a hole blocking layer may be provided on the cathode 4 side of the phosphorescent light emitting layer 5. With these blocking layers, electrons and holes can be confined in the phosphorescent light emitting layer 5, thereby enhancing the exciton generation in the phosphorescent light emitting layer 5.

In the present invention, a host is referred to as a fluorescent host when combinedly used with a fluorescent dopant and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

The term "hole injecting/transporting layer" as used herein refers to one or both of a hole injecting layer and a hole transporting layer, and the term "electron injecting/transporting layer" as used herein refers to one or both of an electron injecting layer and an electron transporting layer.

Transparent Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole injecting layer, the hole transporting layer or the light emitting layer, and an anode having a work function of 4.5 eV or more is effective. Examples of the material for anode include indium tin oxide alloy (ITO), tin oxide (NESA), indium zinc oxide alloy, gold, silver, platinum, and copper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds Ω/□ or less. The film thickness of anode depends upon the kind of material and generally 10 nm to 1 μn, preferably 10 to 200 nm.

Cathode

The cathode injects electrons to the electron injecting layer, the electron transporting layer or the light emitting layer, and formed preferably by a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken through the cathode, if necessary.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

The easiness of hole injection to the light emitting layer and the easiness of electron injection to the light emitting layer may be different from each other. Also, the hole transporting ability and the electron transporting ability each being expressed by mobility of holes and electrons in the light emitting layer may be different from each other.

The light emitting layer is formed, for example, by a known method, such as a vapor deposition method, a spin coating method, and LB method. The light emitting layer can be formed also by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The phosphorescent dopant (phosphorescent emitting material) used in the light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. The ligand is preferably ortho-metallated. In view of obtaining a high phosphorescent quantum yield and further improving the external quantum efficiency of electroluminescence device, a metal complex comprising a metal selected from Ir, Os, and Pt is preferred, with a metal complex, such as an iridium complex, an osmium complex, and a platinum complex, being more preferred, an iridium complex and a platinum complex being still more preferred, and an ortho-metallated iridium complex being particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex are shown below.

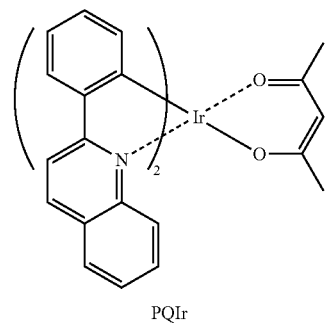

PQIr

151
-continued
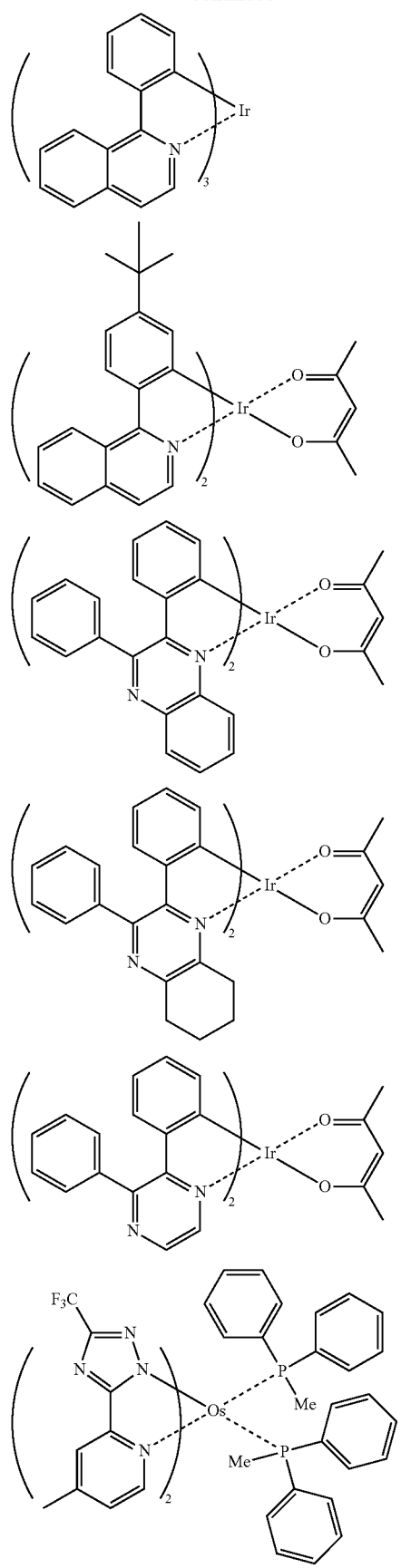
152
-continued
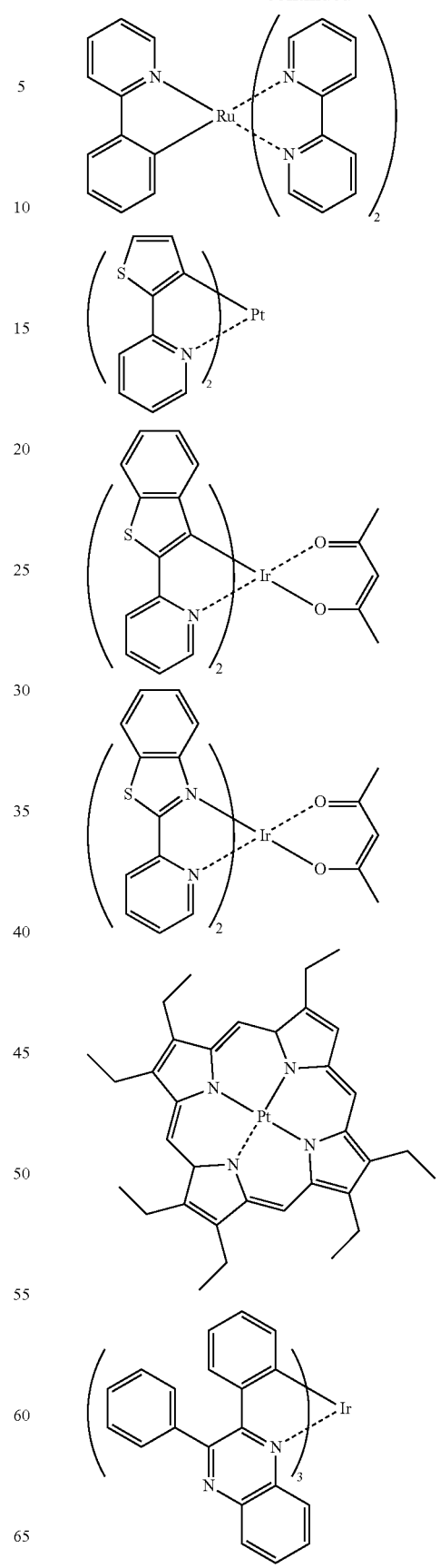

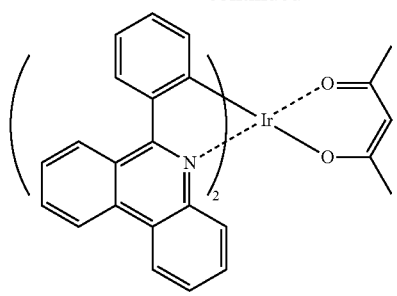
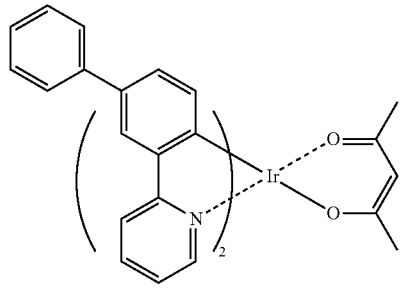
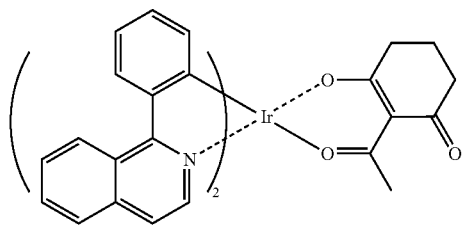
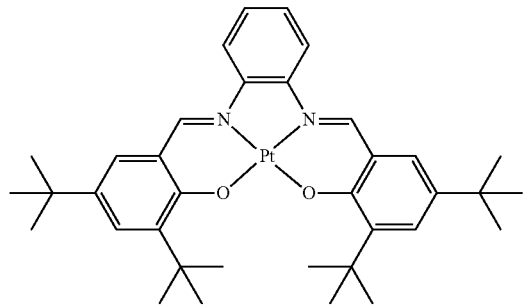
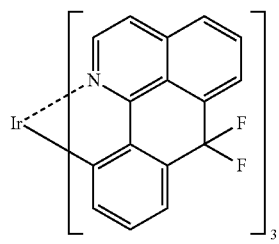
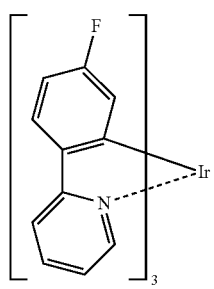
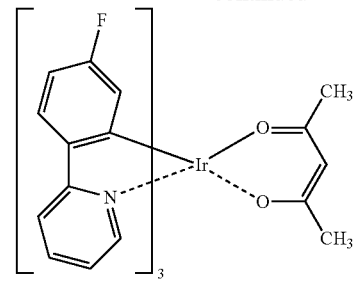
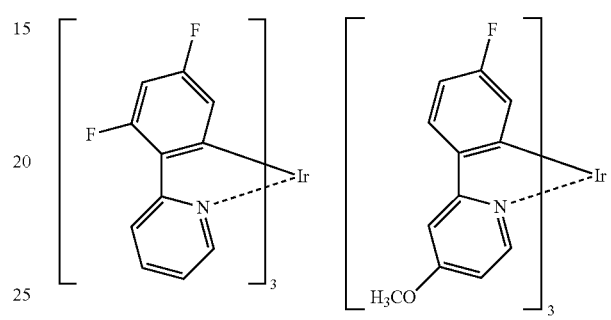
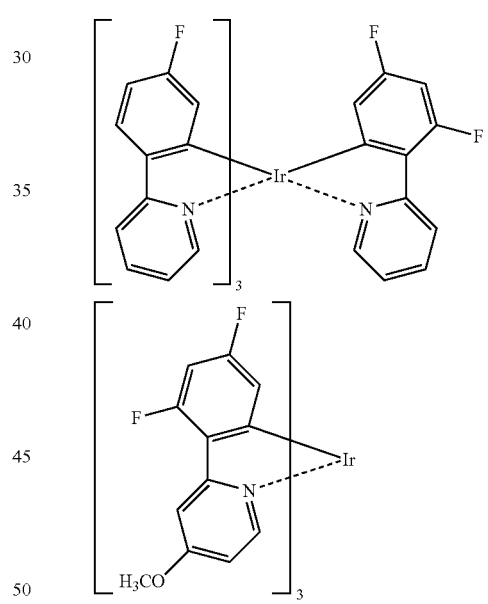
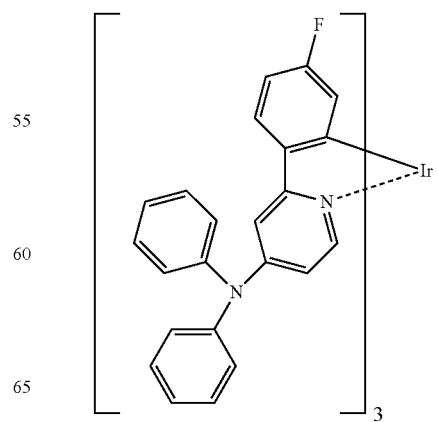

-continued
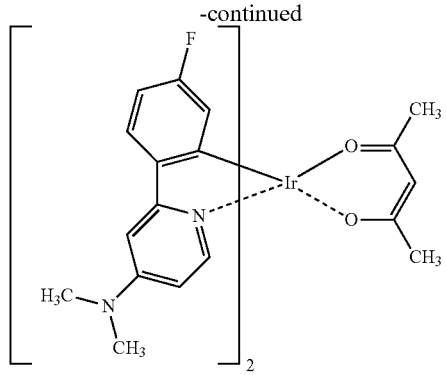
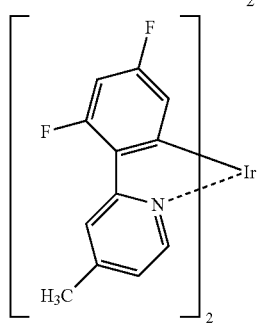
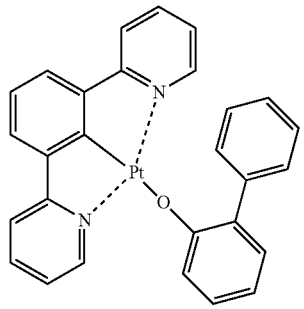
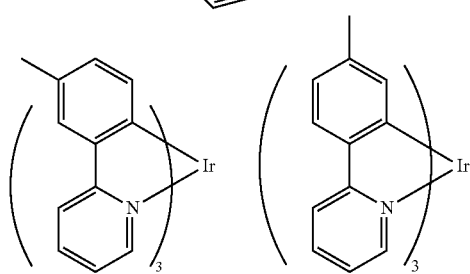
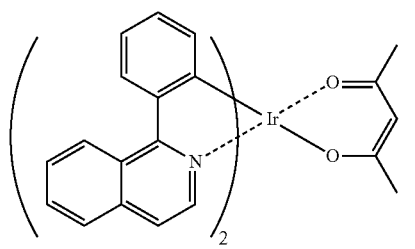
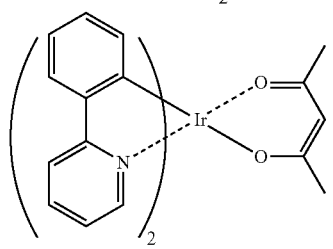
-continued
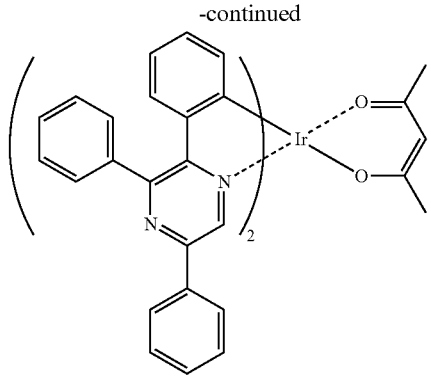
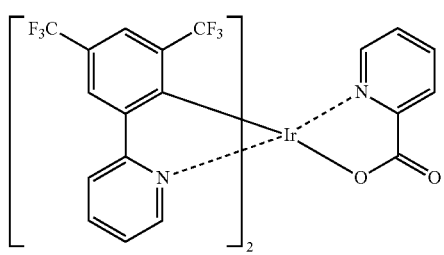
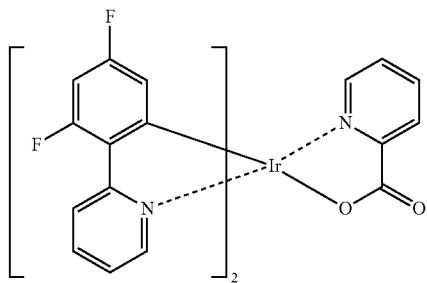
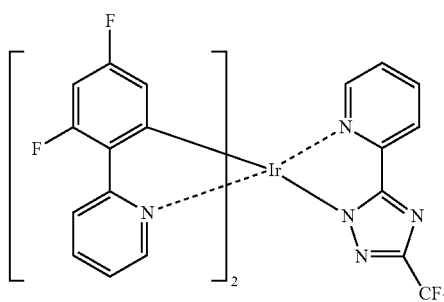
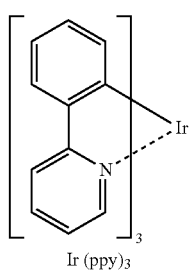
Ir (ppy)₃

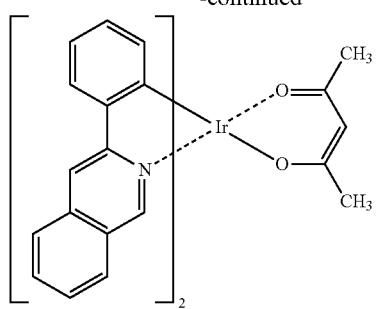
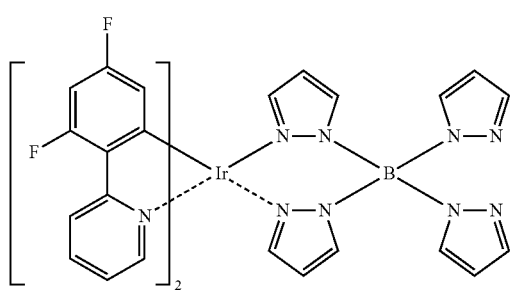
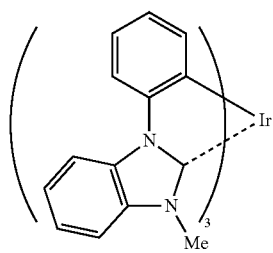
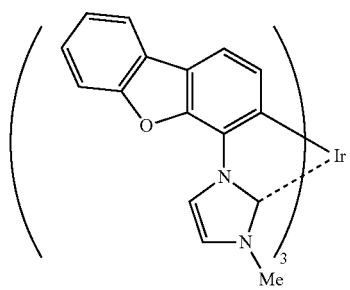
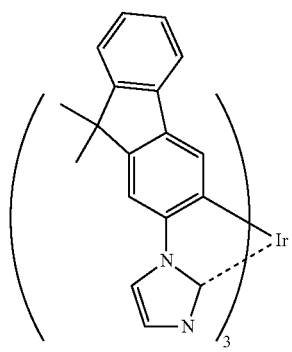
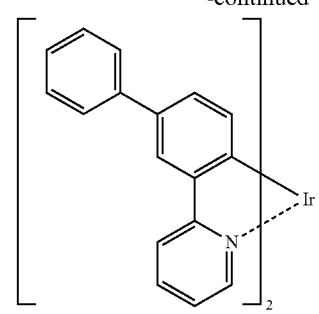
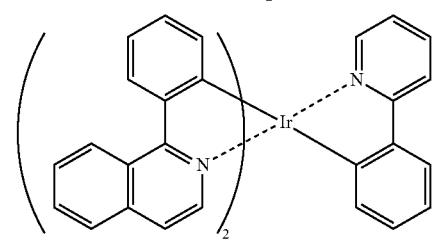
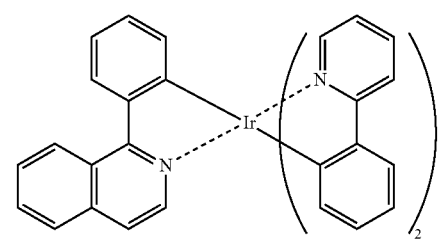
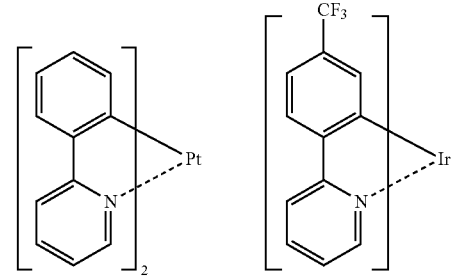
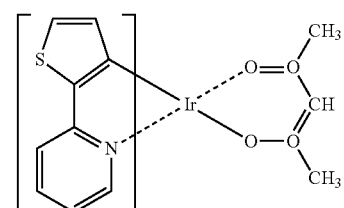
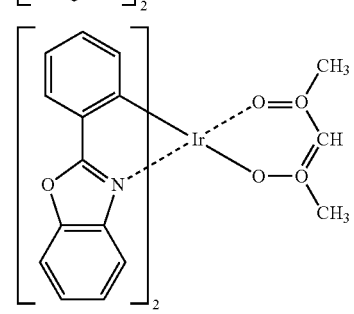

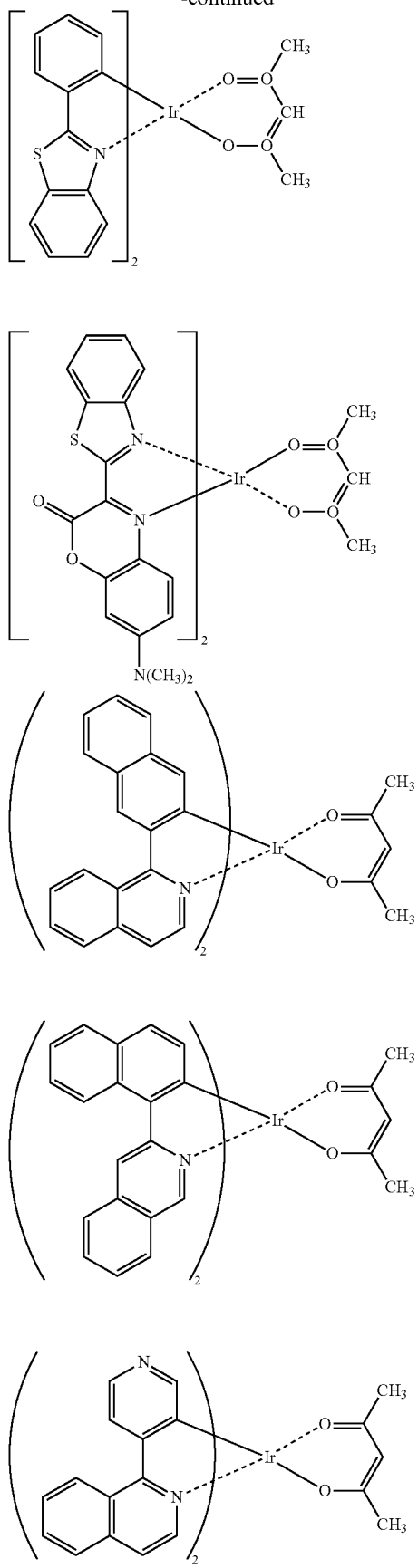

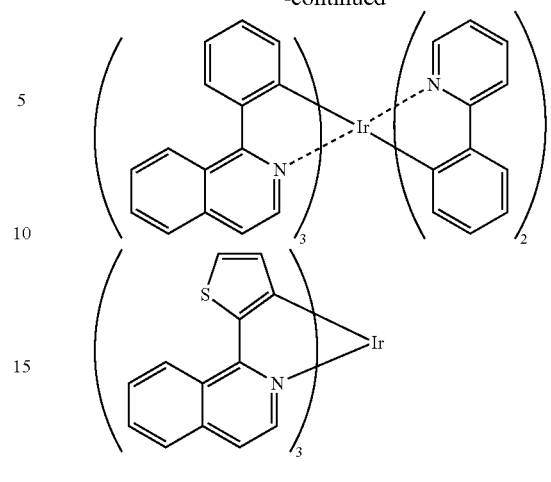

The phosphorescent host is a compound capable of causing the emission of phosphorescent dopant by transferring energy from its excited state to the phosphorescent dopant. The phosphorescent host is not particularly limited as long as it is capable of transferring the exciton energy to the phosphorescent dopant and may be appropriately selected according to the purpose.

Examples of the phosphorescent host include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Specific examples thereof are shown below.

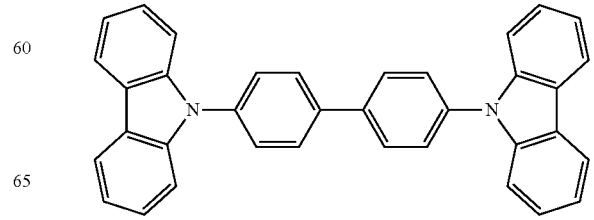

-continued

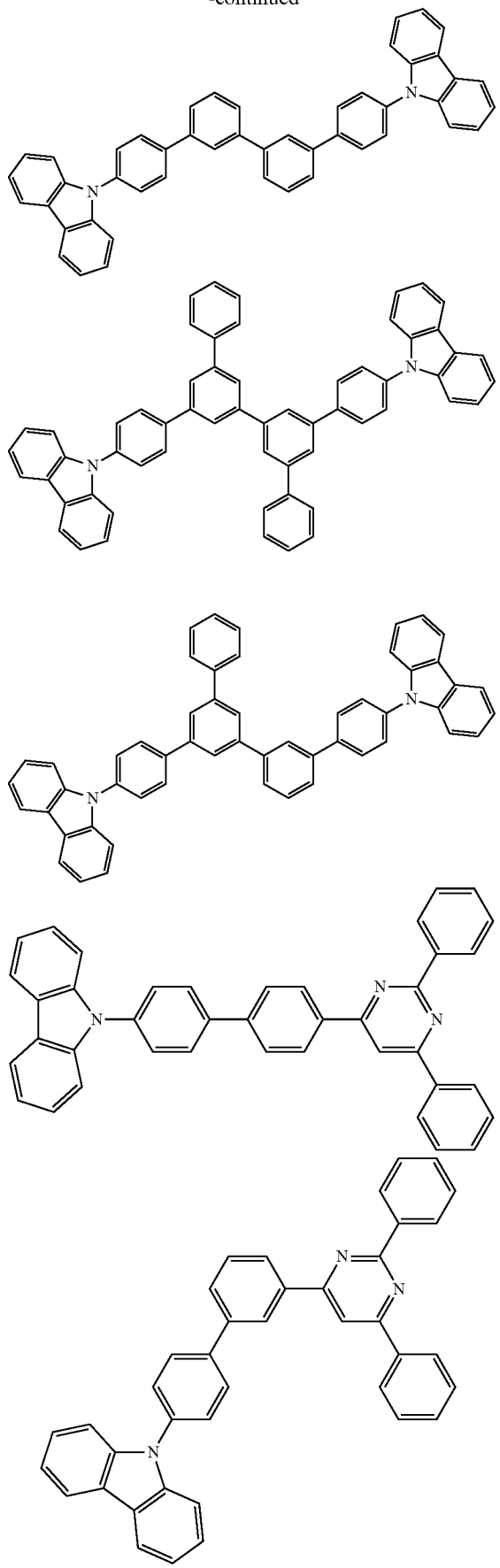

The thickness of the light emitting layer is preferably 5 to 50 nm, more preferably 7 to 50 nm, and still more preferably 10 to 50 nm. If being 5 nm or more, the light emitting layer is easily formed. If being 50 nm or less, the increase in driving voltage is avoided.

Electron-Donating Dopant

The organic EL device of the present invention preferably comprises an electron-donating dopant at an interfacial region between the cathode and the organic thin film layer. With such a construction, the organic EL device has an improved luminance and an elongated lifetime. Examples of the electron-donating dopant include at least one compound selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCA^1_{-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device of the invention is preferably 5:1 to 1:5 and more preferably 2:1 to 1:2.

Electron Injecting/Transporting Layer

The electron injecting/transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in a molecule thereof is preferably used as an electron transporting material used in the electron injecting/transporting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

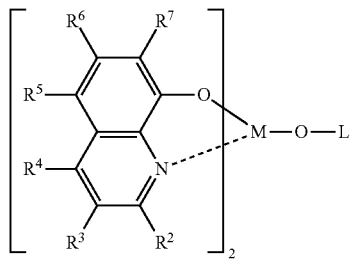

wherein each of $R^2$ to $R^7$ independently represents a hydrogen atom, a deuterium atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or an aromatic heterocyclic group having 5 to 50 ring carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by —$NQ^1Q^2$. Each of $Q^1$ and $Q^2$ independently represents an alkyl group having 1 to 20 carbon atoms or an aralkyl group having 1 to 20 carbon atoms. One of $Q^1$ and $Q^2$ may be a hydrogen atom or a deuterium atom.

The arylamino group is represented by —$NAr^1Ar^2$, wherein each of $Ar^1$ and $Ar^2$ independently represents a non-fused aromatic hydrocarbon groups or a fused aromatic hydrocarbon groups, each having 6 to 50 carbon atoms. One of $Ar^1$ and $Ar^2$ may be a hydrogen atom or a deuterium atom.

Examples of the hydrocarbon group having 1 to 40 carbon atoms include an alkyl group, an alkenyl group, a cycloalkyl group, an aryl group, and an aralkyl group.

The alkoxycarbonyl group is represented by —COOY', wherein Y' is an alkyl group having 1 to 20 carbon atoms.

M is aluminum (Al), gallium (Ga), or indium (In), with In being preferred.

L is a group represented by formula (A') or (A"):

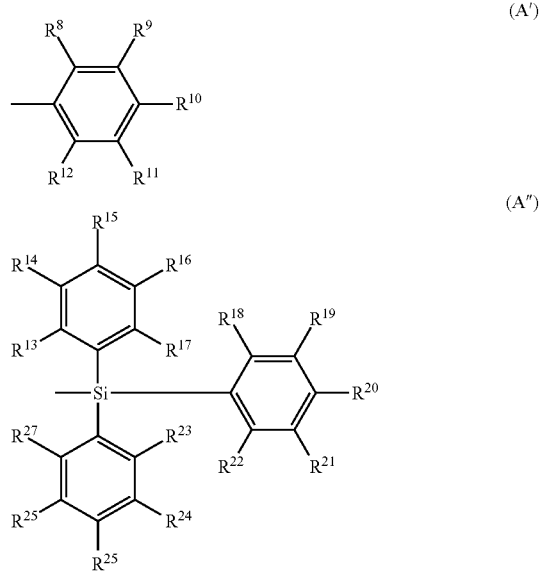

wherein each $R^8$ to $R^{12}$ independently represents a hydrogen atom, a deuterium atom, or a substituted or unsubstituted hydrocarbon group having 1 to 40 carbon atoms. The adjacent two groups may form a ring structure. Each of $R^{13}$ to $R^{27}$ independently represents a hydrogen atom, a deuterium atom, or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$ of formula (A). Examples of the divalent group formed by the adjacent two groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

The electron transporting compound for the electron injecting/transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

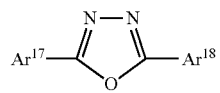

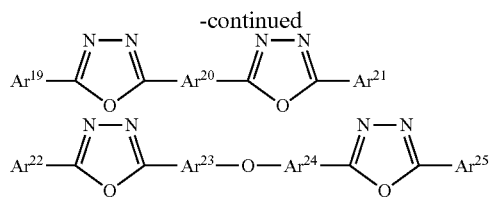

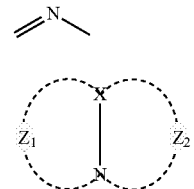

(B)

(C)

wherein X is a carbon atom or a nitrogen atom and each of $Z_1$ and $Z_2$ independently represents a group of atoms for completing the nitrogen-containing heteroring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D):

(D)

The nitrogen-containing group of the nitrogen-containing aromatic polycyclic compound is selected, for example, from the nitrogen-containing heterocyclic groups shown below:

wherein each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted fused aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the fused aromatic hydrocarbon group include phenyl group, naphthyl group, a biphenyl group, anthranyl group, perylenyl group, and pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted or unsubstituted bivalent fused aromatic hydrocarbon group each having 6 to 50 carbon atoms, and $Ar^{23}$ and $Ar^{24}$ may be the same or different. Examples of the bivalent aromatic hydrocarbon group or the bivalent fused aromatic hydrocarbon group include phenylene group, naphthylene group, biphenylene group, anthranylene group, perylenylene group, and pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

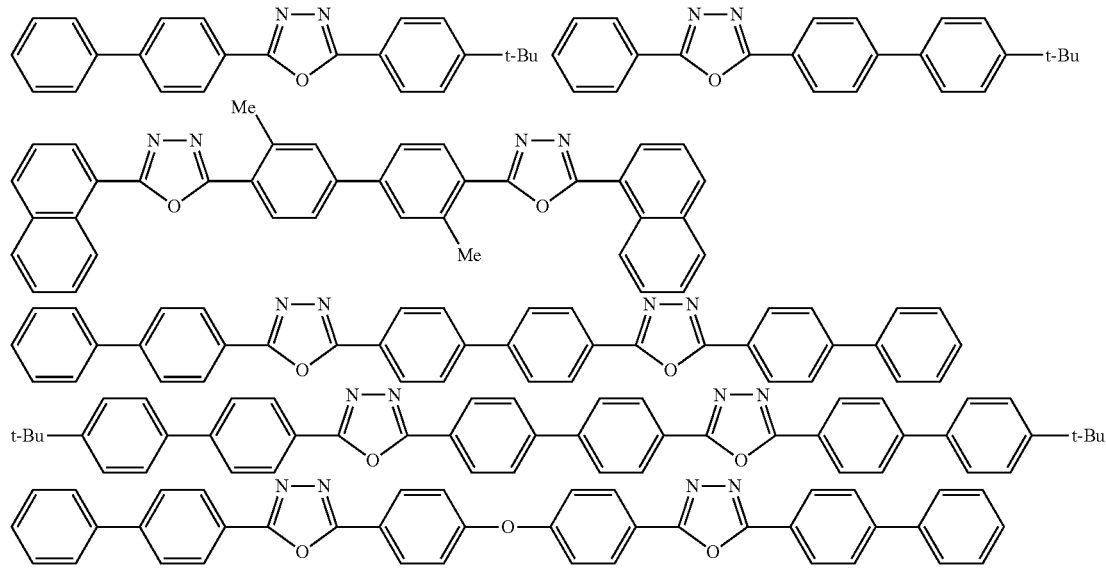

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C):

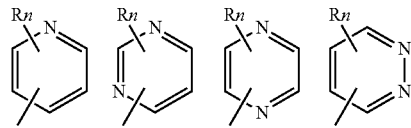

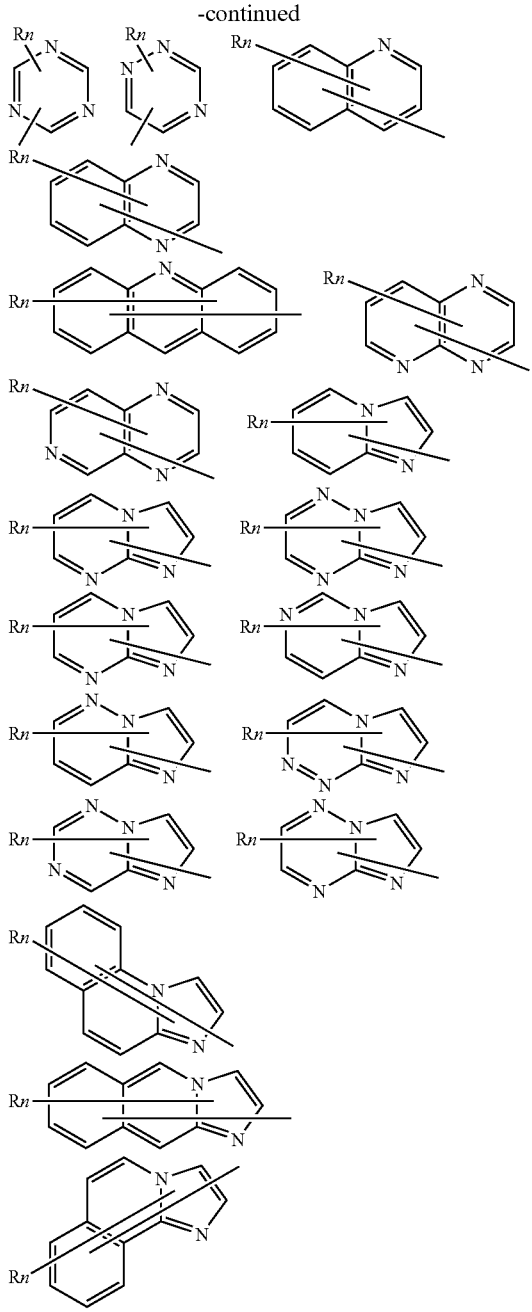

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by the following formula:

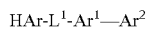

wherein HAr is a substitute or unsubstituted nitrogen-containing heterocyclic group having 3 to 40 carbon atoms; $L^1$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^1$ is a substitute or unsubstituted divalent aromatic hydrocarbon group having 6 to 40 carbon atoms; and $Ar^2$ is a substitute or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

HAr is selected, for example, from the following groups:

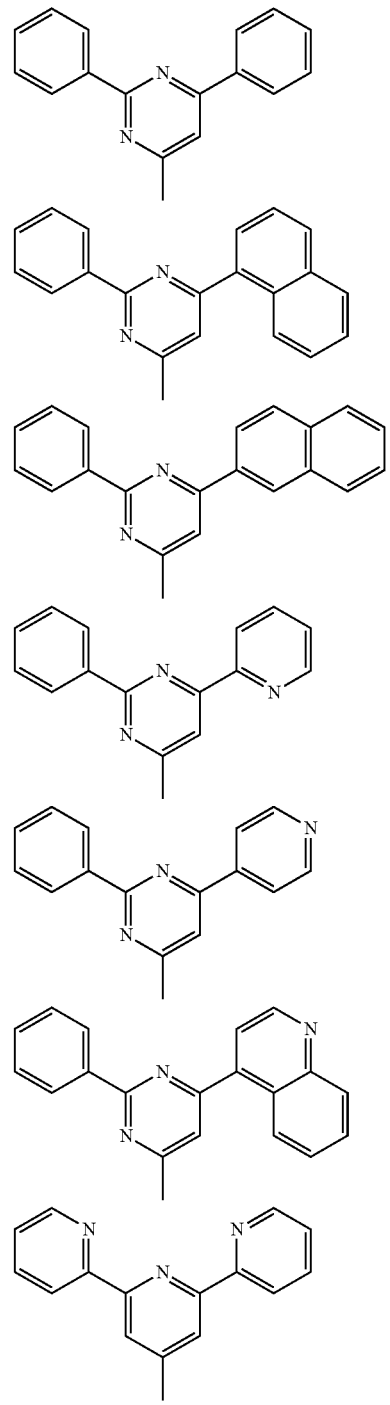

-continued

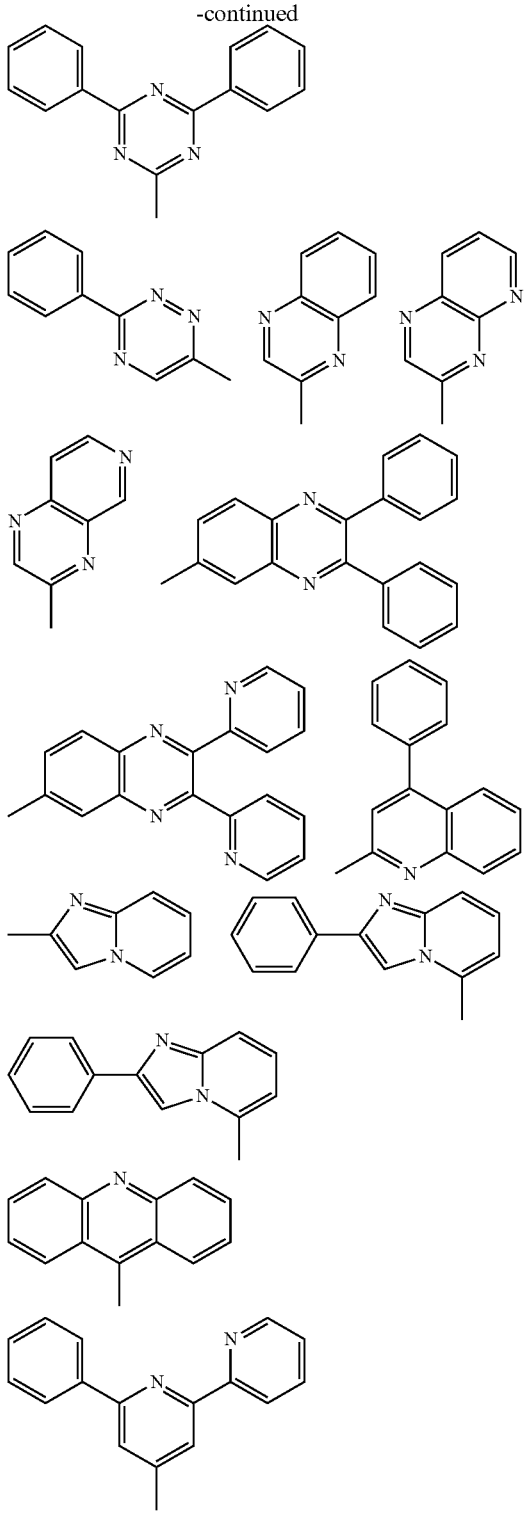

L¹ is selected, for example, from the following groups:

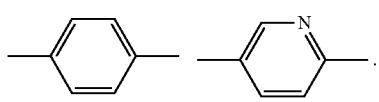

Ar¹ is selected, for example, from the following arylanthranyl groups:

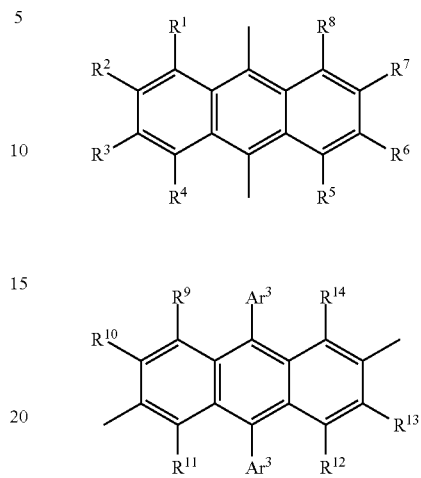

wherein $R^1$ to $R^{14}$ are each independently a hydrogen atom, a deuterium atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and $Ar^3$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

$R^1$ to $R^8$ may be selected from a hydrogen atom and a deuterium atom.

$Ar^2$ is selected, for example, from the following groups:

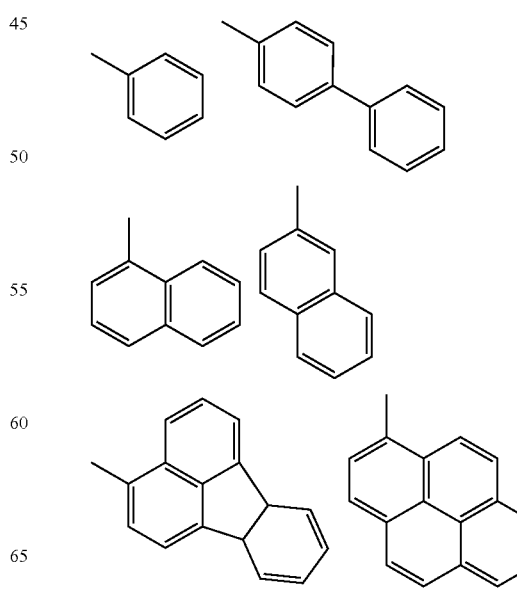

-continued

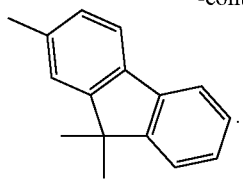

In addition, the following compound is preferably used as the nitrogen-containing aromatic polycyclic compound for use as the electron transporting compound:

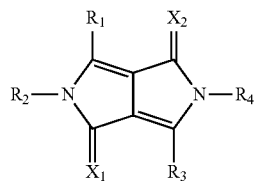

wherein $R_1$ to $R_4$ each independently represent a hydrogen atom, a deuterium atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and $X_1$ and $X_2$ each independently represent an oxygen atom, a sulfur atom, or dicyanomethylene group.

Further, the following compound is also suitable as the electron transporting compound:

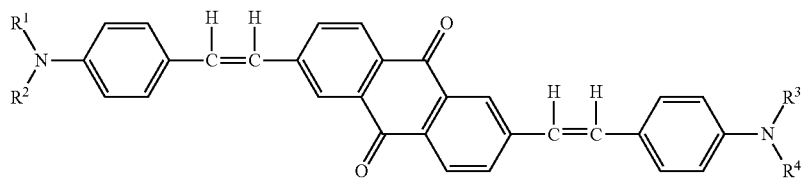

wherein $R^1$, $R^2$, $R^3$, and $R^4$ may be the same or different and each represents an aromatic hydrocarbon group or a fused aromatic hydrocarbon group each represented by the following formula:

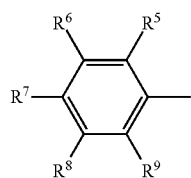

wherein $R^5$, $R^6$, $R^7$, $R^8$, and $R^9$ may be the same or different and each represents a hydrogen atom, a deuterium atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of $R^5$, $R^6$, $R^7$, $R^8$, and $R^9$ represents a group other than a hydrogen atom and a deuterium atom.

Further, a polymer having the nitrogen-containing heterocyclic group or the nitrogen-containing heterocyclic derivative is also usable as the electron transporting compound.

The electron transporting layer in the organic EL device of the invention preferably comprises at least one compound selected from the nitrogen-containing heterocyclic derivatives represented by formulae (60) to (62):

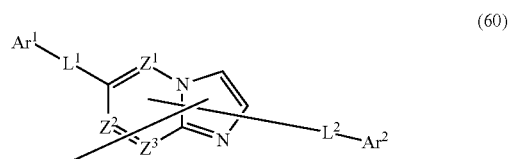
(60)

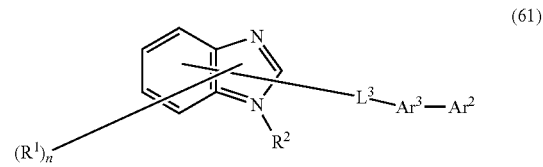
(61)

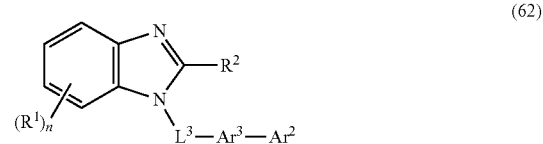
(62)

wherein $Z^1$, $Z^2$, and $Z^3$ each independently represent a nitrogen atom or a carbon atom;

$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms;

n is an integer of 0 to 5, when n is an integer of 2 or more, $R^1$ groups may be the same or different, and the adjacent two $R^1$ groups may bond to each other to form a substituted or unsubstituted hydrocarbon ring;

$Ar^1$ represents a substituted or unsubstituted aryl group having 6 to 50 ring carbon atoms or a substituted or unsubstituted heteroaryl group having 5 to 50 ring atoms;

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms;

provided that one of $Ar^1$ and $Ar^2$ is a substituted or unsubstituted condensed aromatic hydrocarbon group having 10 to 50 ring carbon atoms or a substituted or unsubstituted condensed aromatic heterocyclic group having 9 to 50 ring atoms;

Ar$^3$ represents a substituted or unsubstituted arylene group having 6 to 50 ring carbon atoms or a substituted or unsubstituted heteroarylene group having 5 to 50 ring atoms; and L$^1$, L$^2$, and L$^3$ each independently represent a single bond, a substituted or unsubstituted arylene group having 6 to 50 ring carbon atoms or a substituted or unsubstituted divalent condensed aromatic heterocyclic group having 9 to 50 ring atoms.

Examples of the aryl group having 6 to 50 ring carbon atoms include phenyl group, naphthyl group, anthryl group, phenanthryl group, naphthacenyl group, chrysenyl group, pyrenyl group, a biphenyl group, terphenyl group, tolyl group, fluoranthenyl group, and fluorenyl group.

Examples of the heteroaryl group having 5 to 50 ring atoms include pyrrolyl group, furyl group, thiophenyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, pyrazinyl group, pyridazinyl group, triazinyl group, quinoxalinyl group, acridinyl group, imidazo[1,2-a]pyridinyl group, and imidazo[1,2-a]pyrimidinyl.

Examples of the alkyl group having 1 to 20 carbon atoms include methyl group, ethyl group, propyl group, butyl group, pentyl group, and hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene groups include the groups obtained by removing one hydrogen atom from the aryl group mentioned above.

Examples of the divalent condensed aromatic heterocyclic group having 9 to 50 ring atoms include the groups obtained by removing one hydrogen atom from the condensed aromatic heterocyclic group mentioned above as the heteroaryl group.

The thickness of the electron injecting/transporting layer is preferably, but not particularly limited to, 1 to 100 nm.

It is preferred that the electron injecting layer comprises an inorganic compound, such as an insulating material and a semiconductor, in addition to the nitrogen-containing ring derivative. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhanced. Examples of preferred alkali metal chalcogenide include Li$_2$O, K$_2$O, Na$_2$S, Na$_2$Se and Na$_2$O, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as CaF$_2$, BaF$_2$, SrF$_2$, MgF$_2$ and BeF$_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer in the invention may contain the electron-donating dopant mentioned above.

Hole Injecting/Transporting Layer

The hole injecting/transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

In the present invention, the hole injecting/transporting layer preferably comprises the biscarbazole derivative represented by formula (1). The hole injecting/transporting layer may comprises another material, such as an aromatic amine compound, for example, an aromatic amine derivative represented by formula (I):

(I)

wherein each of Ar$^1$ to Ar$^4$ represents a substituted or unsubstituted aromatic hydrocarbon group or fused aromatic hydrocarbon group having 6 to 50 ring carbon atoms, a substituted or unsubstituted aromatic heteroaryl group or fused aromatic heteroaryl group having 5 to 50 ring atoms, or a group wherein the aromatic hydrocarbon group or fused aromatic hydrocarbon group is bonded to the aromatic heteroaryl group or fused aromatic heteroaryl group.

L represents a substituted or unsubstituted aromatic hydrocarbon group or fused aromatic hydrocarbon group having 6 to 50 ring carbon atoms or a substituted or unsubstituted aromatic heteroaryl group or fused aromatic heteroaryl group having 5 to 50 ring atoms.

Examples of the compound represented by formula (I) are shown below

175
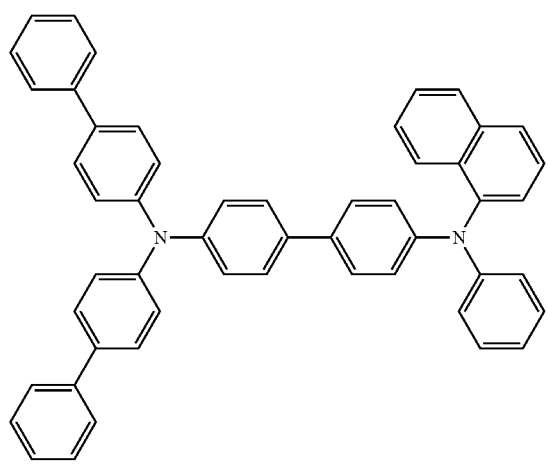
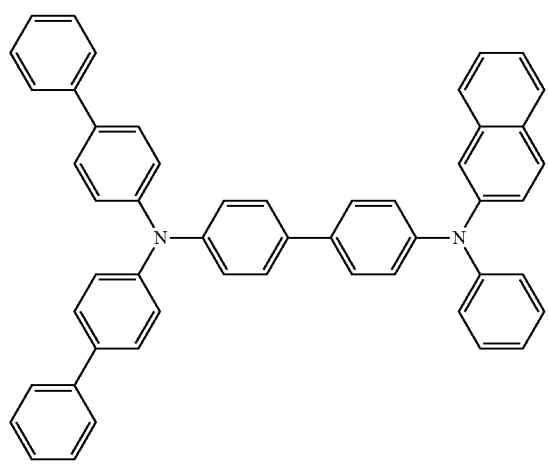
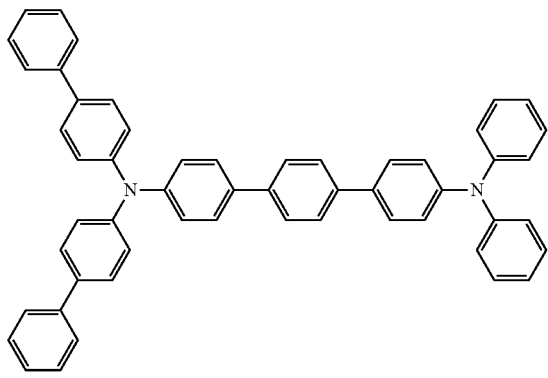
176
-continued
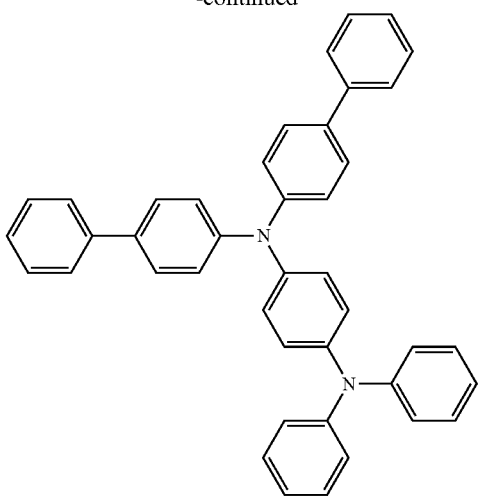
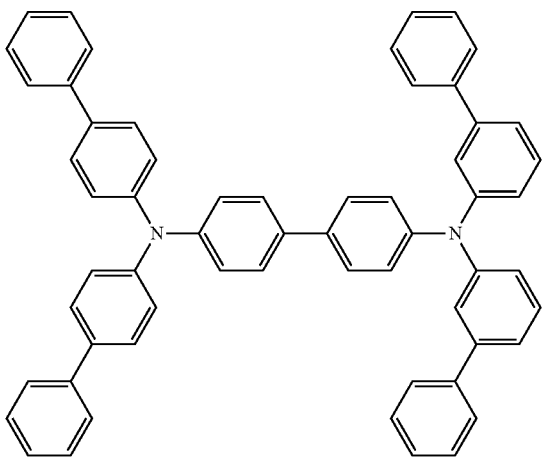
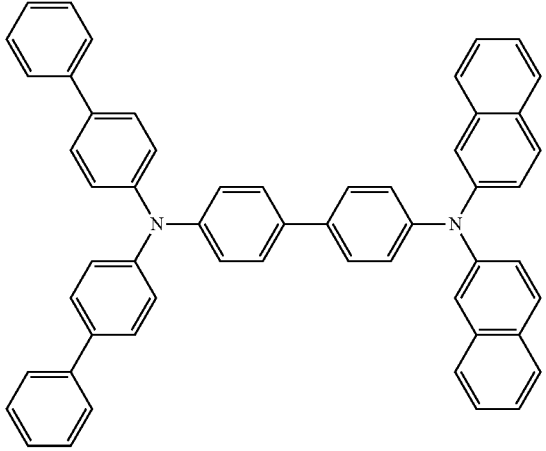

177
-continued
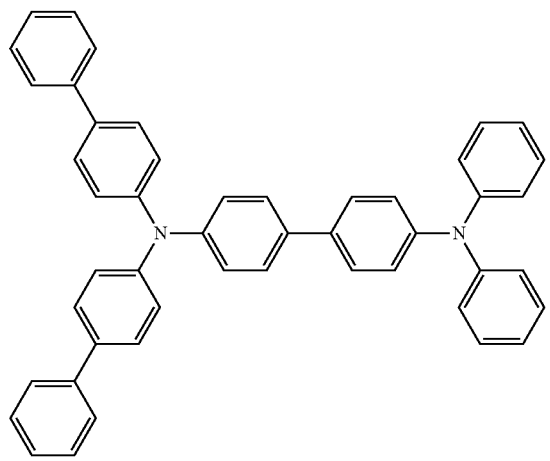
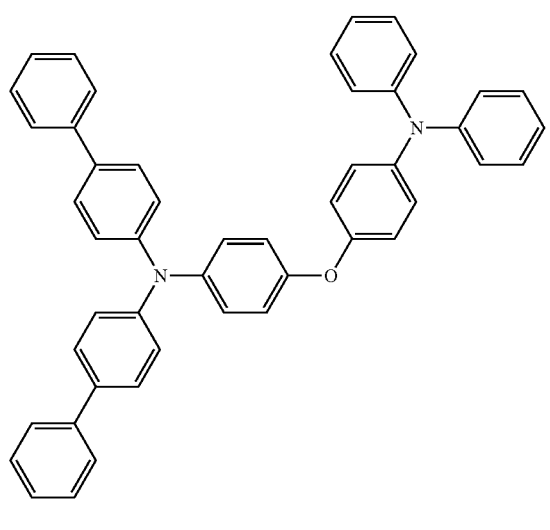
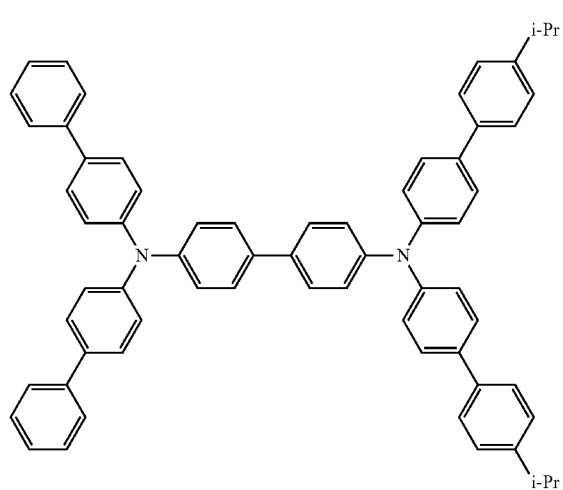
178
-continued
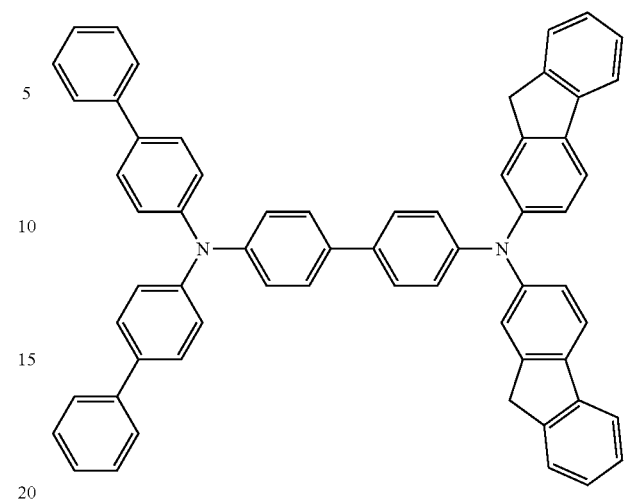
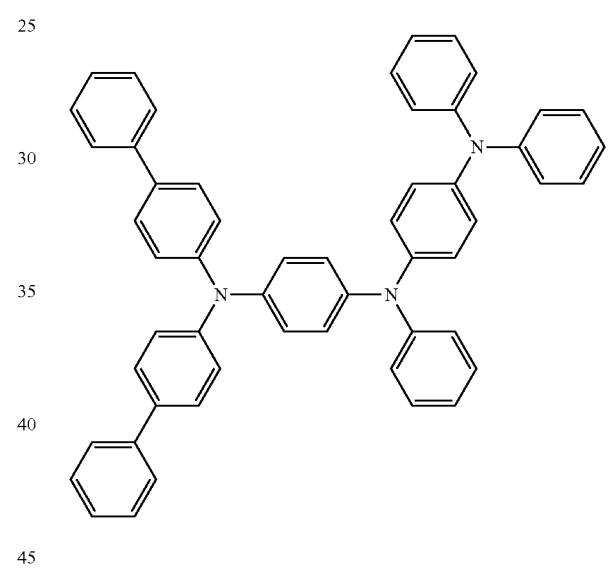
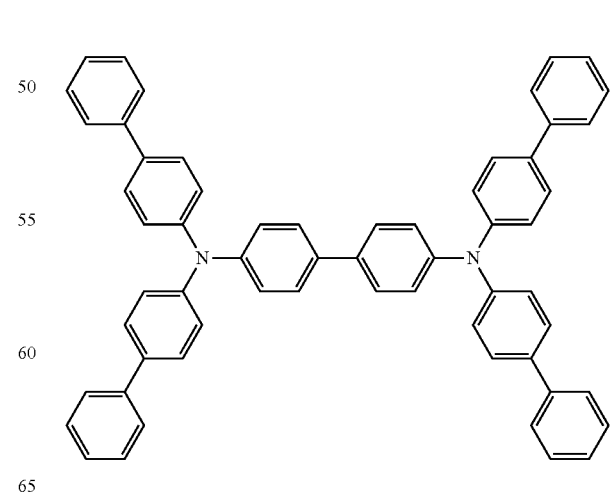

179
-continued
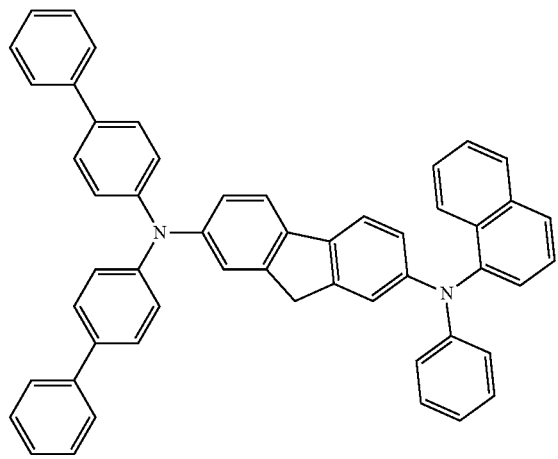
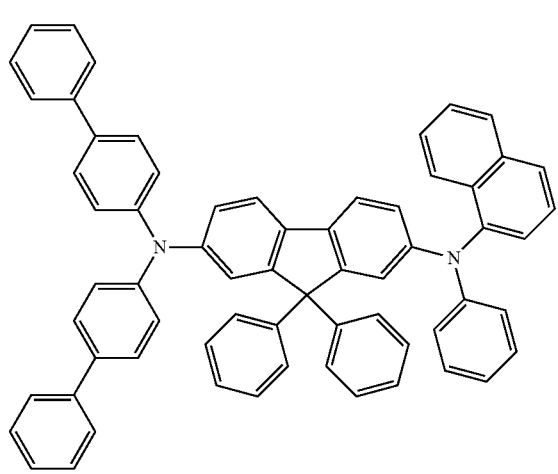
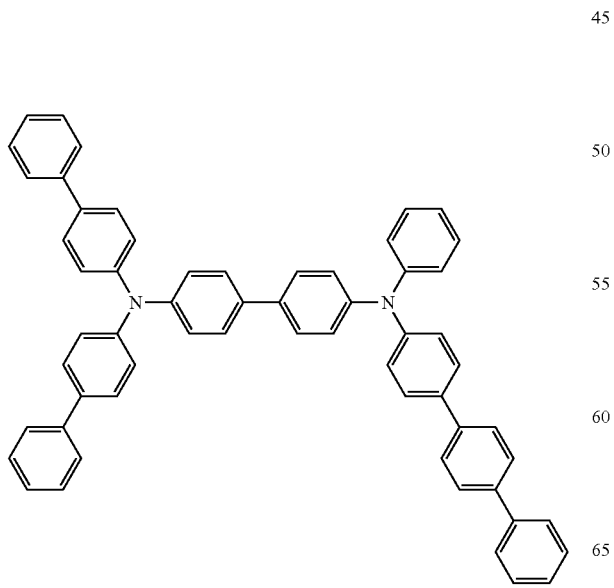
180
-continued
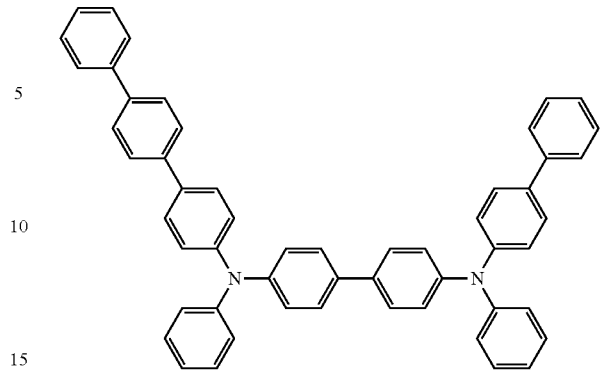
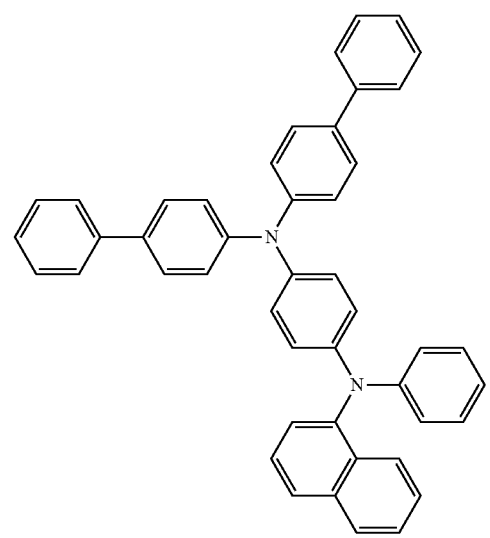
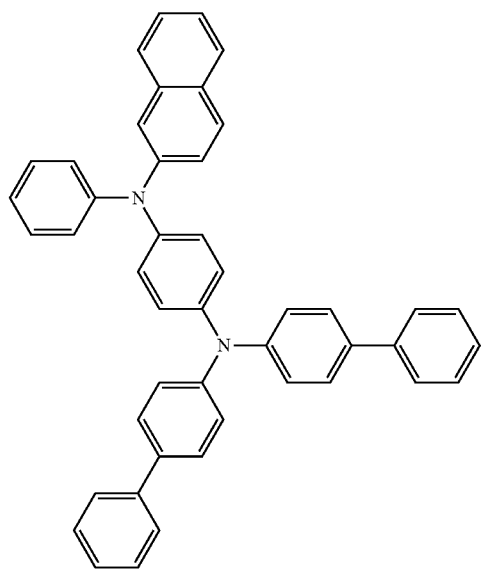

-continued
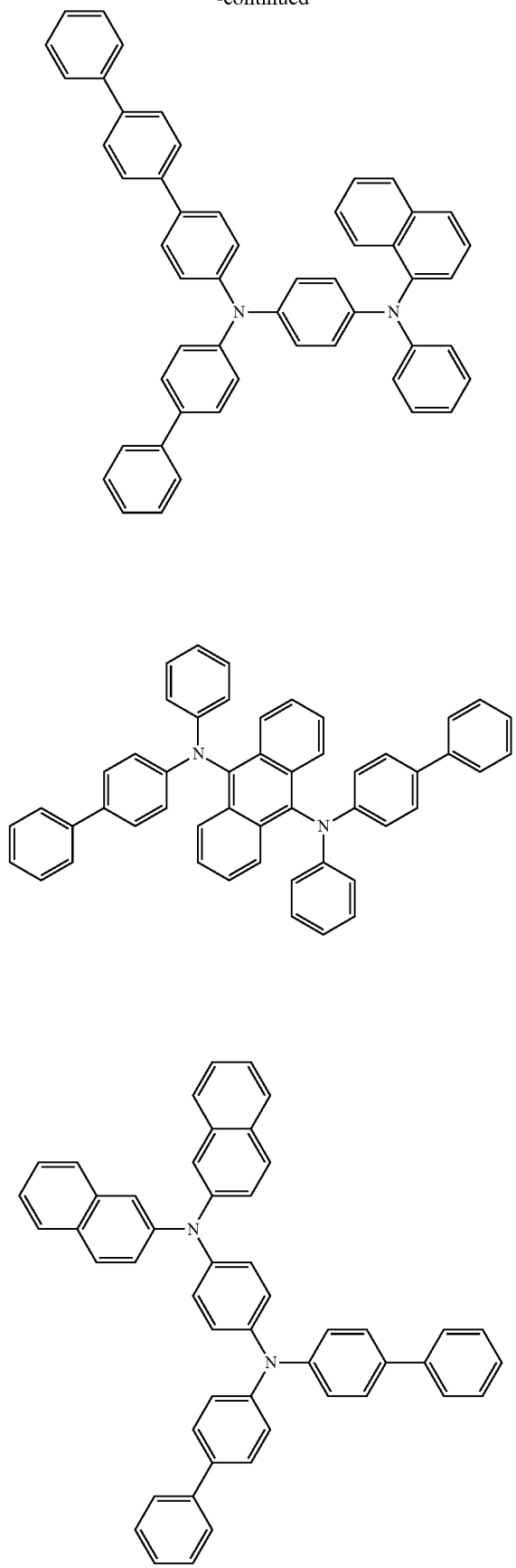
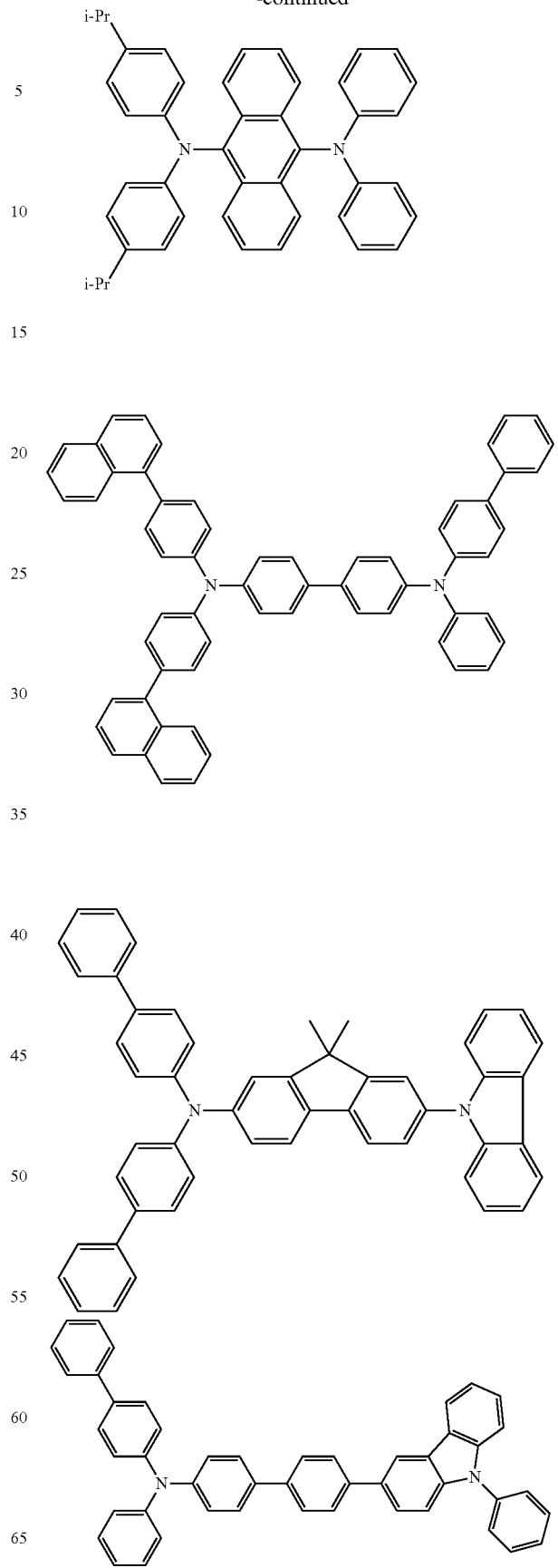

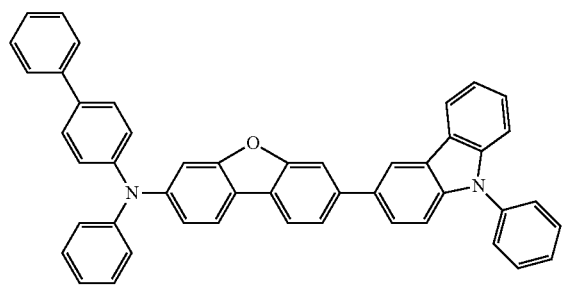
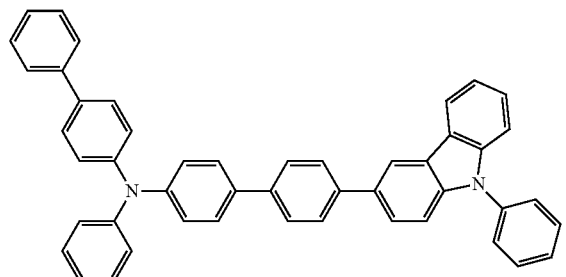
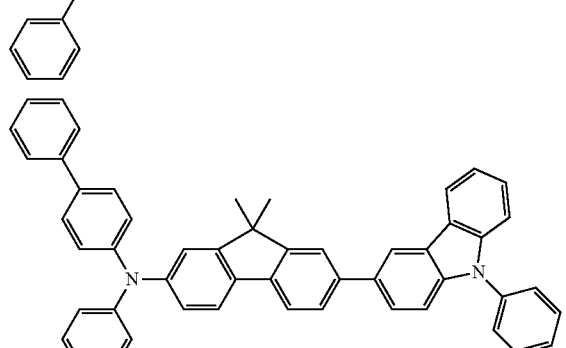
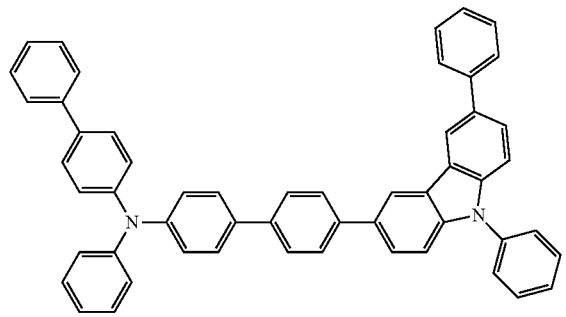
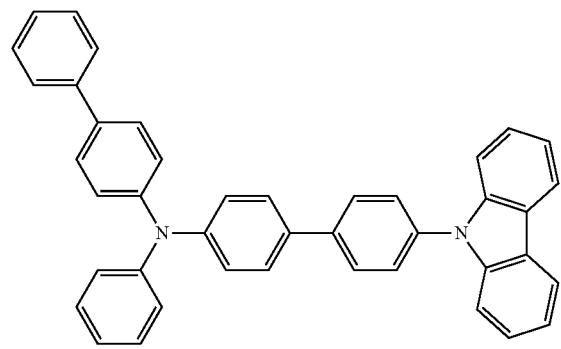
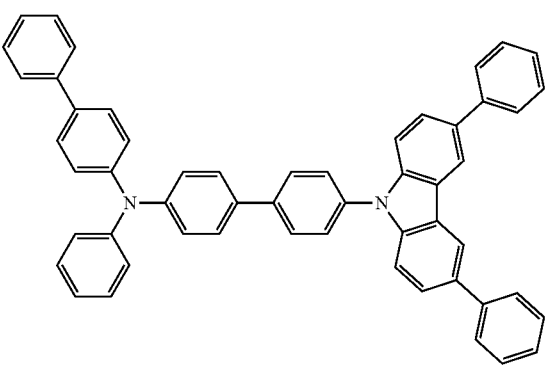
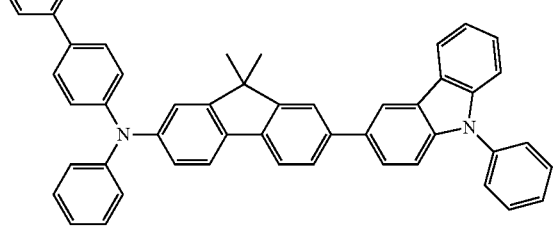
An aromatic amine represented by formula (II) is also preferably used to form the hole injecting/transporting layer:
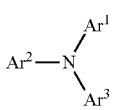
(II)
wherein $Ar^1$ to $Ar^3$ are the same as defined with respect to $Ar^1$ to $Ar^4$ of formula (I). Examples of the compound represented by formula (II) are shown below, although not limited thereto.
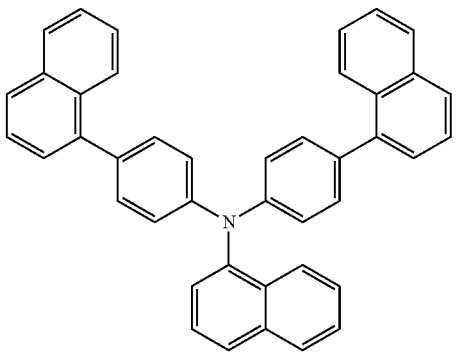

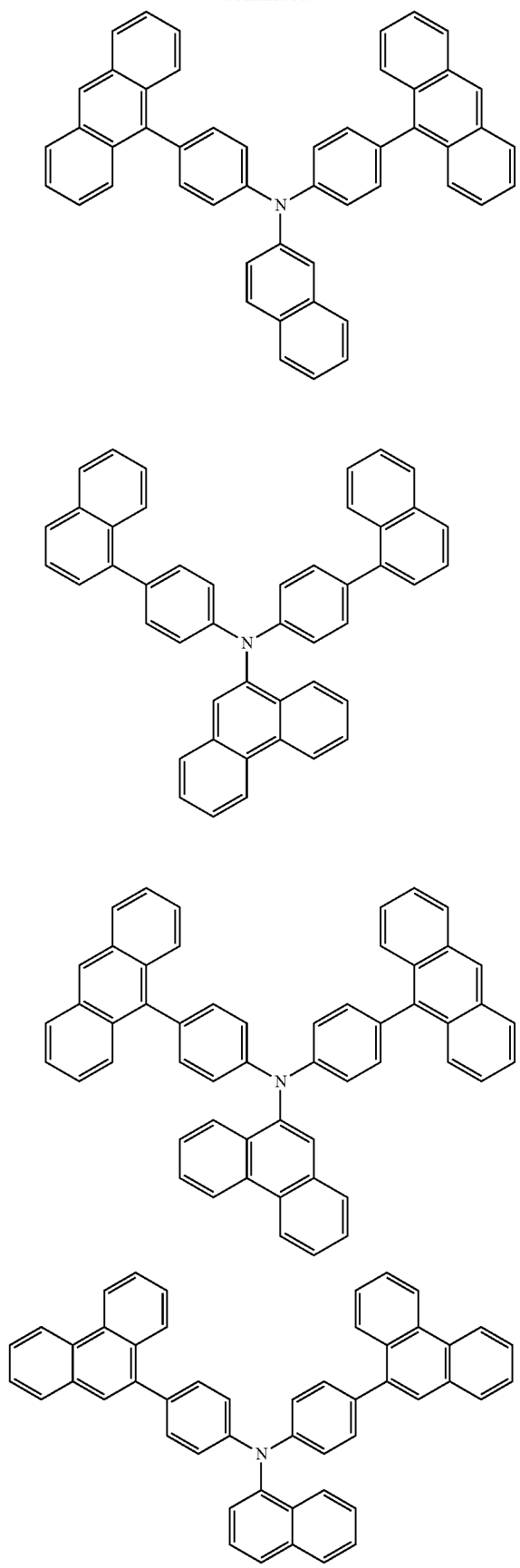
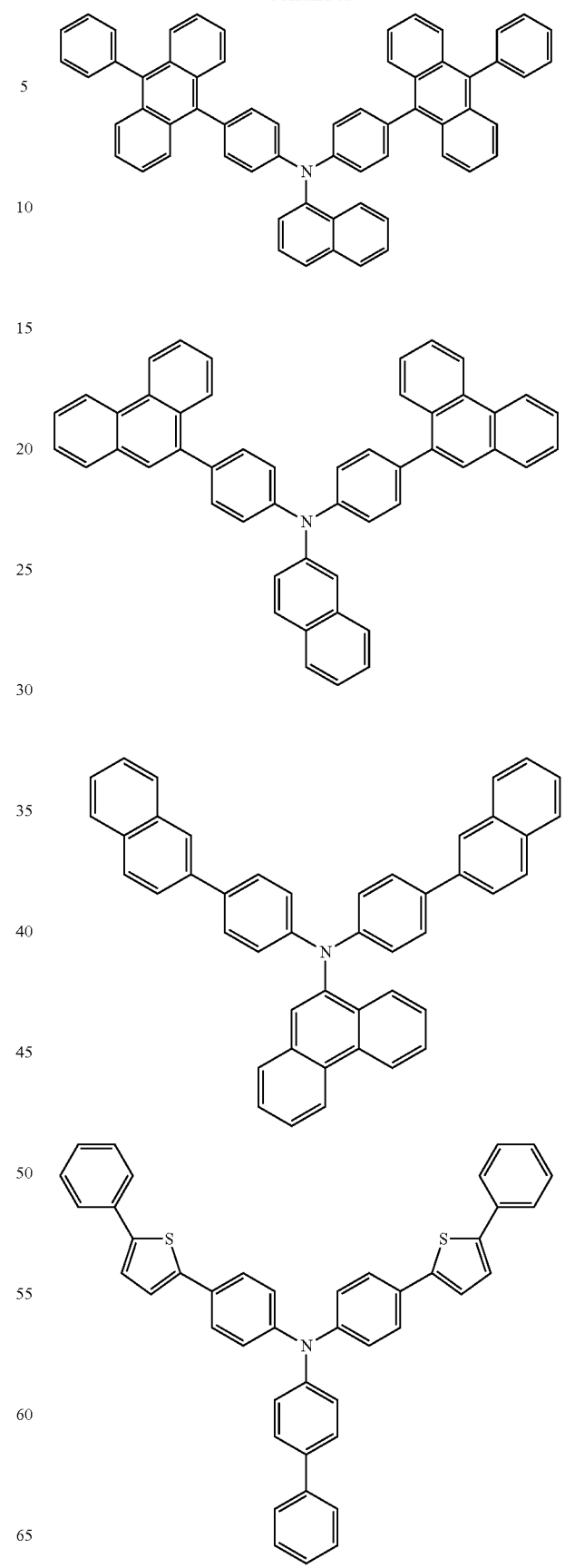

-continued

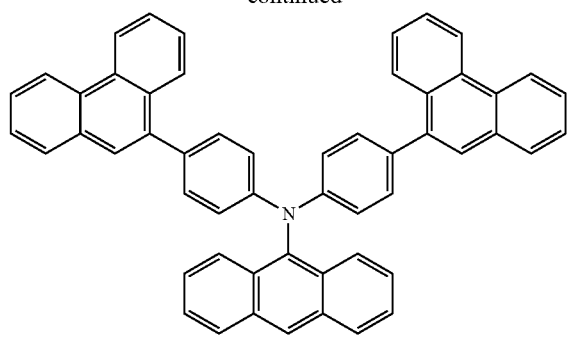

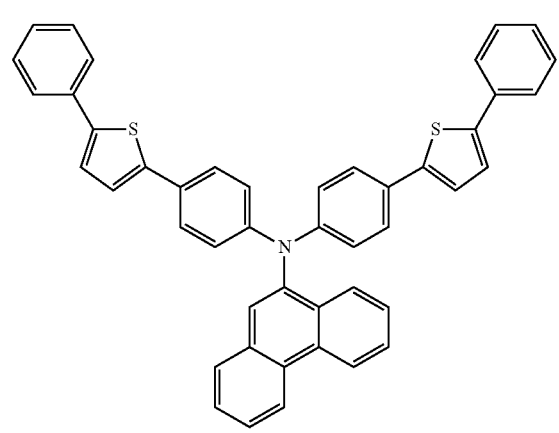

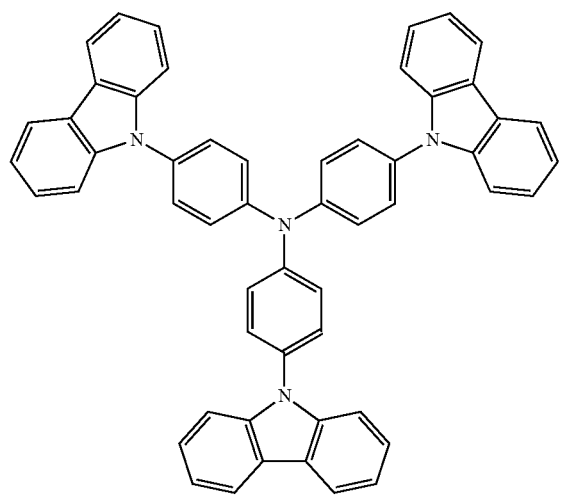

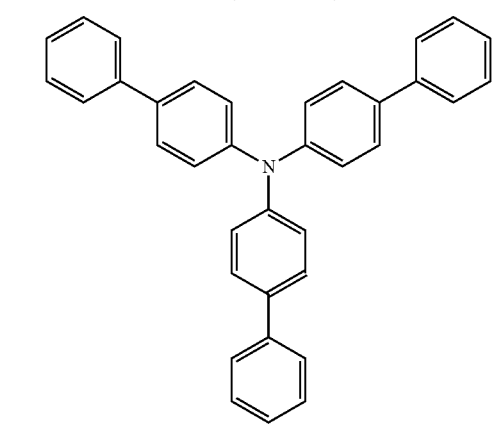

-continued

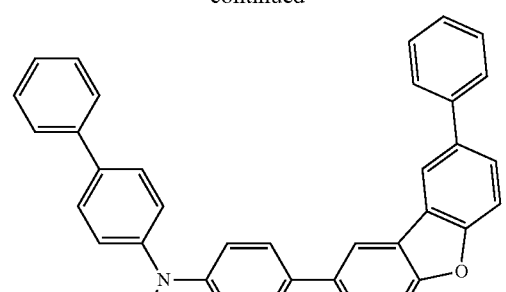

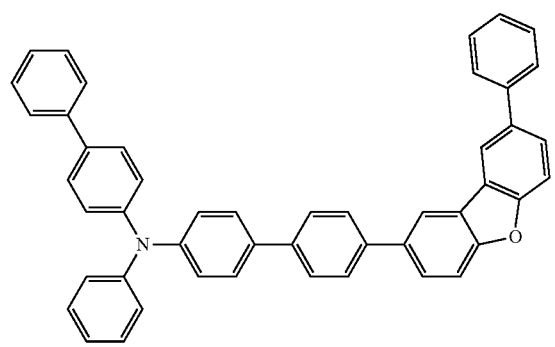

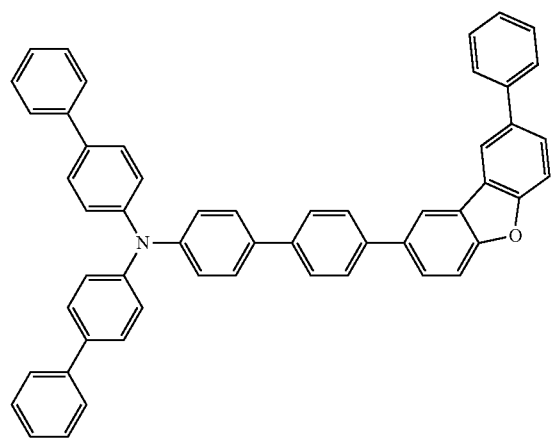

The hole transporting layer may be made into two-layered structure of a first hole transporting layer (anode side) and a second hole transporting layer (cathode side).

The thickness of the hole injecting/transporting layer is preferably 10 to 200 nm, although not particularly limited thereto.

The organic EL device of the invention may have a layer comprising an electron-accepting compound which is attached to the anode side of each of the hole transporting layer and the first hole transporting layer. With such a layer, it is expected that the driving voltage is lowered and the production cost is reduced.

The electron-accepting compound is preferably a compound represented by formula (10):

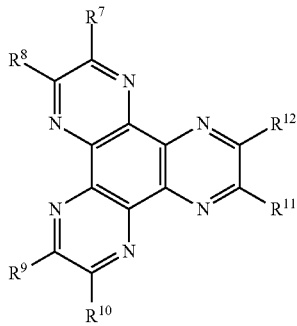

(10)

wherein $R^7$ to $R^{12}$ may be the same or different and each independently represent a cyano group, —$CONH_2$, a carboxyl group, or —$COOR^{13}$ wherein $R^{13}$ represents an alkyl group having 1 to 20 carbon atoms or a cycloalkyl group having 3 to 20 carbon atoms. One or more of a pair of $R^7$ and $R^8$, a pair of $R^9$ and $R^{10}$, and a pair of $R^{11}$ and $R^{12}$ may bond to each other to form a group represented by —CO—O—CO—.

Examples of $R^{13}$ include methyl group, ethyl group, n-propyl group, isopropyl group, n-butyl group, isobutyl group, t-butyl group, cyclopentyl group, and cyclohexyl group.

The thickness of the layer comprising the electron-accepting compound is preferably 5 to 20 nm, although not particularly limited thereto.

EXAMPLES

The present invention will be described in more detail with reference to the examples. However, it should be noted that the scope of the invention is not limited to the following examples.

Intermediate Synthesis 1: Synthesis of Intermediate 1

After adding 70 mL of ethanol to 15 g of carbazole, 6 mL of sulfuric acid, 3 mL of water, 8.2 g of periodic acid dihydrate, and 9.1 g of iodine were further added at room temperature. The resultant mixture was stirred for 4 h. The precipitate generated by adding water to the reaction product liquid was collected by filtration and washed with methanol. The obtained solid was dissolved in hot toluene and recrystallized. The purified solid was vacuum-dried to obtain 5.1 g of white solid, which was identified as Intermediate 1 shown below by FD-MS analysis.

Intermediate 1

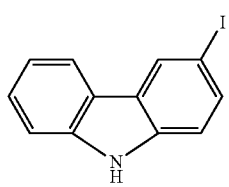

Intermediate Synthesis 2: Synthesis of Intermediate 2

After adding 5.90 mL of sulfuric acid and 70 mL of ethanol to 17.7 g of 9-phenylcarbazole, 6.03 g of potassium iodide and 7.78 g of potassium iodate, the resultant mixture was allowed to react at 75° C. for 2 h. After cooling, water and ethyl acetate were added and the resultant mixture was subjected to liquid-liquid extraction. The organic layer was washed with an aqueous sodium hydrogen carbonate solution and water and then concentrated. The obtained crude product was purified by silica gel column chromatography. The purified solid was vacuum-dried to obtain 21.8 g of while solid, which was identified as Intermediate 2 shown below by FD-MS analysis.

Intermediate 2

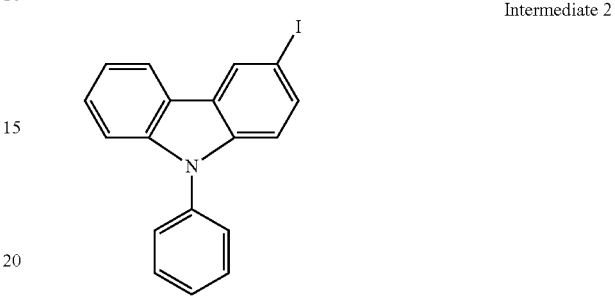

Intermediate Synthesis 3: Synthesis of Intermediate 3

In an argon atmosphere, dried toluene and dried ether were added to 13.1 g of Intermediate 2, and the resultant mixture was cooled to −45° C. After adding 25 mL of a 1.58 M solution of n-butyl lithium in hexane dropwise, the temperature was raised to −5° C. over one hour under stirring. The mixture was again cooled to −45° C. and 25 mL of triisopropyl boronate was gradually added dropwise, to allow the reaction to proceed for 2 h.

After raising the temperature to room temperature, the reaction product solution was added with a 10% diluted hydrochloric acid and stirred. The separated organic layer was washed with a saturated saline solution, dried over anhydrous magnesium sulfate, and filtered. The filtrate was concentrated and the obtained solid was purified by silica gel column chromatography. The purified solid was washed with n-hexane and vacuum-dried to obtain 7.10 g of solid, which was identified as Intermediate 3 shown below by FD-MS analysis.

Intermediate 3

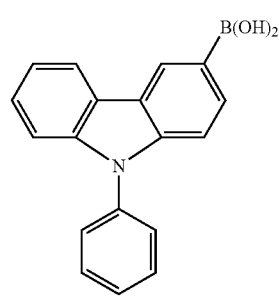

Intermediate Synthesis 4: Synthesis of Intermediate 4

In an argon atmosphere, a mixture of 2.05 g of Intermediate 1, 2.0 g of Intermediate 3, 0.15 g of tetrakis(triphenylphosphine)palladium, 20 mL of toluene, and 10.5 mL of 2 M aqueous solution of sodium carbonate was stirred at 80° C. for 7 h. The solid precipitated by adding water to the reaction product liquid was collected and washed with methanol. The washed solid was further washed with hot toluene and vacuum-dried to obtain 2.43 g of white solid, which was identified as Intermediate 4 shown below by FD-MS analysis.

Intermediate 4

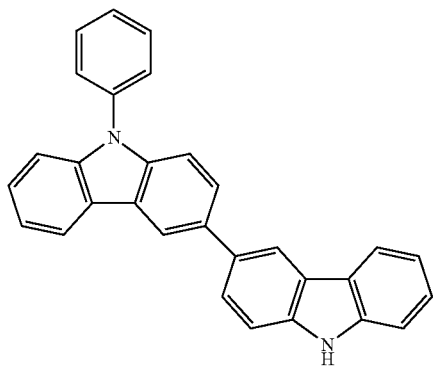

Intermediate Synthesis 5: Synthesis of Intermediate 5

In an argon atmosphere, 23 g of iodine, 9.4 g of periodic acid dihydrate, 42 mL of water, 360 mL of acetic acid, and 11 mL of sulfuric acid were added to 55 g of 2-bromo-9,9-dimethylfluorene. The resultant mixture was stirred at 65° C. for 30 min and then the reaction was allowed to proceed at 90° C. for 6 h. The reaction product was poured in to iced water and then filtered. The collected solid was washed with water and then methanol, to obtain 61 g of white powder, which was identified as Intermediate 5 shown below by FD-MS analysis.

Intermediate 5

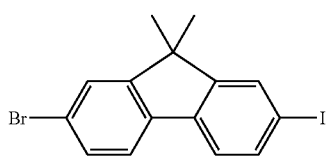

Intermediate Synthesis 6: Synthesis of Intermediate 6

In an argon atmosphere, 2 mL of trans-1,2-cyclohexanediamine and 300 mL of 1,4-dioxane were added to 40.0 g of Intermediate 5, 16.7 g of carbazole, 0.2 g of copper iodide (CuI), and 42.4 g of tripotassium phosphate and the resultant mixture was stirred at 100° C. for 20 h. After the reaction, the reaction product solution was added with 300 mL of water for extraction and then the water layer was removed. The organic layer was dried over sodium sulfated and then concentrated. The residue was purified by silica gel column chromatography to obtain 24.1 g of white crystal, which was identified as Intermediate 6 shown below by FD-MS analysis.

Intermediate 6

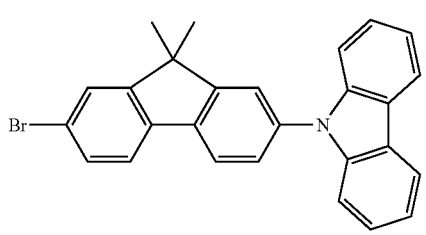

Intermediate Synthesis 7: Synthesis of Intermediate 7

In the same manner as in Intermediate Synthesis 6 except for using 28.2 g of 4-iodobromobenzene in place of Intermediate 5, 17.5 g of white solid was obtained, which was identified as Intermediate 7 shown below by FD-MS analysis.

Intermediate 7

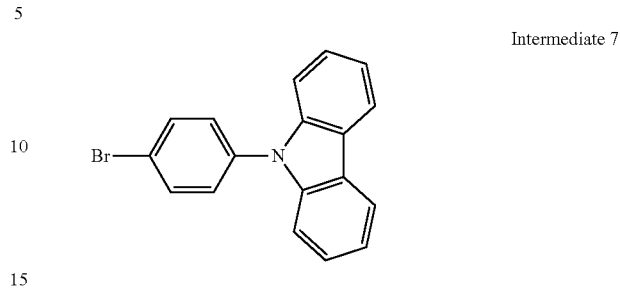

Synthesis Example 1

Production of Biscarbazole Derivative (H1)

In an argon atmosphere, 30 mL of dried xylene was added to 3.0 g of Intermediate 2, 3.0 g of Intermediate 4, 0.14 g of $Pd_2(dba)_3$, 0.17 g of $P(tBu)_3HBF_4$, and 1.1 g of sodium t-butoxide, and the resultant mixture was refluxed for 8 h under heating.

The solid precipitated by adding water to the reaction product liquid was collected and washed with hexane and then methanol. The washed solid was purified by silica gel column chromatography to obtain 3.1 g of white crystal, which was identified as the biscarbazole derivative (H1) shown below by FD-MS analysis.

H1

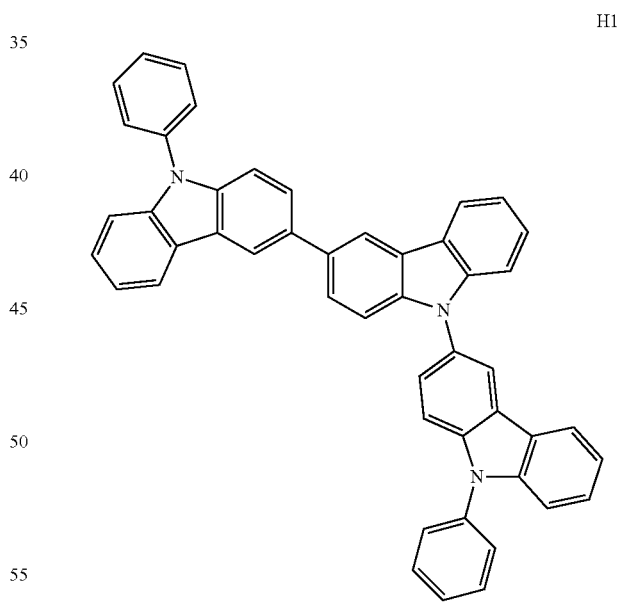

Synthesis Example 2

Production of Biscarbazole Derivative (H2)

In the same manner as in Synthesis Example 1 except for using 2.6 g of Intermediate 7 in place of Intermediate 2, 3.2 g of white powder was obtained, which was identified as the biscarbazole derivative (H2) shown below by FD-MS analysis.

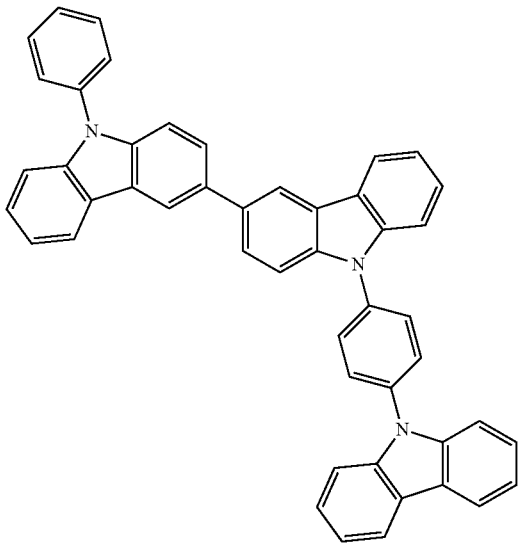

Synthesis Example 3

Production of Biscarbazole Derivative (H3)

In the same manner as in Synthesis Example 1 except for using 3.6 g of Intermediate 6 in place of Intermediate 2, 3.5 g of white powder was obtained, which was identified as the biscarbazole derivative (H3) shown below by FD-MS analysis.

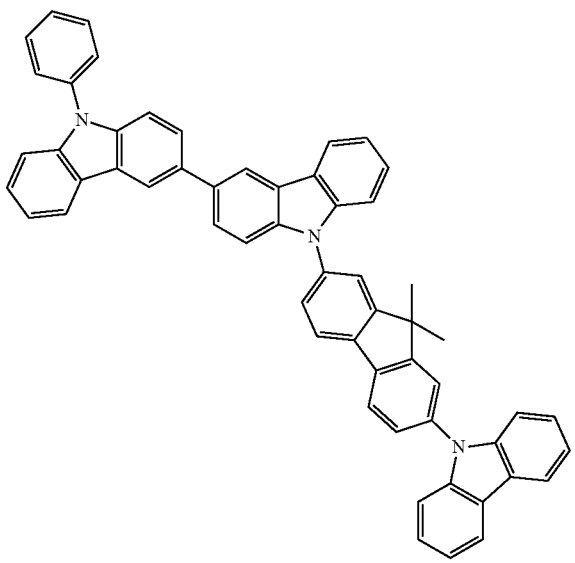

Example 1

Production of Organic EL Device

A glass substrate with an ITO transparent electrode having a size of 25 mm×75 mm×1.1 mm (manufactured by GEOMATEC Co., Ltd.) was ultrasonically cleaned in isopropyl alcohol for 5 min and then UV (ultraviolet)/ozone cleaned for 30 min.

The cleaned glass substrate with the transparent electrode line was mounted on the substrate holder of a vacuum deposition apparatus. First, the following electron-accepting compound (A) was vapor-deposited onto the surface on the side where the transparent electrode line was formed so as to cover the transparent electrode, thereby forming a film A having a thickness of 5 nm. On the film A, the following aromatic amine derivative (X1) as a first hole transporting material was vapor-deposited to form a first hole transporting layer having a thickness of 157 nm. Successively after the formation of the first hole transporting layer, the biscarbazole derivative (H1) obtained in Synthesis Example 1 as a second hole transporting material was vapor-deposited to form a second hole transporting layer having a thickness of 10 nm.

On the hole transporting layer, the compound (B) (host for phosphorescence) and Ir(ppy)$_3$ (dopant for phosphorescence) were vapor co-deposited in to a film having a thickness of 40 nm, to form a phosphorescent light emitting layer. The concentration of Ir(ppy)$_3$ was 10% by mass.

Then, a film of the compound (C) having a thickness of 20 nm, a film of LiF having a thickness of 1 nm, and a film of metallic Al having a thickness of 80 nm were successively deposited to form a cathode. The LiF film as the electron injecting electrode was formed at a film-forming speed of 1 Å/min.

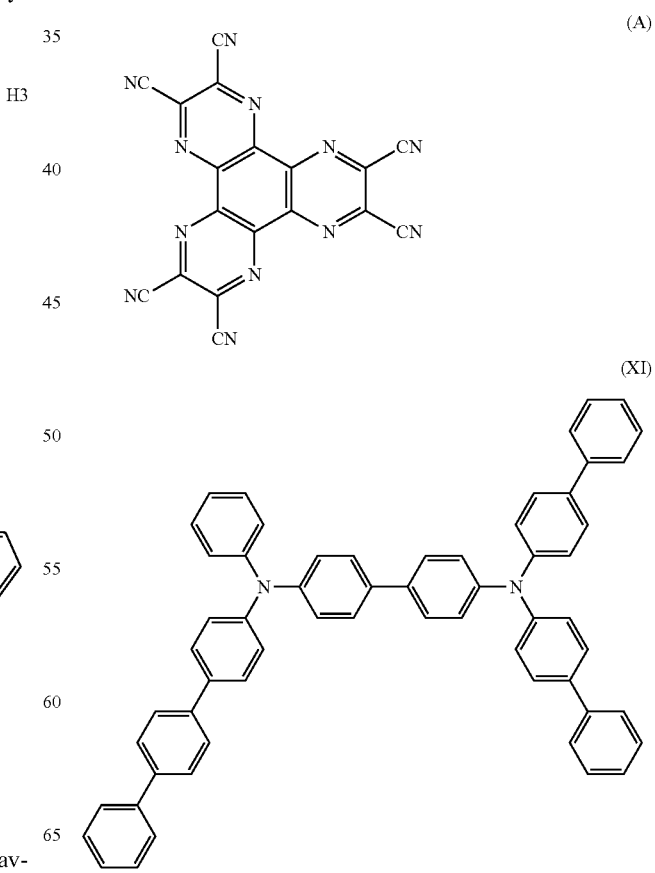

-continued

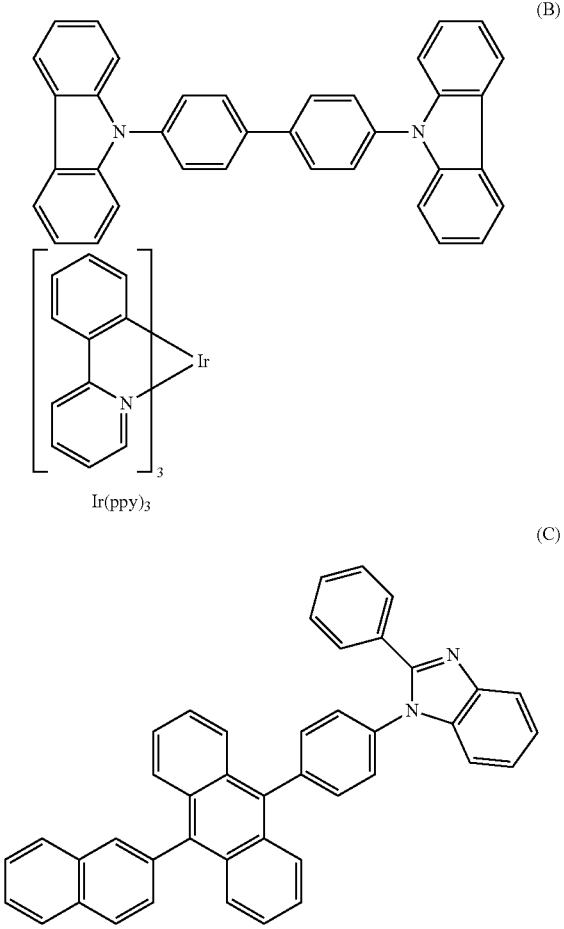

Ir(ppy)₃

Evaluation of Emission Performance of Organic EL Device

The organic EL device thus produced was measured for the luminance (L) and the current density by making the device emit light under a direct current drive, thereby determining the current efficiency (L/J) and the driving voltage (V) at a current density of 10 mA/cm². In addition, the organic EL device was measured for the lifetime at an initial luminance of 20000 cd/m². The results are shown in Table 1.

Examples 2 to 3

Each organic EL device was produced in the same manner as in Example 1 except for using the biscarbazole derivative (H2) (Example 2) or the biscarbazole derivative (H3) (Example 3) as the second hole transporting material in place of the biscarbazole derivative (H1). Each of the obtained organic EL devices was measured for the luminance (L) and the current density by making the device emit light under a direct current drive, thereby determining the current efficiency (L/J) and the driving voltage (V) at a current density of 10 mA/cm². In addition, each organic EL device was measured for the lifetime at an initial luminance of 20000 cd/m². The results are shown in Table 1.

Comparative Examples 1 and 2

Each organic EL device was produced in the same manner as in Example 1 except for using the comparative compound 1 or the comparative compound 2 shown below as the second hole transporting material in place of the biscarbazole derivative (H1). Each of the obtained organic EL devices was measured for the luminance (L) and the current density by making the device emit light under a direct current drive, thereby determining the current efficiency (L/J) and the driving voltage (V) at a current density of 10 mA/cm². In addition, each organic EL device was measured for the lifetime at an initial luminance of 20000 cd/m². The results are shown in Table 1.

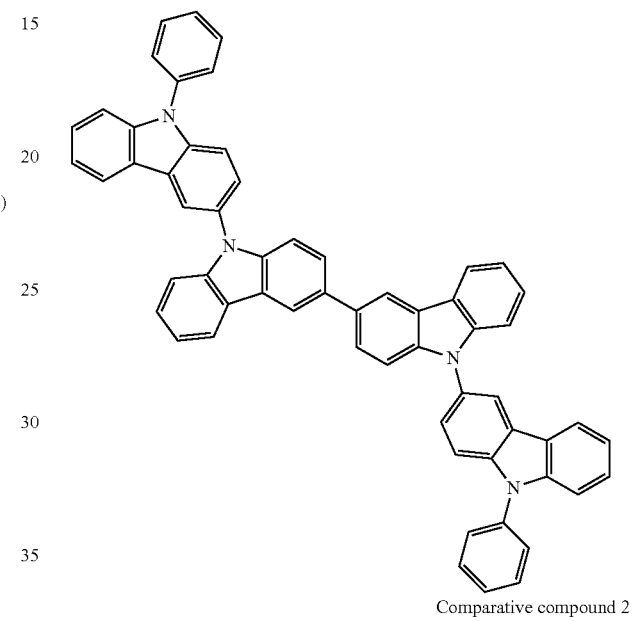

Comparative compound 1

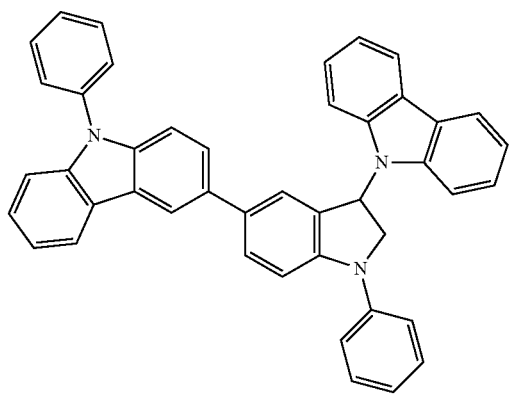

Comparative compound 2

TABLE 1

| | | Measured Results | | |
| | Second hole transporting material | current efficiency (cd/A) @10 mA/cm² | driving voltage (V) @ 10 mA/cm² | 80% lifetime (h) |
|---|---|---|---|---|
| Examples | | | | |
| 1 | H1 | 54.7 | 4.0 | 120 |
| 2 | H2 | 57.3 | 4.1 | 135 |
| 3 | H3 | 55.2 | 4.0 | 120 |

TABLE 1-continued

| | Second hole transporting material | current efficiency (cd/A) @10 mA/cm² | driving voltage (V) @ 10 mA/cm² | 80% lifetime (h) |
|---|---|---|---|---|
| Comparative Examples | | | | |
| 1 | comparative compound 1 | 40.7 | 3.8 | 60 |
| 2 | comparative compound 2 | 55.0 | 4.5 | 80 |

INDUSTRIAL APPLICABILITY

The biscarbazole derivative of the invention is useful as the material for realizing organic EL devices having a long lifetime and capable of driving at a low voltage.

What is claimed is:

1. A biscarbazole derivative represented by formula (1):

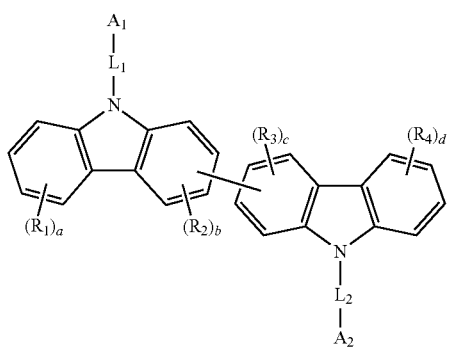

(1)

wherein:

$L_1$ and $L_2$ are identical or different and each independently represents a linker that is a single bond or a substituted or unsubstituted arylene group having 6 to 30 ring carbon atoms;

$R_1$ to $R_4$ are identical or different and each independently represents a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted aryl group having 6 to 30 ring carbon atoms, a substituted or unsubstituted aryloxy group having 6 to 30 ring carbon atoms, a substituted or unsubstituted arylsilyl group having 6 to 30 carbon atoms, a substituted or unsubstituted aralkyl group having 7 to 30 carbon atoms, or a substituted or unsubstituted heteroaryl group having 5 to 30 ring atoms, wherein the heteroaryl group is selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolinyl group, a cinnolinyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group;

adjacent $R_1$ groups, adjacent $R_2$ groups, adjacent $R_3$ groups, and adjacent $R_4$ groups may be bonded to each other to form a saturated or unsaturated, substituted or unsubstituted divalent group which completes a ring structure;

each of a and d independently represents an integer of 0 to 4;

each of b and c independently represents an integer of 0 to 3;

$A_1$ represents a substituted or unsubstituted aryl group having 6 to 30 ring carbon atoms or a substituted or unsubstituted heteroaryl group having 5 to 30 ring atoms, wherein the heteroaryl group is selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolinyl group, a cinnolinyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group;

$A_2$ represents a group represented by formula (2-1) or (2-2):

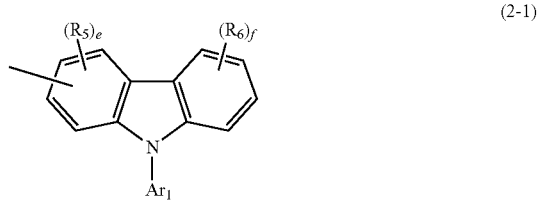

(2-1)

-continued (2-2)

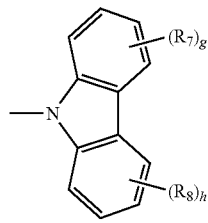

wherein:
Ar₁ represents a substituted or unsubstituted aryl group having 6 to 30 ring carbon atoms or a substituted or unsubstituted heteroaryl group having 5 to 30 ring atoms;
R₅ to R₈ are identical or different and each independently represents a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted aryl group having 6 to 30 ring carbon atoms, a substituted or unsubstituted aryloxy group having 6 to 30 ring carbon atoms, a substituted or unsubstituted arylsilyl group having 6 to 30 carbon atoms, or a substituted or unsubstituted aralkyl group having 7 to 30 carbon atoms;
adjacent R₅ groups and adjacent R₆ groups may be bonded to each other to form a saturated or unsaturated, substituted or unsubstituted divalent group which completes a ring structure;
f represents an integer of 0 to 4;
g and h are 0;
e represents an integer of 0 to 3; and
L₂ represents a single bond if A₂ is a group represented by formula (2-1), and L₂ represents a single bond or a substituted or unsubstituted arylene group having 6 to 30 ring carbon atoms if A₂ is a group represented by formula (2-2).

2. The biscarbazole derivative according to claim 1, wherein the biscarbazole derivative is represented by formula (3-1), (3-2), or (3-3):

(3-1)

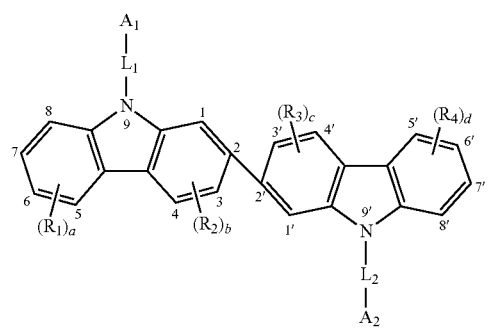

(3-2)

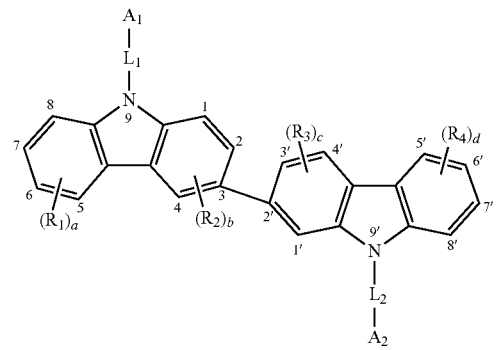

(3-3)

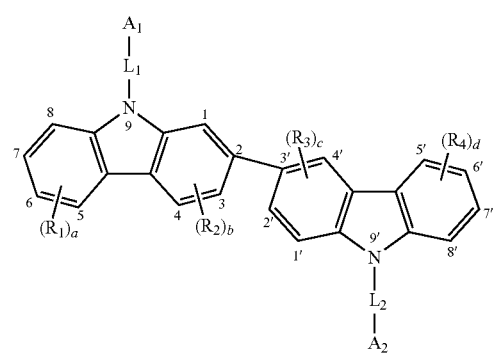

3. The biscarbazole derivative according to claim 1, wherein the biscarbazole derivative is represented by formula (3-4):

(3-4)

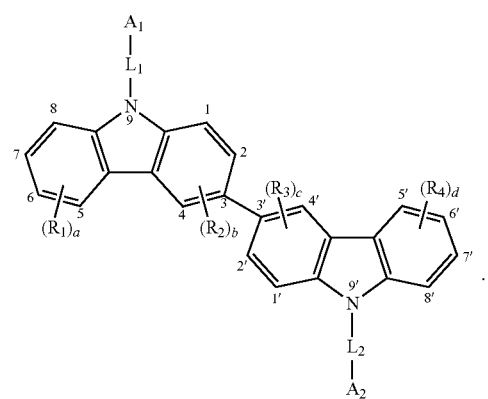

4. The biscarbazole derivative according to claim 1, wherein A₂ is represented by formula (2-3) or (2-4):

(2-3)

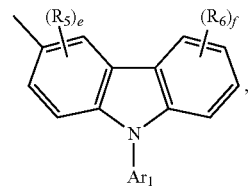

-continued (2-4)

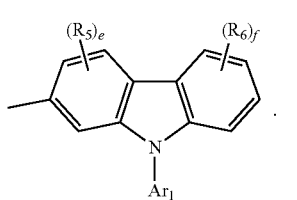

5. The biscarbazole derivative according to claim 1, wherein $L_2$ represents an arylene group having 6 to 30 ring carbon atoms, wherein the arylene group is a divalent residue of an aromatic compound selected from the group consisting of benzene, biphenyl, naphthalene, phenanthrene, fluorene, and 9,9-dimethylfluorene.

6. The biscarbazole derivative according to claim 1, wherein $L_2$ represents a substituted or unsubstituted 1,4-phenylene group.

7. The biscarbazole derivative according to claim 1, wherein $L_2$ represents a substituted or unsubstituted 1,3-phenylene group.

8. The biscarbazole derivative according to claim 1, wherein $L_2$ represents a substituted or unsubstituted 9,9-dimethylfluorene-2,7-diyl group.

9. The biscarbazole derivative according to claim 1, wherein the heteroaryl group having 5 to 30 ring atoms for $R_1$ to $R_4$ and $A_1$ is selected from the group consisting of a furyl group, a thienyl group, a benzofuranyl group, a benzothiophenyl group, dibenzofuranyl group, and a dibenzothiophenyl group.

10. A material suitable for an organic electroluminescence device, the material comprising the biscarbazole derivative according to claim 1.

11. A hole transporting material comprising the biscarbazole derivative according to claim 1.

12. An organic electroluminescence device comprising an anode, a cathode and one or more organic thin layers disposed between the anode and the cathode, wherein at least one layer of the organic thin layers comprises the biscarbazole derivative according to claim 1.

13. The organic electroluminescence device according to claim 12, wherein the organic thin layers comprise a hole transporting layer, a hole injecting layer, or both, and the hole transporting layer, the hole injecting layer, or both, comprise the biscarbazole derivative.

14. The organic electroluminescence device according to claim 13, wherein a layer comprising a compound represented by formula (10):

(10)

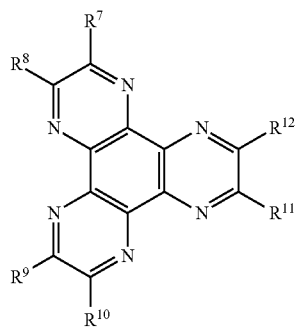

wherein $R^7$ to $R^{12}$ are identical or different and each independently represent a cyano group, —$CONH_2$, a carboxyl group, or —$COOR^{13}$ wherein $R^{13}$ represents an alkyl group having 1 to 20 carbon atoms or a cycloalkyl group having 3 to 20 carbon atoms, provided that a pair of $R^7$ and $R^8$, a pair of $R^9$ and $R^{10}$, and a pair of $R^{11}$ and $R^{12}$ may bond to each other to form a group represented by —CO—O—CO—, is attached to the hole transporting layer, the hole injecting layer, or both.

15. The organic electroluminescence device according to claim 12, wherein the organic thin layers comprise a light emitting layer, and the light emitting layer comprises a phosphorescent emitting material.

16. The organic electroluminescence device according to claim 15, wherein the phosphorescent emitting material is an ortho-metallated complex comprising a metal selected from the group consisting of iridium (Ir), osmium (Os) and platinum (Pt).

17. The organic electroluminescence device according to claim 12, wherein the organic thin layers comprise a light emitting layer, and the light emitting layer comprises a fluorescent emitting material.

18. The organic electroluminescence device according to claim 12, wherein the organic thin layers comprise an electron transporting layer, and the electron transporting layer comprises a nitrogen-comprising heterocyclic derivative represented by any one of formulae (60) to (62):

(60)

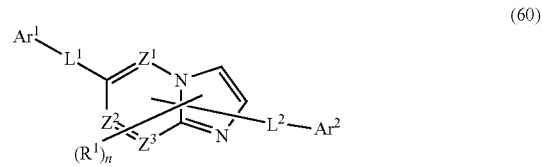

(61)

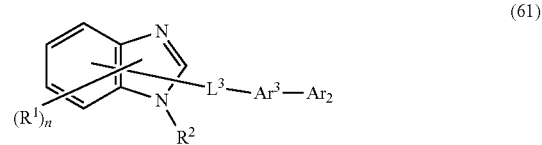

(62)

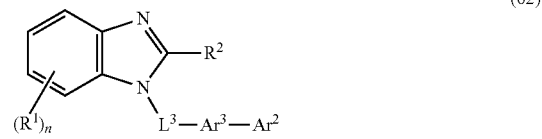

wherein $Z^1$, $Z^2$, and $Z^3$ each independently represent a nitrogen atom or a carbon atom;
$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms;
n is an integer of 0 to 5, and when n is an integer of 2 or more, plural $R^1$ groups may be identical or different, and two adjacent $R^1$ groups may bond to each other to form a substituted or unsubstituted hydrocarbon ring;
$Ar^1$ represents a substituted or unsubstituted aryl group having 6 to 50 ring carbon atoms or a substituted or unsubstituted heteroaryl group having 5 to 50 ring atoms;

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms;

provided that one of $Ar^1$ and $Ar^2$ is a substituted or unsubstituted condensed aromatic hydrocarbon group having 10 to 50 ring carbon atoms or a substituted or unsubstituted condensed aromatic heterocyclic group having 9 to 50 ring atoms;

$Ar^3$ represents a substituted or unsubstituted arylene group having 6 to 50 ring carbon atoms or a substituted or unsubstituted heteroarylene group having 5 to 50 ring atoms; and $L^1$, $L^2$, and $L^3$ each independently represent a single bond, a substituted or unsubstituted arylene group having 6 to 50 ring carbon atoms or a substituted or unsubstituted divalent condensed aromatic heterocyclic group having 9 to 50 ring atoms.

* * * * *